United States Patent
Owens et al.

(10) Patent No.: US 6,825,035 B1
(45) Date of Patent: Nov. 30, 2004

(54) COMPOSITIONS AND METHODS FOR MODULATING EXPRESSION WITHIN SMOOTH MUSCLE CELLS

(75) Inventors: Gary K. Owens, Earlysville, VA (US); Christopher Mack, Chapel Hill, NC (US); Randall Blank, Charlottesville, VA (US)

(73) Assignee: Setagon, Inc., Charlottesville, VA (US)

( * ) Notice: Subject to any disclaimer, the term of this patent is extended or adjusted under 35 U.S.C. 154(b) by 0 days.

(21) Appl. No.: 09/807,757

(22) PCT Filed: Oct. 22, 1999

(86) PCT No.: PCT/US99/24972

§ 371 (c)(1),
(2), (4) Date: Apr. 17, 2001

(87) PCT Pub. No.: WO00/24254

PCT Pub. Date: May 4, 2000

Related U.S. Application Data

(60) Provisional application No. 60/105,330, filed on Oct. 23, 1998.

(51) Int. Cl.⁷ .......................... C12N 5/10; C12N 15/63; C07H 21/04; A01K 67/00
(52) U.S. Cl. .................. 435/325; 536/24.1; 435/320.1; 800/13
(58) Field of Search ...................... 536/24.1; 435/320.1, 435/325; 800/13

(56) References Cited

PUBLICATIONS

Sigmund C.D. Viewpoint: are studies in genetically altered mice out of control?☐☐Arterioscler Thromb Vasc Biol. Jun. 2000;20(6):1425–9.*
Wall R.J. Transgenic Livestock: progress and prospects for the future. Theriogenology, 1996, 45:57–68.*
NCBI Online, Nucleotide Sequence Accession No. S76011 (gi:242241).*
Shimizu et al. The smooth muscle alpha–actin gene promoter is differentially regulated in☐☐smooth muscle versus non–smooth muscle cells. J Biol Chem. Mar. 31, 1995;270(13):7631–43.*
Blank et al. Elements of the smooth muscle alpha–actin promoter required in cis for☐☐transcriptional activation in smooth muscle. Evidence for cell type–specific☐☐regulation. J Biol Chem. Jan. 15, 1992;267(2):984–9.*
Doetschman T. Interpretation of phenotype in genetically engineered mice.☐☐Lab Anim Sci. Apr. 1999;49(2):137–43.*

* cited by examiner

Primary Examiner—Anne-Marie Falk
Assistant Examiner—Daniel M. Sullivan
(74) Attorney, Agent, or Firm—Townsend and Townsend and Crew, LLP

(57) ABSTRACT

The present invention relates to promoters, enhancers and other regulatory elements that direct expression within SMC, comprising nucleotide sequences from the 5' regulatory region and the first intron, and transcriptionally active fragments thereof, that control expression of an SM α-A. Specifically provided are expression vectors, host cells and transgenic animals wherein an SM α-A regulatory region is capable of controlling expression of a heterologous gene, over-expressing an endogenous SMC gene or an inhibitor of a pathological process or knocking out expression of a specific gene believed to be important for an SM-related disease in SMC. The invention also relates to methods for using said vectors, cells and animals for screening candidate molecules for agonists and antagonists of disorders involving SMC. The invention further relates to compositions and methods for modulating expression of compounds within SMC, and to screening compounds that modulate expression within SMC. Methods for using the molecules and compounds identified by the screening assays for therapeutic treatments also are provided.

15 Claims, 27 Drawing Sheets

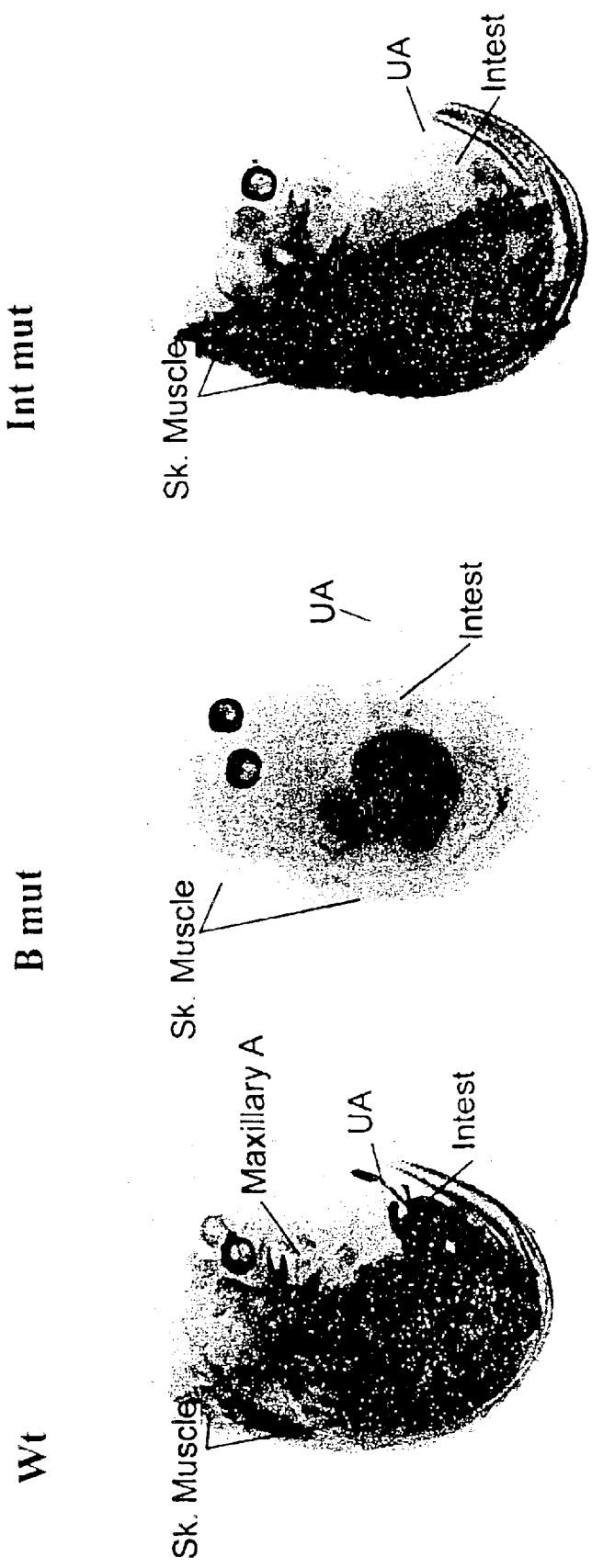

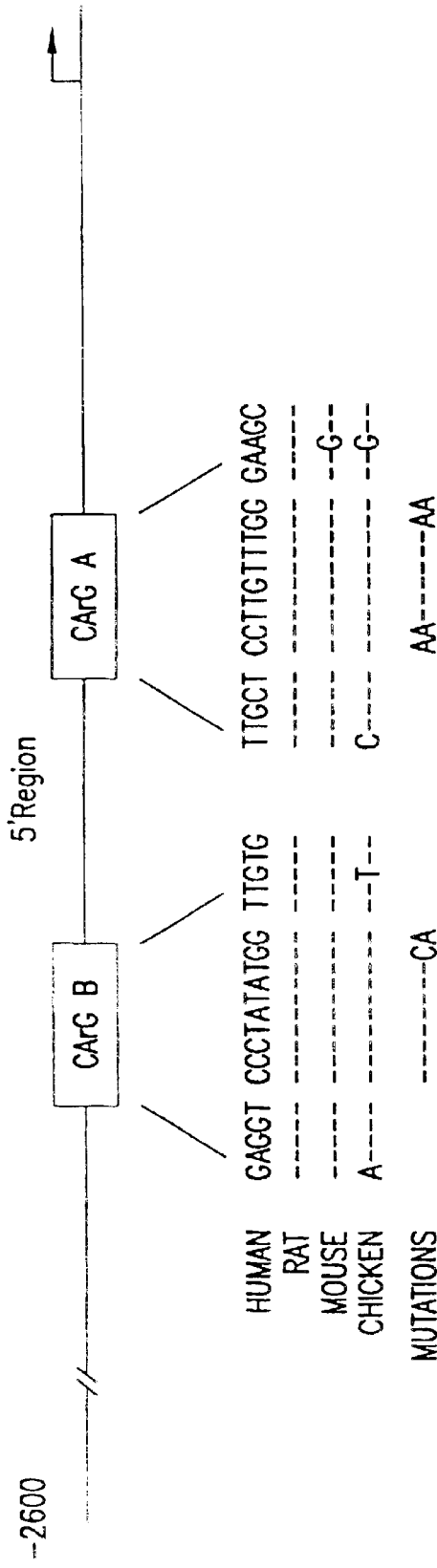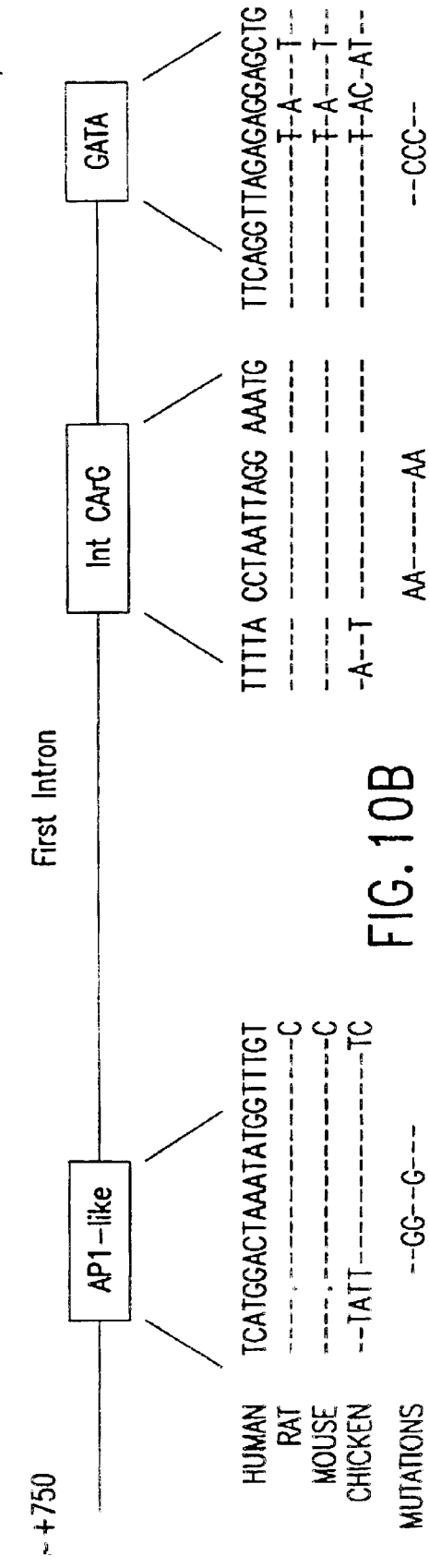

Figure 1:
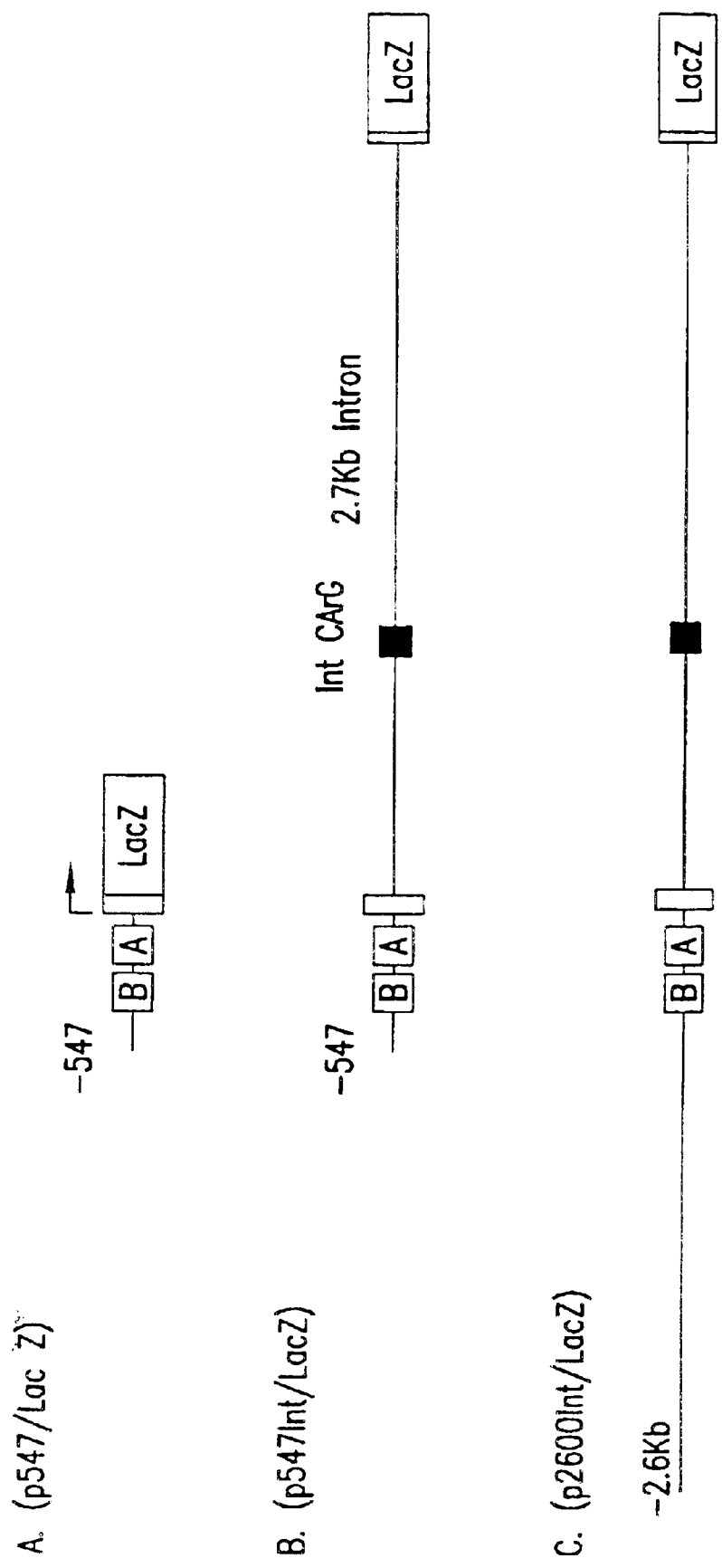

```
          1                                                        50
human     ---------- ---------- ---------- -AGAGAGCAA GCAAGAGCAG
rat       ---------- ---------- --GACATGGT AGCGTGAGTA GACAGCTGCT
mouse     ACACCATAAA ACAAGTGCAT GAGCCGTGGG AGCGTGAGTC GACAGCTGCT
chicken   ---------- ---------- ---------- ---------- ----------

51                                                       100
human     GGAAAACTGC CTTATAAAAC CATCAGATAT CGTGAGAACT CACTCACTTT
rat       GGCATTCACC CTGGGCTTTC CCTGACATGC CAACAGTTCA GAGCCACT.T
mouse     GCCATTCACC CTGGGGTTTC CCTAACATGT GCACAGTTCA GAAGCACTCC
chicken   ---------- ---------- ---------- ---------- ----------

101                                                      150
human     CATGAGAACA GCATGGTATA AAACGCCCCC ATCGATCCAG TCACCTCCCA
rat       ATGGATCCGT CTAAAATATC TCCATCATGA ATTGAATCAG AACCTTGGCT
mouse     CAGAATCCAT CCAAAATATC TCTATCATGA ATGGAATCAG AACCTTGGCT
chicken   -GAATTCATG GGCTTTTTGA ATTTGTAGTG GTTTGAGATG GAGTTTGGAG 151                                                      200
human     CCATGCCTTT CTCTGGACAT GGG...ATTA TGGAGATTAG AATTCGAGAC
rat       TGCAGGAGGG AAGTAGAGAA AGGTAAAGTC GTTGACTGTC CATTGAAGCC
mouse     TGCAGGAGGA AAGTACAGAA ATGTAAAGTC ACTGACTGTC CATCAAAGCC
chicken   ATGCTAATTT CTGATCTCTA GTAGTAGTTC AAGGGCAATG TATTGTTACT 201                                                      250
human     GAGATTTGGG TGGGGACGTA GAACCAAACC ATATCACCTG GTCTCTCTA.
rat       AAAGAGCTGA TGATGTCTTT GAAGAATGG. ......CAGG GTCACTTGAT
mouse     AACGATCTGA TGCCTTTGAA GAATGATAGG GTCACTTGAG GTCACTTGAT
chicken   GTGAAAGGGC TGCTCATGAG ACACAGTCTG CCTAGAGAAC AGCTGGCTGC 251                                                      300
human     ....CTTCCT GTCAAGGAGG TTAGTGGGCA GAGAGGAGGG CTACAGAGGC
rat       CGCTCTTTCT GTCCAGTGGG CTCATAAACA CGGAGGAGGA TGAGCAGGCT
mouse     CTCTGTTTCT GTCCAGTGGG CTCATAGTCA TGGAGGAGAG TGAGCAGGCT
chicken   AGCCAAATAA ATCCAGTCCT CTGA.AAATA GCTCATACAT TGAGAACCTT
```

FIG.12A

```
                  301                                                        350
        human    TTCCTTTGAA CAATCTCCTT TCTTTTCCAA A........C TACTTCTTTG
          rat    TCATTTCAAC ATTTCAAACT TCTTTTACAA .........T TTTTTTTATG
        mouse    TCATTTCAAC ATTTCAAATT TCTTTTACAA AGTTTTTTTT TTTTTTTATG
      chicken    TGCTTTAGTT GCTAAAAATA TGCTCAGGGC AAAGCTAGCT AGAGGTTATG 351                                                        400
        human    ACAGGCTGCT GGGTAGACTC TCTGGTCAAA GGATGGTCCC TACTTATGCT
          rat    ACGGGGCAAT GGGTCCTCTC TGTGGCCAAA AGACGGTCCT TAAGCATGAT
        mouse    ACAGGGTGAC TGGTGATCTC TGTGGGCAAA GGATGGTCCT TAATCATGCT
      chicken    AAATTCAGCA ACTTTATTAT GAATGTTTTG AGATAGGAGT TTACAACTTG 401                                                        450
        human    GCTAAATTGC TCGGTGACAA ATTAGTAGAC AAAGCTAATG CACCAAAAAA
          rat    ATCAGGGGTC AGCGATAAAC CAACAACATG CACGTGGACT GTACCTAGGG
        mouse    GTTAAGGGTC AGTAAAAAGC CAGCAACATG CGGAATG... ....TTAAGG
      chicken    TGTCCATCAG TGGAATTGAC ACTAGGATGA AGCTTGTCCA CAGTTCCTAG 451                                                        500
        human    ATGAATGTAG TTATAGTAAT GCTAACATCC AAATTCCTCT TTGTAAGACA
          rat    GTTAACGCAG TTACAGTGAT TCTGACTTCT AAGTTCCTCT TAGGGTAACA
        mouse    GTTAAAGCAG TTACAGTGAT TCTGACTTCT AAGTTACTCT TTGGGCAACA
      chicken    TGCTTTGGAA ATAAACTGAT GGAGACAGGA TATTGATTGT CACCCATTAC 501                                                        550
        human    TAGGCCTGTC AACCTTGTCT CCATACTTC. .........A ATTCCTATTT
          rat    TAGGCTGGTG AATCCTGATT ACATACTTCC ATATGTAATA CATACAGACT
        mouse    CAGGCTGGTT AATCCTCACT ACATACTTC. .........A GTTCCTGGTT
      chicken    AGGCTAGGGG CACCATAACA ACCTGTTAGC AGAACGTTTA CACAGCCTTC 551                                                        600
        human    CCA.CTCACC TCCCTCAAGA ACTTGATTTA TAA...ACAGT GTGCCTACCA
          rat    TCA.TTGATA CTACACACAG ACTCCA.GAC TACATACAAT GTGGCTTCCA
        mouse    TCA.TTACTA CAACACAAAG ACACAATGTA TAAGTACAAT GTAGCTTCCA
      chicken    AAAGACCCTA CCATGAACCC TATGCAACAG CAGGTACTTC TTTTAGTATC
```

FIG. 12B

```
                601                                                       650
      human  TAAAATCATC ACTCCCTCTA TGTATTTATA GACGACTGAA GGAATATCTT
        rat  TAAAATGATC ACT.CCTCTG CAGATTCGCA GGTGAC.CCA AGCATCT.TT
      mouse  TAAAAACATG ACT.CCTCTG CATATTTATG GGTGACTCGA AGCATCT.TT
    chicken  CCCAAGTGCA GACCTTTTAA GTGAATTTGT GGCAAAATTC AGTAGCTGTT 651                                                       700
      human  TCTTCTTTGC ATGCTACCGT GGTAGAAGGA TTTTAAAAGT CCATGCTAGG
        rat  TGTTATAGGC TACCTTTTGC AACAG.TGTT GCCTTAAAGT CCCAGCTAGT
      mouse  TGATCTAGGC TACCTTTTGC AACAG.TGTT GCTTAAAAAT CGCAGCTAGT
    chicken  TAGCTTGCCG AAAGTATTCT CATTGCTTTG GTCCAAATCT TTAACAAATG 701                                                       750
      human  CAGAGGCAGC CCTTTCTGCC CCTTTCTGTT CTCAGTTTAT TAGGAAATAG
        rat  CAGAGACA.. .......GGC CCTTCCTCAT CTCAAGCCCT TAGCTAATGG
      mouse  CAGAGACA.. .......GGC CCTTCCTTAT C.CAAGTCCT CAGCTAATGG
    chicken  CAAAGTGTCT CCTTAAAAAC ACTTTCCCTA TTACAAATGA CTGCTCTTTC 751                                                       800
      human  CCTGAAATTC CAGCATGATA GCAA...CT. ....GGCATC CGTCTGTGAA
        rat  ACCCAAAGGC TAGCCTGACA GGAAGAGCT. ....GGCATC TTCTGAGGAA
      mouse  CCCAAAAGAC TAGCCTGACA G...GGGCT. ....GGCATC TTCTGAGGAA
    chicken  AGTTTTCACT CTGCCTCTTG GATGTTCCTG TGAAGGCCAG GGCCTCTCTC 801                                                       850
      human  TGTGCAAACC ATGCCTGCAT CTGCCCATTA CCCGTAGCTC AGTGTCTCTG
        rat  TGTGCAAACC ATGCCTGCGT CTGCTTCATG ACACTAGCCC AGTG..TCTG
      mouse  TGTGCAAACC GTGCCTGCGT CTGTCCCATG ACACTAGCCC AGTG..TCTG
    chicken  TCTTGTTTGA ACGTGTGCTC TTCCTGACAG AGGGTGTCTG TCCCAGGCAC 851                                                       900
      human  GGCATTTCTG CAGTTGTTCT GAAGGCTTGG CGTGTTTATC TCCCACAGGC
        rat  GGCATTTGAG CAGTTGTTCT GAGGGCTCAG GATGTTTATC CCCATAAGCA
      mouse  GGCATTTAAG CAGTTGTTCT GAGGGCTTAG GATGTTTATC CCCATAACGA
    chicken  GCTTTTCTTG CTGCATTTTA GCAAGTTCTG CAGTGTTTAT CTTACACAGC
```

FIG.12C

```
        901                                                    950
human   GGCTGAACCG CTCCCGTTTC ATGAGCAGAC CAGTGGAATG CAGTGGAAGA
  rat   GCTGAACTGC CTCCTGTTTC GAGAGCAGAG CAGAGGAATG CAGTGGAAGA
mouse   GCTGAGCTGC CTCCTGTTTC GGGAGCAGAA CAGAGGAATG CAGTGGAAGA
chicken TGAAAGTCTC CTCCTGTTTC ATGAGCTCTG CGTTGGAATG CAGTGGAAGG 951                                                   1000 CArG B
human   GACCCAGGCC TCCGGC..AC CAGATTAGAG AGTTTTGTGC TGAGGT|CCCT
  rat   GACCCAGGCC TCTGGCCACC CAGATTAGAG AGTTTTGTGC TGAGGT|CCCT
mouse   GACCCA.GCC TCTGGCCACC CAGATTAGAG AGTTTTGTGC TGAGGT|CCCT
chicken GACTGAGGGC .CTGTCGACC CAGATTAGAG GTTTTTGTAA TAAGGT|CCCT 1001                                                  1050 CArG A
human   ATATGG|TTGT GTTAGACTGA ACGACAGGCT CAAGTCTGTC TTTGCT|CCTT
  rat   ATATGG|TTGT GTTAGAGTGA ACGGCCAGCT TCAGCCTGTC TTTGCT|CCTT
mouse   ATATGG|TTGT GTTAGAGTGA ACGGCCAGCT TCAGCCCGTC TTTGCT|CCTT
chicken ATATGG|TTTT GTTAGAGACT TCGGCTCTGT CTCTCTCATC TCTGCT|CCTT 1051                                                  1100
human   GTTT|GGGAAG CAAGTGGGAG GAGAGCAGGC CAA.GGGCTA TATAACCCTT
  rat   GTTT|GGGAAG CGAGTGGGAG GGGATCAGAC CAGGGGGCTA TATAACCCTT
mouse   GTTT|GGGAGG CGAGTGGGAG GGGATCAGAG CAAGGGGCTA TATAACCCTT
chicken GTTT|GGGAGG CTGGTGGGAG GAGAAGAGCT GAAGGGGCTA TATAACCCTG 1101       1118
human   CAGCTTTCAG CTTCCCTG
  rat   CAGCATTCAG CCTCCCC-     EXON 1
mouse   CAGCCTTCAG CCTCCC--
chicken GTGCTTTTGG ATACAC--
```

FIG. 12D

```
                1                                                              50
    human   -GTAAGTGCG CCAGGCCAAG GATGTGACTT ATAGATTCCA GTGGCTCTTT
      rat   ---------- ------GTAAG GATGTGACTT AGAGTTTTCC CAGGCT.TTT
    mouse   GTAAGTAGCC CCAGCCCAGG GATATGACTT CGAGTTTTCC CAGGCT.CTT
  chicken   ---------- ---------- ---------- ---------- ----------

51                                                             100
    human   TAATTACCCG GTATAATAAG ACACCATCTG CAGGGATTTG GCTGGGTTCA
      rat   TAATCATCCA GTGGAACCAG ACGTTGTCTG TAGTAATCTG AATGACTCAC
    mouse   TTATCATCCA ATGTAGCCAG ACATTGTCTG TGGGAATCTG AATGACTCAC
  chicken   -------GTA AGTGGCACTG AACCAATAGT GGGATTTATA GTTTTCTGGA 101                                                            150
    human   TGCACTGATA TTTCTGAATG AAGA.TTGTA CTACTAAAAT GATTGTAGCT
      rat   ATGTTtGGAA TTTGGGAATA AAGATTTATG CTGTTAAAAT GATTGTAGCT
    mouse   GTGTTTTGAA TTTTTGAATA AAGATTTATA CTGTTAAAAT GATTGTAGCT
  chicken   TGACTTTAAT TAAGTAATGT CACATGGAAG CTATTCAGGA GGATGTACTG 151                                                            200
    human   .TTTG.GCTT TAATGATCTA ACGTTAAAGA CAGG...... ...GCTAATAT
      rat   CCTTA.GCTT GCATGATTTC GTATCTAAAC GGG....... .ACTAAAAAT
    mouse   TTTTA.GCTT GCATGATTTT ACATCCGAAT AGGGCTGATT TACTGGAAAC
  chicken   CTATGCTGCA GTTTGCTTAG GCATTACTTA CTAGAACTGA ATTGGTAAAA 201                                                            250
    human   GTAGTTTGGT ATGATGGAAG GGGTAGAGAA GA.ATATGAA AATTTTATTA
      rat   GAATCGTGGT TTACTGGCAA AGGAGATGGA GAGGAAATTA AAGTTTGTTC
    mouse   AACGCTTGAT TTACTGGAAA AGGAAATGGA TAGAAAATTA AAGTTTGTTC
  chicken   TACTTTCAAT GTCTACACTG AGTTGTATTT GTTTTAAAGC ACTTTTGAAT 251                                                            300
    human   ATGCATGTCT TCTGTAAAA. .TGTTCATCC TAAACAAACA GCCCAGATCT
      rat   ATGCGTGGCA TCTGTGAAAT CTGTTTACAC TAAACCAACT GCTCGGATCC
    mouse   ATGTGTGTCA TCTGCAAAAC CTGTTTACAC TAAACCAACT GCTCTGATCC
  chicken   GGGAAATACG TCTGATGATT TTGCCGATTC CACCAACACT CCAACGGTAA
```

FIG.13A

```
             301                                                     350
   human     TGCAGCACAA TACAGGTATG CAGGTTAGCT GTGTGCAGTA AGTTATAC.A
     rat     CGCAGCCTAC TATAGGGGAG AAGTCCAGCC ATCTATGGTA AATTATAC.A
   mouse     CGCAGCGTAC TGTAGGGGTG GAGTCTAGCT GTATGTGGTA AATTATAC.G
 chicken     TATAAAGACA CAGACTGTTT AATGGCACAG CTGGAATTTA AGAGAACCTG 351                                                     400
   human     TTTATTTGTA TTTAGGCACT GGAAACTCAG ATTTCTTTCT GGTTCTGATT
     rat     TTTGTTTCTA CTTAGGTGTT GGACACTTGT GGATTTGTCT ATGGTTCA.G
   mouse     TTTGTTTCTA TTAGG..... CAAAAGTTGG AAACTTTTGG ATGTATCATG
 chicken     TGTGCCCCTG TGGAGTTAGC TTTGGACAGA ACAGAGTTCC TGAATGGGTG 401                                                     450
   human     TGTTGTAGGG GTTTTCTTTC ACTGGGCTGT ATTTTTGGTG CAGCTTAGGT
     rat     ACTTAGTGTG AGGACTTTCC ATCTGACCG. ......ACTA CAGCCGGGTT
   mouse     ATGTAGCATG AGGTATTT.. .......... ......AGTG CAGCTGAGGT
 chicken     AATTTGCACA CTGTGTAGTG GTTTCTCAGC AGCTTTGCTT CAGTGCTCTC 451                                                     500
   human     GTCTGGAAGT CGGA.TTTTG GAAGTGAACA GAAGAATAGT TGCCTAGTCT
     rat     AACTGGAACT .GGA.TGTCA GGAGTGAACT GGCG..CGGT TGCCTGCGCT
   mouse     AACTGGAAGT .GAA.TATCA GGAATGAACT GAGG..TAGT TGCCTGCTCT
 chicken     AAAATCAGCT TAAATTGACG TAAGTGTTTT GGAGTGTGAC TGCAAGAAGA 501                                                     550
   human     TTGATTGTGC CTGAATTTGT GTATTCCCTT CTGGTTTCCC ...TGCTCTAA
     rat     CTGGTTTtGG CTGAGTGGAC TGCGTTGCCT CTGGGTTTCC GGGGCTCTAA
   mouse     CTGATGTTGG CTGAGTGGAC .GCATTGCTT CTGGGTTTCC GGGGCTCTAA
 chicken     GCTGGAAGAT GCAAAATAGC AGTATCTAAT CAGATGCAAT GAGGATGCAT 551                                                     600
   human     CTGGTAGTGT CTTTTGTTGG AAATGTATAT CTCTTTTTTG TTGGAAATGT
     rat     CAG....... .......TAG ACATGTATAT CTT....... ..........
   mouse     GAGCTGGTGT CCTATGCTGG AAATGTGTAT CTTGT..... ......GACT
 chicken     GTGTATTCAT TGCTGTCTCG ATAGATATGA AAGCTGTGGT CTGCAAAACG
```

FIG. 13B

```
          601                                              650
human   GTATGTGTGA CCTTACAAGT TTGGATCTAC ATCATTGGTC ATTTGCAGC.
  rat   ......GTGC CCTTACGA.T TCAAACCTAT GTCATTGGTC ATTTGCAGC.
mouse   GTGTTGGTGC CCTTACAA.G TCAGACCTAT GCCATTGGTC ATTTGCAGC.
chicken CCCAATATTT TATTAAAGAT CACATTATAC ACAGAGTTCC TTGTGAGGCT 651                                              700
human   AGAGCGCAGC AGGTGACCTG CTGAATTTTT CTCTGGAAAG AAAGATTTAG
  rat   AAAGCATA.. .........G CTCCTCTACT CTCTGCAAAG AAA.......
mouse   ATAGCATA.. .........G CTTTTCTACT TTCTGCAAAG AAA.......
chicken GGAGTTGTTC TCCTGATAGC ATGCTGTAGA GGCTGGGGAA GTGATTGGTT 701                                              750
human   GGAGCAGAGC CTGCATCTGA CAGCTGTGTG TCCTCCCGGC CGGATATCTG
  rat   .......... ........TG AGGAAGTGTC TCATTCGGGA AGGATCT...
mouse   .......... ........GG AGGAAGTGTC TCATCCAGGG GAGATCT...
chicken GTCTTTCAGT GTAAAGCAGG TAGAAGTAAG AGGCTAAATA CTGTATTAAT 751                                              800
human   GTTGCATCTC CCTCAGCTTA AAGCTCCCTT CAGCCTGGTG AGGCAAGTGT
  rat   GA.TTGCGTT TCTCTGCCTC AAGTGTCCCT CTGGCCCCTT A.......G.
mouse   GATTTGCATT TCTCTGCCTC ACGTGTCCCT CAGCCGCTTA A.......GT
chicken TGCTGGGGTG AATATGTCCT TTATTCTGCA GTGTGAGTGA CTTTTGCTGC 801                                              850
human   GACTGTGCAG CCAGCCCTGC CAACCCAGGC TGAGTTTCAC TGCAAATCAA
  rat   ....GCAGAa TCTCTGTGGG AGCCACC... .......C.. ...CACTCAG
mouse   ATCTGTGGAA CCAGCCTTGC CACCCCA... .......CAT TGTAACTCAG
chicken TGGAGGATGT TACTACTGCA TGCCATGGCA GTCCTTGAGC TGTAACTCAC 851                                              900
human   GGTTTGGCAG CTTCAGCCCA G.ACTGGAGT TTTCATGCTG AGATTTTCCT
  rat   GACTTGGTAa CTTCTGCAGG GAAACGGAGT TTTCTCGATA AGATTTTCCT
mouse   GGCTCGGTAG CTTCATCAGG G.AATGGAGT TTTCTCGATA AGATTTTCCT
chicken TCCTTGGAAG AGAGTGTCCT GCCTGAATGA TTTAGCTTTG ATTTTTAGC.
```

FIG.13C

```
            901                                           950
human   AGCATTTTGT GTTTCATGGA CTAAATATGG TTTGTGTTTC AAGACCAATG
  rat   CCCcTTTTGT GATTCAT.GA CTAAATATGG TTTGCGTTTT GAGACTCACA
mouse   CCTGTTTTGT GATTCAT.GA CTAAATATGG TTTGC.ATTT GAGACTCATA
chicken ....TTTTTG TGCTCTATTA CTAAATATGG TTTTC.ATTA GAGTCCTCCA 951                                          1000
human   AGCT.GGGAA CTGTACTGTT CTTTC..... ..........C CCTCCCATCA
  rat   AACTGGGGAA GGTTACTGTC CTTTCCTCCT CCCTCCCCTC CCTCTTACA
mouse   AGCT.GGGAA GGGTACTGTC CTTTCCTCCC TTCCCCCCTC CCC.CCAACA
chicken AGCTAGAAA. ...TGCAGCC TTTTCCAGCT CCCTCCTCTC CCCTCCCCCA 1001                                          1050
human   ACTCATTTTT GGCACAAGAC GCACTCTAGT CAGTTGGAGC AAA..CCCCT
  rat   ATTCATTTTT GGCACAAGAT GAGCTCCACT GTGCTGCACC AAACTCCCCG
mouse   ATTCATTTTT GGCACCAGAT GAGCTCCACT GGGCTGCACC AAACTCCCCG
chicken AGTGATTTTT GGCATTGCAT TCTCTGCATT G.GTTTGAGC AAACCCCCTG 1051                                          1100
human   GACCCGGGTG CAGTTCCAAA AGCAGACACT CGAGC...... GTGTTTTACC   INTRONIC
  rat   GCCTCGGGTG CAGTTCCAAA AGCGGACGCT GGAGCCCAGT GTGTTTTACC    CArG
mouse   ..CCCCGGTG CAGTTCCAAA AGCAGAGGCT GGAGCCCAGT GTGTTTTACC
chicken ACCTCGAACT CTGTTCCAAA AACAGACGGT TG....GAAA GCATATTTCC 1101                                          1150
human   TAATTAGGAA ATGCT..TTG CTCCAAACCG AA.CTGCTCA TTCAGGTTAG
  rat   TAATTAGGAA ATGCTCCCTG CTTCAAACTG AAGCTGCTCC TTCAGGTTAG
mouse   TAATTAGGAA ATGCTCCCCG CTTCAAACCG .AGCTGCTCA TTCAGGTTAG
chicken TAATTAGGAA ATGGTTTC.. ..TCTAAACC ACTCTGTTCA TTCATGTTAG 1151                                          1200
human   AGAGGAGCTG TAAACCACTG AGCTCGACTC TTTCCGGGGA CACAGTGACT
  rat   ATAAGAGTTG CAAACCACAG CGGCAGTTTC .CTCTGGAAA CACACCGACG
mouse   ATAAGAGTTG CAAACCACAG CGGCTGCGTC .CTCTGGAAA CACACAGACT
chicken ATAACAATTG TACTCCATAG ACTAAATGCT TAAATATAAA GAGCCTGTTT
```

FIG.13D

```
              1201                                                    1250
    human   TCTTCAATGA CAGTGCTCCT TTTGGACATT ATAACATTCT TCCTAGATTT
      rat   TCT....... ......TCTC TAGTGACGAC GCTCCTTTCA AAGCTTATTA
    mouse   TCT....... ......TCTC CAGTGACAAG CCTCCTTTCA GAGCTTAATA
  chicken   TCCCAAAAGT TTAAGAAAGT GCGAAAAATT GCAACCTACT TTCCTTTTCT 1251                                                    1300
    human   TC..TTTTTC TTTTTCTTTT TTTTTTGGCC AAGTAAAAAA CATTTTTCTG
      rat   AG..ACA..T ATTTTCTGGA TATTTTGGAT GAAGTAGAAA TACGTCTTTA
    mouse   AG..ACAATT TTTTCCTGGA TATTTTTGAT GAAATAGAAA TACATCTTTA
  chicken   GGTAATAATG ACTTAATATC TGGAGTACAT CAACGTGGGA TTTCCCTCTC 1301                                                    1350
    human   CATTCTTGCT GATGCTGAGG GCCAGTCTCC TTTTTCTGAG TATAGTCAAC
      rat   CTGAATTAG. ..TGATTTTT ACTTGCATTT TAAAAAAAAA CTAGGAAGCT
    mouse   CGGAATTTGA CAGTATTTTT TCCTGCATTT TTTTAAAAAC CAGGGTAGCT
  chicken   CATGCCTTCT CCTGGCAGCT AC.TGTATCC ATCGAGAACT GCAGCCTGAG 1351                                                    1400
    human   CCCTCCTCCC AAGCCATCAC TGCCCAACAA AACAGTTATT AAAAATATCC
      rat   TATTTCTCTG AATATACTAA GGCACAACCT TAAGTCATCC TGCCCAAC..
    mouse   TATTTTTCTG AATATACTAA GGCACAACCT TAAGCCATCT TGCCCAACAA
  chicken   AAGCAGTCCA CAGCTGCGTG CTCGTGGCTG TGAAGGGTCT GCAGTGAGAG 1401                                                    1450
    human   CACATTCATG GTAACCATAC CTTC...... ..CCATTTTC AGAGACCATC
      rat   ..AGTTTATG TGGGTTATCC TTCC...... ..CCGTTTTC AAAGGGCATC
    mouse   AAAGTTTATG TGGGTTATCC TTCC...... ..CCATTTTC AGAGGGTATC
  chicken   GCGTTTGGGG GAGGCTGTCC CTCCTAGGTC CATCTATGGT GGAGGCTGAA 1451                                                    1500
    human   CTAATTTGAA ATGTTTTATC CTCTTTTCAG CCCTTACTTT TGGTTTGGAA
      rat   CTAATTCCGA GTGGTTTATC TCATTTGCAG CCCGGATGCT ATGTTTTGGA
    mouse   CTAATTCCAA GTGGCTTATC CCATTTGCAG CCCTGGTGCT AAGTATGGAA
  chicken   GCGTTGCCTC ATGCTCCCAT GCTCAATCAG CCATGGCTCT CACTGACGCG
```

FIG. 13E

```
              1501                                                  1550
    human    AATGCACTTA GCACATCCAT AGAGTGCCTG CTTATCCCCT GGGGCTGGCT
      rat    CA.....GCA GGCTTCCTGT AGACTCTCTG CTGGTCCTTT GCTGCTGGCT
    mouse    AACAGGCTTA GTGGACACAC AGACTCTCTG CTGGTCCTTT GGTGGTTTCT
  chicken    CACTGCCGCT TCGACGTGCA CGCCAGCAGG CCCATGGCAG CAGGTTTTGA 1551                                                  1600
    human    GCTTCTGACA GATACCCCAG GCTCTTAGGC TTCTTCCCTT TTTTCTCCTT
      rat    GCCTCTGCCA aTCACC.... ......TGGC TGCTGTGCCT CTCTGTGCTT
    mouse    GCCTCTGCCA GTCACC.... ......TGGC TTCTGTGCCT CCTTGTGGTT
  chicken    TCGTTCGCGA GGAGCCAGCT GGGCTGCTGG ATGACAGCCT GTCTCGCTTT 1601                                                  1650
    human    TATAGTTCTC GCCTCTTTTC TAAAGCTTCT TAATCTGCTC TGAGGGAAGC
      rat    TGAGACTGTC TTCTGAGTCT TTATCGTCC. .ACTGGAAAG GAAGCTAAAT
    mouse    TGAAACTTTC TTCTGAGTCC TTATCATCC. .ACTGGAAAG GAAGCTAAGT
  chicken    GGCTGTTAAC ACATTGCAAT TTGTTGACCT CTGCATGGAA GTCCAGGCTC 1651                                                  1700
    human    CAAATCACAG GAATGCCAAA ATAATTCAGC ATCTGGAAAG GGAAAAGAAG
      rat    ATAAATTCAG TGTCTGAAAG AAGAGGCAGA GTAGAGAGAG GAAAGAGCAA
    mouse    ATAATT.... .......... CAGAGGCATA GTGGAAAGAG GAAAGAGCAA
  chicken    CCAGCTAGTC GAGTGATTCC CTAACACACT ATAAATTGTG GGCAAATAGT 1701                                                  1750
    human    GGTGGGAAAG GAAAGGGCAA GCCATTCATG AGTCCCATGT CCATTCTTGC
      rat    ACCAACCAAG ATCCCATTTT TCCGTTCTTG TGAGGGGAAC CCAGGCATTG
    mouse    ACTGCTGAAG AAAGGGATTT TCCCATTCTT GCAAGGGGA. ..ACACATTG
  chicken    TCTCCTCGAG TGCTGGTATT CGGGGCTTGT TTCCGTAATT GACTTTAATA 1751                                                  1800
    human    AAGTGGAATC CACACGTTGA TTATTTTTAT TCTAAGCCTG GAGCAGTGTG
      rat    AA...GATTT CACTCTGATT TTGGAGGCAG GGTTTGAAAG GAAACCAAAA
    mouse    AA...GATTT CACTCTGATC TTGGGGACAG GG.TTGAAAG AAAACCAAGA
  chicken    CAAACCCTTT AAAGCATTTT TATTACCCTT GTTATCTTCC TGTTGCCTGA
```

FIG.13F

```
         1801                                              1850
human    GAAAGAAAGC AAAGGTTAGA AACAAAGAGT TCTGG..... .ATACTGAAA
  rat    TCACAAACAG AATCTCTGGG TAAAGACAAT AGTCA..... .CATGGTGAG
mouse    TCGCAAACAG AATCTTTGGG TAGGGATAAT AGTTA..... .CTTGATGAT
chicken  GGAGAAAAAC AATTTCTGTT TTAGTGAAGC AGGGAGCCAG CATAAATTAC 1851                                              1900
human    ATAATCACAC AGTGATAGTA ATAATAATGA TGATGAAATT AGTATTTATT
  rat    ATCGACAAGC AATGCTTGT. ACAATGCCCT TGATGTCCCC cGAAGCTGTC
mouse    ATCCACGCGC AATGCTTGT. CCAACACTCT GGATGTCCTT TGAAGCTCTC
chicken  TTTGTCATTC TACAAATGCA GCTTATTAGC TGGTTTGAAA TGATGATGGA 1901                                              1950
human    GAGAACTTAG AGTATCTCTG CCACTATAAA TTATTTTAAA CACTTTAAAA
  rat    GAAAACACAA GCTTAAATGT CAATTACTTA AAATGCTATT TTA...AGCC
mouse    AAAAATCCAA GCTTAAATGT CAATTCCTTA AATTGTTGTT AAAAACAACC
chicken  GCACACACTA TGGACAGTTT CAAAACACAT GCTGTCCTTG ATTGCATTTT 1951                                              2000
human    AACCCAATCT CTATAAGAAC TCCATGAGGT ATGTCCTGAT ATCATTACTG
  rat    CAAAAGAGTA TGTGCTCAGT TAGTCAAGGT TAGAAGAAAT ACCAGAACTC
mouse    CTAAGGGGTA TATACTCAGT TAATCAAGCT TAGAAGAAGA TACCAGAGCT
chicken  AAAGTCAGGA TATCATCTTT CTACGTGCAC CAGTCTTGTC AGGATGATAG 2001                                              2050
human    TTTTATAGTA AGGAAATTGT GGTTTAGAGA TGTTAAATAA CTGAAATCAC
  rat    AGGGGAGGAA AAAATATtTA TAAAACCTGA TACTTGCCAC TTCCAAAGAA
mouse    CAGGGAAGAA AAAAAGTCTA CAAAAGCTGA TGCTTGCCAC TTCAAAAGAA
chicken  AGGCAGGGGA CATCATACTG AATCTGATGC AAAGAGACCT TTGTTTTTGC 2051                                              2100
human    ACAGCTTTTA ACTGTTGGAG .CCTGGACTC AAATCCAGGC TTTCTGACTT
  rat    CCCCAGTAAA TATTTTGGAG AGAATAAGTA AGCTTTGGGG GTGAGGGAGT
mouse    TCTAGTAACA ...TTTGGAC AGAATAAGTA AGCTTTGGG. .........TA
chicken  AGCTGTCAGT CCAGCAGTCT TCTTTATCTC CCACCTACGC CTCAGTGGTG
```

FIG. 13G

```
                  2101                                                    2150
        human  CAGAGTCTAA GCTCATAATC ATGTGATCTG AAATCTTCGT TGTCCTAAAT
          rat  GGGGGGCAAT TCACTTTTTA TTACGGTCAT ATTAAGTTTC TTTCTGTAAC
        mouse  GAGGAACAAC TCACATTTTA TTAAGGTCAT A.TCTGTCTC TTTCTGTAAC
      chicken  GATTTCCGTG GCCGAATTTA .GATAAACAT TCGCTGTCTC AAAGCTGTAA 2151                                                    2200
        human  GTATCAGTTC AAGGCTCTTG GACAAGTCAC TTCAACTCCT TAAGCCTTGG
          rat  TTATCAGTCT TAAG..TAAG AATAGCTATT ATCATCCTGT TGGGTTTTCA
        mouse  TTATCAGTCT TAAA..CAAG AATAGCTCTC AGCAACCTGT TGGGTTTTCA
      chicken  TGATCTGTCT TTCCATGCAG CAGGACTGGA ATAGTTCCAT GGAGTACTTT 2201                                                    2250
        human  TTTCCTTGTC AGCTGAAGAT AATATTACAT GCCTTGACTT TAAAATATGT
          rat  GCTTAGCAGT GATTTTGATT AATGAGGAAA TGTTGTAAaT CCTAAAATTG
        mouse  GCTTAACAGT GACTTTAATA AATGAAGAAA TGTTATAACT CGTAAAATTT
      chicken  GAATTATGTC TGGTGCATAC AGCCTTCCTG CCTATCAGTT CCTTTTATAC 2251                                                    2300
        human  CATCTCAATT GCAGTTTTAT GTTCTTTGCA AAGAGTTATT TTACATGAAG
          rat  CAAACTCCCC CATCAAAAAT TTtCAATCCA ATATTtTTTA CTAGAGTAGg
        mouse  CAAAC.ACCA TATTTGGAAA TTTCTATCCA AGTTTCCATA TTAGA.....
      chicken  CGCATTCTCT GTCTTACAGG GTGGTTCTGG TACCTCACTT TGTTGTTTTT 2301                                                    2350
        human  CACTGCTAAG GAAGTTTTAG GCCTTTGGCA AGATGCAGGT TTGATTTTGT
          rat  ACTTGgTAGC CTTTCAACTT GTGATCcTCC TGCCTCAGCT TCCCAAGTGg
        mouse  .....CCAGC TCCTTAACTT GTGATCCTCC TGCCTCAGCC T.CCAAGTGC
      chicken  TTTTCAATTA TTCTTTTCTT GCTGTTTCCA TAG--------  ----------

2351                                                    2400
        human  GGGAATGTTT TGGCAGAACT CCAACTC... ..TGTAATAG CTATTTTATT
          rat  TAGGATCACA GGTCTACATC ACCACGCCCA GTCTTGATTC ATGTCTAATG
        mouse  TAGGAT.ATA GGTGTACATC ATCACACCCA GCCTTGATTC ATATTTAATA
      chicken  ---------- ---------- ---------- ---------- ----------
```

FIG.13H

|         | 2401       |            |            |            | 2450       |
|---------|------------|------------|------------|------------|------------|
| human   | TCCCTACTTC | TCAGATGTTT | CCTTAAAAGA | ACTGCCTTTT | TTATATGGAT |
| rat     | CCACACCAGC | ACCcAAGTCT | TCAGAGACAA | AAGATTTTTC | TTTTAAACAT |
| mouse   | CCTCACCGGC | TCACAAGTCT | TTAGAGCCAA | AAGTTTTCTC | TTTTAAACAT |
| chicken | ---------- | ---------- | ---------- | ---------- | ---------- |

|         | 2451       |            |            |            | 2500       |
|---------|------------|------------|------------|------------|------------|
| human   | TTGGAGGTGC | AATCAGTTAA | CCCATTTAGA | AGAAGAAATT | TTCTCAATTT |
| rat     | TTAATATGAG | CAAACATTTT | AACATTCTCA | TATGCTGCCC | ATTATTCCAA |
| mouse   | TTAATATGAG | TAAACATTTT | AACATTTTCA | AATTCTCACA | TGCTGCCCA. |
| chicken | ---------- | ---------- | ---------- | ---------- | ---------- |

|         | 2501       |            |            |            | 2550       |
|---------|------------|------------|------------|------------|------------|
| human   | GAAATCCTAA | TTGAGATCTC | AATGCCAGGC | AGATAACTCT | GGGTGTCCTT |
| rat     | AATCTACCTT | TTTGGGGGAA | AATATATTTT | ACCAAAAAAA | AAAGTGACTT |
| mouse   | .......... | .......... | .......... | .......... | .......... |
| chicken | ---------- | ---------- | ---------- | ---------- | ---------- |

|         | 2551       |            |            |            | 2600       |
|---------|------------|------------|------------|------------|------------|
| human   | CTCTTAACGG | AACATTTCGA | CCTAATTGTG | ATTAGAAAAG | TGGAAGAGGT |
| rat     | TGGTTTGATA | TAGATAACAA | ACCTTGGTTT | GATATAGATA | ACAAACCTTT |
| mouse   | .....TTCCT | TGAAAATCTA | CCTTTGGTGG | GGGGGGGGGG | GGGACTATAT |
| chicken | ---------- | ---------- | ---------- | ---------- | ---------- |

|         | 2601       |            |            |            | 2650       |
|---------|------------|------------|------------|------------|------------|
| human   | CTTGAACTGG | AAGCCAAGGG | GTGGCTAAAG | AGTACCT... | GATGTCTGGC |
| rat     | CTAGATAGTT | CTTTAACATG | TGgTATCACT | ATTCCCTATA | GACCTGTGTT |
| mouse   | ATATATA... | .......... | .......... | TGTCCCTATA | GAACTCTGCT |
| chicken | ---------- | ---------- | ---------- | ---------- | ---------- |

|         | 2651       |            |            |            | 2700       |
|---------|------------|------------|------------|------------|------------|
| human   | TGGAGCTCTC | CTCTAATGCC | CTGTGTGCCC | TTGAGCAATC | ACTTCCTGAT |
| rat     | CTCCACTCAG | GACCTCTCAT | CTGTGCTCTG | TGGCCTGTTC | ACACACTAAT |
| mouse   | CTCTACACTG | CATCTCTCAT | CTGTGCTCTA | TGATCTATTC | ACACACTAAT |
| chicken | ---------- | ---------- | ---------- | ---------- | ---------- |

FIG. 131

```
         2701                                                   2750
human    TTTCTTATTT G..TGAAAAT GAGAGCATTG GATGAAAATG TCCTCTAATA
  rat    GCTCTGCCCT GCTTGAGAGT GgTAAAAGAG CCTGTGA.GC TCCTGCTCTT
mouse    GCTCTGACCA GCTTGAGAGT GTTATAAGAG CCTGTGACAC TCCCGCTCTT
chicken  ────────── ────────── ────────── ────────── ──────────

2751                                                   2800
human    TGCCTTCAAT TTCTCAAATT TGTAAGTTGA TAGGCTGCTC CAGCCTTTCT
  rat    TGTGCTGAGG GCTTGTGGTG CTAACCTGGA AGTCAGGGTT TCAGCTCATC
mouse    TGTGCTGAGG ACTTGTGGTG TTAACCTGGA AGTCAGGGTT TCGGATCATC
chicken  ────────── ────────── ────────── ────────── ──────────

2801                                                   2850
human    AATTTTATGA AAGGATCCAA GTATAAGATC CAAGTATAAA ATGG──────
  rat    AAAGGCcTTA CAGTCTGGTG AAAGCATTTC AAGATAAAGA GTGTTAGTTG
mouse    AAAGGCTTTA CAGCCTAGTG AAAGCATTTC AAGATAAAGG GTGTTAGTTG
chicken  ────────── ────────── ────────── ────────── ──────────

2851                                                   2900
human    ────────── ────────── ────────── ────────── ──────────
  rat    AGATCTGGGG AGAGCGTCCA GCTAAAATAA CACAACAGGG CCAAGAACCC
mouse    AGAACTGTGG AGAGCCTCCA GCTAAAATAA CACAACAGGA CCAAGAACCC
chicken  ────────── ────────── ────────── ────────── ──────────

2901                                                   2950
human    ────────── ────────── ────────── ────────── ──────────
  rat    TGGTTGTGGT TGGGAGTGAC CGTAGGCTCC GGCCAAACGC ──────────
mouse    TGTCTGTGGG TGGGAGTGAC ..TAGGCTCT AGCCAAATGC TCTGCGCTAC
chicken  ────────── ────────── ────────── ────────── ──────────

2951                                                   3000
human    ────────── ────────── ────────── ────────── ──────────
  rat    ────────── ────────── ────────── ────────── ──────────
mouse    AGTAGCTTCT CGCTCGCTGT CTCTGCAGAA CCCTGAGACG CTGCTCCAGC
chicken  ────────── ────────── ────────── ────────── ──────────
```

FIG. 13J

COMPOSITIONS AND METHODS FOR MODULATING EXPRESSION WITHIN SMOOTH MUSCLE CELLS

This application claims priority under 35 U.S.C. §119 (e) to U.S. provisional patent application No. 60/105,330 filed Oct. 23, 1998, which is hereby incorporated by reference in its entirety.

This invention was made with government support under grant numbers HL 38854 and HL 10038, awarded by the National Institutes of Health. The government may have certain rights in the invention.

1. INTRODUCTION

The present invention relates to promoters, enhancers and other regulatory elements that direct expression within smooth muscle cells ("SMC"). In particular, it relates to compositions comprising nucleotide sequences from the 5' regulatory region and the first intron, and transcriptionally active fragments thereof, that control expression of a smooth muscle α-actin ("SM α-A"). Specifically provided are expression vectors, host cells and transgenic animals wherein an SM α-A regulatory region is capable of controlling expression of a heterologous gene, over-expressing an endogenous SMC gene or an inhibitor of a pathological process or knocking out expression of a specific gene believed to be important for an SM-related disease in SMC. The invention also relates to methods for using said vectors, cells and animals for screening candidate molecules for agonists and antagonists of disorders involving SMC.

The present invention further relates to compositions and methods for modulating expression of compounds within SMC. The invention further relates to screening compounds that modulate expression within SMC. Methods for using molecules and compounds identified by the screening assays for therapeutic treatments also are provided.

2. BACKGROUND OF THE INVENTION

2.1 Gene Therapy

Somatic cell gene therapy is a strategy in which a nucleic acid, typically in the form of DNA, is administered to alter the genetic repertoire of target cells for therapeutic purposes. Although research in experimental gene therapy is a relatively young field, major advances have been made during the last decade. (Arai, Y., et al., 1997, Orthopaedic Research Society, 22:341). The potential of somatic cell gene therapy to treat human diseases has caught the imagination of numerous scientists, mainly because of two recent technologic advancements. Firstly, there are now numerous viral and non-viral gene therapy vectors that can efficiently transfer and express genes in experimental animals in vivo. Secondly, increasing support for the human genome project will allow for the identity and sequence of the estimated 80,000 genes comprising the human genome in the very near future.

Gene therapy was originally conceived of as a specific gene replacement therapy for correction of heritable defects to deliver functionally active therapeutic genes into targeted cells. Initial efforts toward somatic gene therapy relied on indirect means of introducing genes into tissues, called ex vivo gene therapy, e.g., target cells are removed from the body, transfected or infected with vectors carrying recombinant genes and re-implanted into the body ("autologous cell transfer"). A variety of transfection techniques are currently available and used to transfer DNA in vitro into cells; including calcium phosphate-DNA precipitation, DEAE-Dextran transfection, electroporation, liposome mediated DNA transfer or transduction with recombinant viral vectors. Such ex vivo treatment protocols have been proposed to transfer DNA into a variety of different cell types including epithelial cells (U.S. Pat. No. 4,868,116; Morgan and Mulligan WO87/00201; Morgan et al., 1987, Science 237:1476–1479; Morgan and Mulligan, U.S. Pat. No. 4,980,286), endothelial cells (WO89/05345), hepatocytes (WO89/07136; Wolff et al., 1987, Proc. Natl. Acad. Sci. USA 84:3344–3348; Ledley et al., 1987 Proc. Natl. Acad. Sci. 84:5335–5339; Wilson and Mulligan, WO89/07136; Wilson et al., 1990, Proc. Natl. Acad. Sci. 87:8437–8441), fibroblasts (Palmer et al., 1987, Proc. Natl. Acad. Sci. USA 84:1055–1059; Anson et al., 1987, Mol. Biol. Med. 4:11–20; Rosenberg et al., 1988, Science 242:1575–1578; Naughton & Naughton, U.S. Pat. No. 4,963,489), lymphocytes (Anderson et al., U.S. Pat. No. 5,399,346; Blaese, R. M. et al., 1995, Science 270:475–480) and hematopoietic stem cells (Lim, B. et al. 1989, Proc. Natl. Acad. Sci. USA 86:8892–8896; Anderson et al., U.S. Pat. No. 5,399,346).

Direct in vivo gene transfer recently has been attempted with formulations of DNA trapped in liposomes (Ledley et al., 1987, J. Pediatrics 110:1), in proteoliposomes that contain viral envelope receptor proteins (Nicolau et al., 1983, Proc. Natl. Acad. Sci. U.S.A. 80:1068) and DNA coupled to a polylysine-glycoprotein carrier complex. In addition, "gene guns" have been used for gene delivery into cells (Australian Patent No. 9068389). It even has been speculated that naked DNA, or DNA associated with liposomes, can be formulated in liquid carrier solutions for injection into interstitial spaces for transfer of DNA into cells (Felgner, WO90/11092).

Numerous clinical trials utilizing gene therapy techniques are underway for such diverse diseases as cystic fibrosis and cancer. The promise of this therapeutic approach for dramatically improving the practice of medicine has been supported widely, although there still are many hurdles that need to be passed before this technology can be used successfully in the clinical setting.

Perhaps, one of the greatest problems associated with currently devised gene therapies, whether ex vivo or in vivo, is the inability to control expression of a target gene and to limit expression of the target gene to the cell type or types needed to achieve a beneficial therapeutic effect.

2.2 Tissue Specific Expression within Smooth Muscle Cells

Smooth muscle cells, often termed the most primitive type of muscle cell because they most resemble non-muscle cells, are called "smooth" because they contain no striations, unlike skeletal and cardiac muscle cells. Smooth muscle cells aggregate to form smooth muscle ("SM") which constitutes the contractile portion of the stomach, intestine and uterus, the walls of arteries, the ducts of secretory glands and many other regions in which slow and sustained contractions are needed.

Abnormal gene expression in SMC plays a major role in numerous diseases including, but not limited to, atherosclerosis, coronary artery disease, hypertension, stroke, asthma and multiple gastrointestinal, urogenital and reproductive disorders. These diseases are the leading causes of morbidity and mortality in Western Societies, and account for billions of dollars in health care costs in the United States alone each year.

In recent years, the understanding of muscle differentiation has been enhanced greatly with the identification of several key cis-elements and trans-factors that regulate expression of muscle-specific genes. Firulli A. B. et al., 1997, *Trends in Genetics,* 13:364–369; Sartorelli V. et al., 1993, *Circ. Res.,* 72:925–931. However, the elucidation of transcriptional pathways that govern muscle differentiation has been restricted primarily to skeletal and cardiac muscle. Currently, no transcription factors have yet been identified that direct SM-specific gene expression, or SMC myogenesis. Owens G. K., 1995, *Physiol. Rev.,* 75:487–517. Unlike skeletal and cardiac myocytes, SMC do not undergo terminal differentiation. Furthermore, they exhibit a high degree of phenotypic plasticity, both in culture and in vivo. Owens G. K., 1995, *Physiol. Rev.,* 75:487–517; Schwartz S. M. et al., 1990, *Physiol. Rev.,* 70:1177–1209. Phenotypic plasticity is particularly striking when SMC located in the media of normal vessels are compared to SMC located in intimal lesions resulting from vascular injury or atherosclerotic disease. Schwartz S. M., 1990, *Physiol. Rev.,* 70:1177–1209; Ross R., 1993, *Nature,* 362:801–809; Kocher O. et al., 1991, *Lab. Invest.,* 65:459–470; Kocher O. et al., 1986, *Hum. Pathol.,* 17:875–880. Major modifications include decreased expression of SM isoforms of contractile proteins, altered growth regulatory properties, increased matrix production, abnormal lipid metabolism and decreased contractility. Owens G. K., 1995, *Physiol. Rev.,* 75:487–517. The process by which SMC undergo such changes is referred to as "phenotypic modulation". Chamley-Campbell J. H. et al., 1981, *Atherosclerosis,* 40:347–357. Importantly, these alterations in expression patterns of SMC protein cannot simply be viewed as a consequence of vascular disease, but rather, are likely to contribute to progression of the disease.

A key to understanding SMC differentiation is to identify transcriptional mechanisms that control expression of genes that are selective or specific for differentiated SMC and that are required for its principal differentiated function, contraction. Currently, studies are ongoing in which the expression of the contractile proteins SM α-A (Shimizu R. T. et al., 1995, *J. Biol. Chem.,* 270:7631–7643; Blank R. S. et al., 1992, *J. Biol. Chem.,* 267:984–989) and SM myosin heavy chain (SM-MHC)(White S. L. et al., 1996, *J. Biol. Chem.,* 271:15008–15017; Katoh Y. et al., 1994, *J. Biol. Chem.,* 269:30538–30545; Wantanabe M. et al., 1996, *Circ. Res.,* 78:978–989; Kallmeier R. C. et al., 1995, *J. Biol. Chem.,* 270:30949–30957; Madsen C. S. et al., 1997, *J. Biol. Chem.,* 272:6332–6340; Madsen C. S. et al., 1997, *J. Biol. Chem.,* 272:29842–29851), as well as a variety of proteins implicated in control of contraction including SM22α(Li L. et al., 1996, *J. Cell. Biol.,* 132:849–859; Kim S. et al., 1997, *Mol. Cell. Biol.,* 17:2266–2278), $h_1$-calponin (Miano J. M. et al., 1996, *J. Biol. Chem.* 271:7095–7103), h-caldesmon (Yano H. et al., 1994, *Biochem. Biophys. Res. Commun.* 201:618–626), telokin (Herring B. P. et al., 1996, *Am. J. Physiol.,* 270:C1656–C1665) and desmin (Bolmont C. et al., 1990, *J. Submicrosc. Cytol. Pathol.,* 22:117–122) are being examined.

Recently, several cis elements and trans acting factors have been described that regulate muscle-specific gene expression in skeletal and cardiac muscle and are required for the terminal differentiation of these muscle cell types. In contrast, the mechanisms regulating SMC differentiation are only poorly understood, and to date, no transcription factors have been identified that direct SMC-specific gene expression. Because SMC maturation and differentiation are required for the full development of arteries and veins during angiogenesis and vasculogenesis, the identification of the molecular mechanisms that control SMC differentiation are important for an understanding of these processes that occur not only during development, but also under pathologic conditions. Furthermore, it may lead to a better understanding of SMC phenotypic modulation that has been shown to contribute to atherosclerosis and restenosis following balloon angioplasty (Ross R, et al., *N. Engl J Med.* 1976;295:369–377; Schwartz SM, et al.; *Prog Cardiovasc Dis.* 1984;26:355–372).

One example of a protein which is required for contractile functions of SMC is SM α-actin, which makes up 40% of total SMC protein. Not only is it clearly required for the contractile function of SMC, but it also is the first SMC differentiation marker to appear during development (Duband J L, et al.; *Differentiation;* 1993;55:1–11). Although SM α-A is transiently expressed in the myocardium and skeletal muscle in the developing embryo, and in myofibroblasts during wound healing, SM α-A expression in adult animals is highly restricted to SMC or SM-like cells (Darby I, et al.; *Lab Invest.;* 1990;63:21–29; Woodcock-Mitchell J, et. al.; *Differentiation;* 1988;39:161–166).

Transcriptional regulation of various SMC genes has been analyzed extensively in cultured SMC and several functional cis-elements have been identified. White S. L. et al., 1996, *J. Biol. Chem.,* 271:15008–15017; Katoh Y. et al., 1994, *J. Biol. Chem.* 269:30538–30545; Wantanabe M. et al., 1996, *Circ. Res.,* 78:978–989; Kallmeier R. C. et al., 1995, *J. Biol. Chem.,* 270:30949–30957; Madsen C. S. et al., 1997, *J. Biol. Chem.,* 272:6332–6340; Madsen C. S. et al., 1997, *J. Biol. Chem.,* 272:29842–29851. However, because differentiation of SMC is known to be dependent on many local environmental cues that cannot be completely reproduced in vitro, cultured SMC are known to be phenotypically modified as compared to their in vivo counterparts (Owens G. K., 1995, *Physiol. Rev.,* 75:487–517; Chamley-Campbell J. H. et al., 1981, *Atherosclerosis,* 40:347–357). As such, certain limitations exist regarding the usefulness of cultured SMC in defining transcriptional programs that occur during normal SMC differentiation and maturation within the animal.

One example of a transcriptional regulatory element that has been implicated in the transcriptional control of various SMC genes is the CArG element. The CArG element was first described as the core sequence of the serum response element (SRE) within early response genes such as c-fos, but also has been shown to be required for the activity of many muscle-specific gene promoters (Gustafson T A, et al., *Mol. Cell Biol.;* 1988;8:4110–4119; Chow K, et al., *Mol. Cell Biol.,* 1990;10:528–538; Papadopoulos N, et al., *Mol. Cell Biol.,* 1993;13:6907–6918; Mohun T J, et al., *EMBO J.,* 1989;8:1153–1161; Lee, T, et al., *Mol. Cell Biol.,* 1991;11:5090–5100). Of interest, nearly all of the SMC differentiation marker genes characterized to date, including SM myosin heavy chain (SM MHC), caldesmon and telokin, contain two or more CArG elements that are required for maximal expression in cultured SMC (Shimizu R T, et al., *J. Biol Chem.,* 1995;270:7631–7643; Madsen C S, et al., *J Biol Chem.,* 1997;272:6332–6340; Li L, et al., *J. Cell Biol.,* 1996;132:849–859; Herring B P, et al., *Am. J. Physiol.,* 1997;272:C1394–C1404; White S L, et al., *J. Biol. Chem.,* 1996;271:15008–15017; Zilberman A, et al., *Circ. Res.,* 1998;82:566–575). In addition, it previously has been reported that a conserved CArG element in the SM-22 promoter is required for the arterial expression of a Lac Z transgene in the mouse (Kim S, et al., *Mol. Cell Biol.,* 1997;17:2266–2278; Li L, et al., *Dev. Biol.,* 1997;187:311–321). Electrophoretic mobility supershift studies demonstrated that the SM α-A CArG elements, like the SRE, bind serum response factor (Shimizu R T, et al., *J. Biol Chem.*, 1995;270:7631–7643). Although recent evidence suggests that muscle derived tissues express higher levels of SRF than nonmuscle tissues (Li L, et al., *Dev. Biol.*, 1997;187:311–321), SRF is thought to be ubiquitously expressed, and a critical yet presently unresolved question remains as to the mechanism of CArG-dependent regulation of SMC-specific gene expression.

It is now well established that SMC differentiation is dependent upon a large number of local environmental cues including extracellular matrix interactions, local production of growth factors and mechanical stresses that cannot be accurately reproduced in culture (Owens G. K., *Physiol. Rev.*, 1995;75:487–517; Chamley-Champbell J H, et al., *Atherosclerosis.*, 1981;40:347–357). Moreover, recent studies have provided clear evidence that gene regulation in SMC culture systems does not always represent regulation in vivo. Li L, et al., *Dev. Biol.* 1997;187:311–321; Madsen C S, et al., *Circ. Res.*, 1998;82:908–917. As such, when studying SMC differentiation, it is critical that regulatory pathways initially identified in cultured SMC are tested in vivo through the use of transgenic animals. For example, analysis of SM-22 and SM MHC gene expression in transgenic mice has demonstrated that expression of SMC-marker genes is complex and may involve "regulatory cassettes" that drive expression within some, but not all, SM tissues (Li L, et al., *J. Cell Biol.*, 1996;132:849–859; Kim S, et al., *Mol. Cell Biol.*, 1997;17:2266–2278). As such, transgenic studies also are critical for detecting possible heterogeneity in SMC gene regulation.

Currently, no studies have reported the complete characterization of regulatory regions required for driving in vivo expression of SM α-A during development and maturation. Although Wang et al. (Wang J, et al., *J. Clin Invest.*, 1997;100:1425–1439) recently reported that an SM α-A promoter containing 1,100 bp of 5' promoter and the entire first intron could drive expression of an IGF-1 transgene in many SM tissues, there studies were restricted to analysis in adult animals and focused on examination of the effects of IGF-1 overexpression in SMC and not on the characterization of the promoter regions required for SMC-specific expression. This deficiency of Wang et al. is critical since the SM α-A gene is known to be expressed by all three muscle types during development. Moreover, it is highly likely that over-expression of the biologically active substance IGF-1 in the studies by Wang et al. resulted in feedback alterations in the activity of the SM α-A promoter since there is extensive evidence that IGF-1 alters SMC function (Clemmons et al., J Cell Physiol, 145:129–135, 1990). As such, it is unclear whether the expression patterns reported by Wang et al. are truly representative of the inherent activity of the SM α-A promoter, as opposed to being artifactually influenced by over-expression of IGF-1.

The current invention provides the major advance of identifying molecular elements that confer SMC-specific transcription in vivo during normal development and during various disease states involving SMC-specific gene expression. More specifically, the instant invention provides, for the first time, inter alia, the identification of sufficient regions of the SM α-A gene to direct SMC-specific expression, both in vitro in cultured SMC, and in vivo in transgenic animals.

3. SUMMARY OF THE INVENTION

The invention disclosed herein provides a model for SMC-specific gene transcription. The invention is based in part on the functional characterization described herein of an SM α-A regulatory region, which is the first SMC-specific regulatory region found to be active only in SMC.

The present invention provides compositions and methods for screening compounds that modulate expression within SMC. In particular, it provides compositions comprising nucleotides from the rat SM α-A promoter and first intron, and transcriptionally active fragments thereof, as well as nucleic acids that hybridize under highly stringent conditions to such nucleotides, that control the expression of an SMC-specific gene. Specifically provided are expression vectors comprising the SM α-A regulatory region, and transcriptionally active fragments thereof, operably associated to a heterologous reporter gene, e.g., LacZ, and host cells and transgenic animals containing such vectors. The invention also provides methods for using such vectors, cells and animals for screening candidate molecules for agonists and antagonists of SMC-related disorders. Methods for using molecules and compounds identified by the screening assays for therapeutic treatments also are provided.

For example, and not by way of limitation, a composition comprising a reporter gene is operatively linked to an SMC-specific regulatory sequence, herein called the SM α-A regulatory region. The SM α-A driven reporter gene is expressed as a transgene in animals. The transgenic animal, and cells derived from the SMC of such transgenic animal, can be used to screen compounds for candidates useful for modulating SMC-related disorders. Without being bound by any particular theory, such compounds are likely to interfere with the function of trans-acting factors, such as transcription factors, cis-acting elements, such as promoters and enhancers, as well as any class of post-transcriptional, translational or post-translational compounds involved in SMC-related disorders. As such, they are powerful candidates for treatment of such disorders, including, but not limited to, coronary artery disease, hypertension, stroke, asthma and multiple gastrointestinal, urogenital and reproductive disorders.

In one embodiment, the invention provides methods for high throughput screening of compounds that modulate specific expression of genes within SMC. In this aspect of the invention, cells from SM-tissues are removed from the transgenic animal and cultured in vitro. The expression of the reporter gene is used to monitor SMC-specific gene activity. In a specific embodiment, LacZ is the reporter gene. Compounds identified by this method can be tested further for their effect on SMC-related disorders in normal animals.

In another embodiment, the transgenic animal models of the invention can be used for in vivo screening to test the mechanism of action of candidate drugs for their effect on SMC-related disorders. Specifically, the effects of the drugs on SMC-related disorders including, but not limited to, coronary artery disease, hypertension, stroke, asthma and multiple gastrointestinal, urogenital and reproductive disorders, can be assayed.

In another embodiment, a gene therapy method for treating and/or preventing SMC-related disorders is provided. Smooth muscle α-A regulatory sequences are used to drive SMC-specific expression of therapeutic molecules and introduced in the SMC. The method comprises introducing an SM α-A regulatory sequence operatively associated with a nucleic acid encoding a therapeutic molecule into SMC. In one embodiment, the invention provides a preventative gene therapy method comprising introducing an SM α-A regulatory sequence operatively associated with a nucleic acid encoding a therapeutic molecule into SMC to delay and/or prevent an SMC-related disorder. In a specific embodiment, the invention provides a gene therapy method for treatment of cancer or other proliferative disorder involving SMC. The SM α-A regulatory sequence is used to direct the expression of one or more proteins specifically in the SM-tumor cells of a patient.

The invention further provides methods for screening for novel transcription factors that modulate the SM α-A regulatory sequence. Such novel transcription factors identified by this method can be used as targets for treating SMC-related disorders.

4. BRIEF DESCRIPTION OF THE FIGURES

FIGS. 1 (A–C). Linear diagrams of Lac Z promoter constructs used to generate transgenic mice. Deletion fragments from a rat genomic clone were subcloned into the previously described pUC/AUG β-galactosidase vector (See Section 6.1. Materials and Methods for more details). FIG. 1A, Fragment from −547 to +47 (p547/Lac Z). FIG. 1B, Fragment from −547 to +2,784 (p547Int/Lac Z). FIG. 1C, Fragment from −2,600 to +2,784 (p2600Int/Lac Z). CArG A at −71 to −62, CArG B at −112 to −121, the intronic CArG at +1,001 to 1010 and the 5'-untranslated first exon are indicated. Not I/Eco RI digestion was used to remove the pUC plasmid backbone before transgenic injections.

Figure 2C:
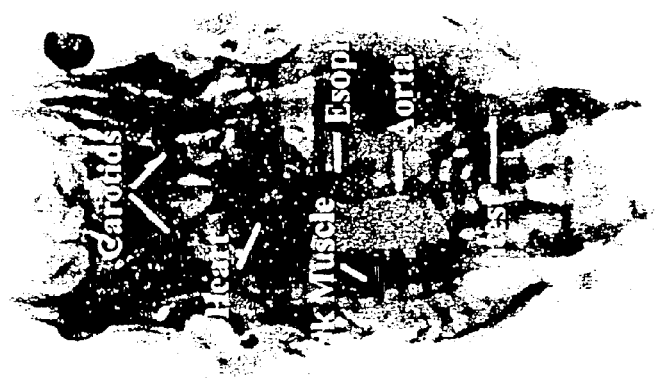
Figure 2B:
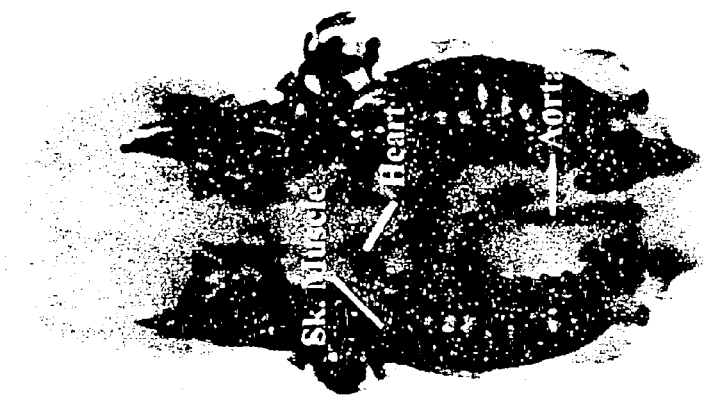
Figure 2A:
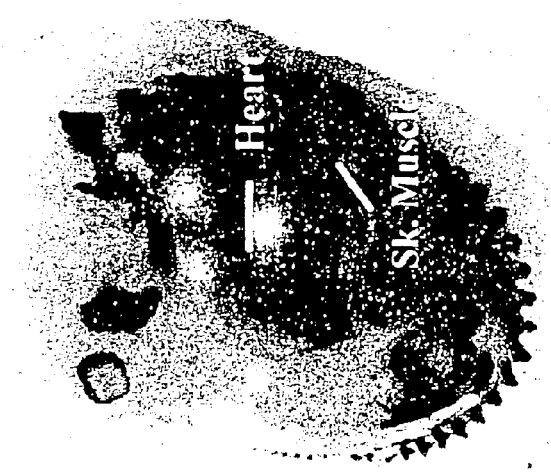

FIGS. 2(A–C). Examination of transgene expression at E13.5. The SM α-A promoter/Lac Z deletion constructs shown in FIG. 1 were used to generate transgenic mice using standard transgenic procedures. Transgenic embryos at E1.3.5 were stained for Lac Z expression and a representative embryo from each group is shown (n>4 independent founders per group). At this embryonic stage SM α-actin is expressed in skeletal, heart, and SM. FIG. 2A, The p547/Lac Z construct was highly expressed in the heart and skeletal muscle, but not in SMC. FIG. 2B, Inclusion of the entire first intron (p547Int/Lac Z) which contains a highly conserved CArG element resulted in additional, but very limited expression in the abdominal aorta and umbilical arteries. FIG. 2C, Promoter sequences from −2,600 through the first intron (p2,600Int/Lac Z) were sufficient to drive expression of the Lac Z transgene that closely mimicked expression of endogenous SM α-A with staining in heart and skeletal muscle and vascular, GI, and airway SM.

Figure 3A:
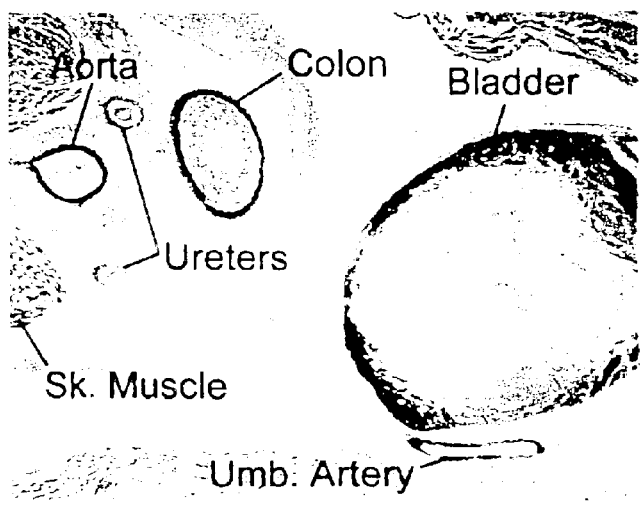
Figure 3B:
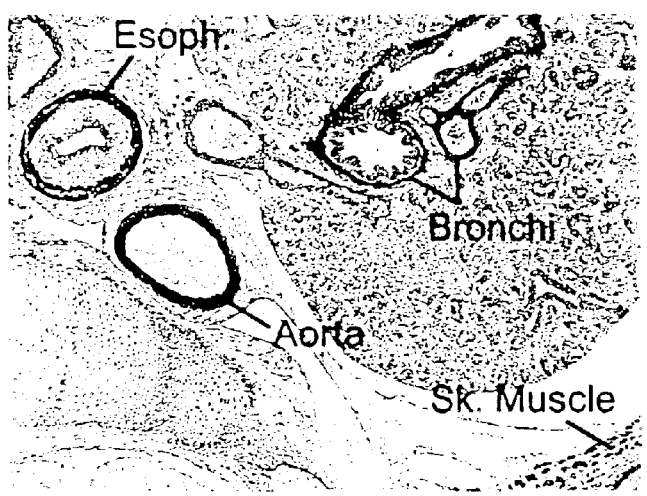
Figure 3C:
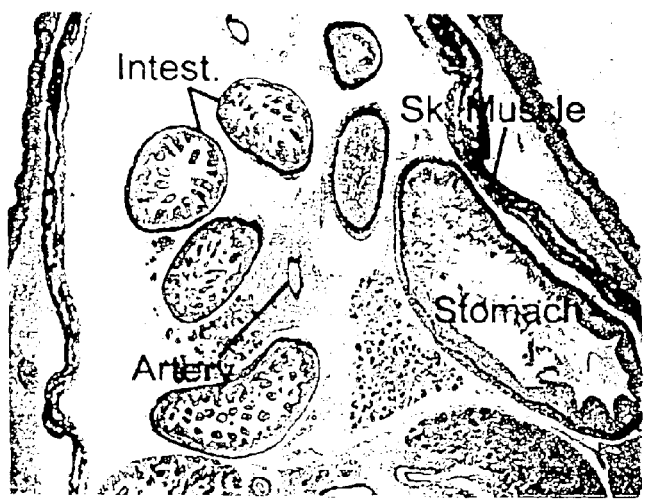
Figure 4C:
Figure 4B:
Figure 4A:
Figure 4F:
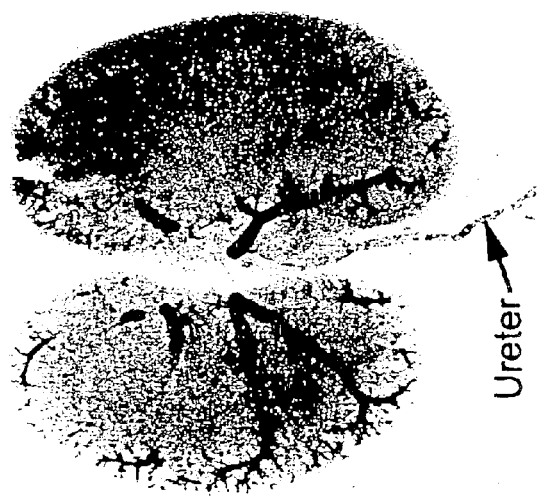
Figure 4E:
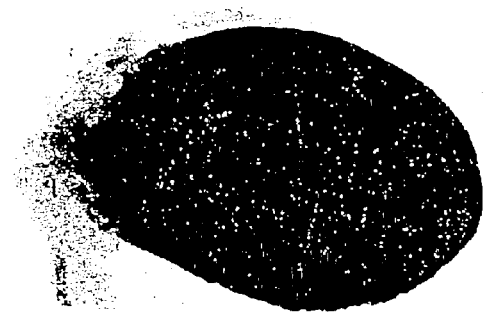
Figure 4D:
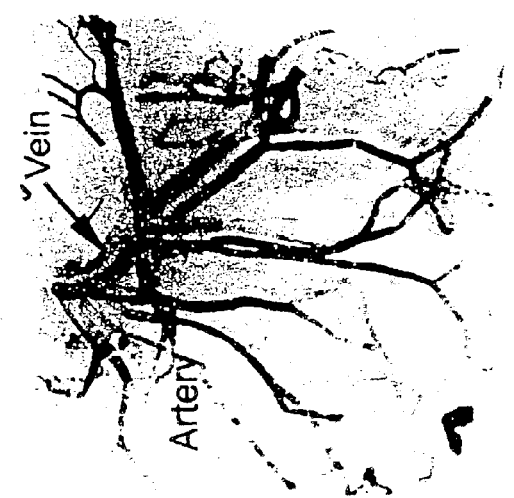

FIGS. 3(A–C). Histological examination of p2600Int/Lac Z expression at E16.5. After Lac Z staining, embryos were fixed overnight, embedded in paraffin, sectioned at 6–10 μm and counterstained with eosin. FIGS. 3A–C, Transverse sections were taken at multiple locations to obtain a representative sample of most SM tissues. Lac Z expression was seen in skeletal and cardiac muscle and in nearly all SM tissues including esophagus, bronchi, aorta, bladder, intestine, stomach, and most vascular beds. Note that staining in SM-containing tissues is highly restricted to SMC.

FIGS. 4(A–F). Expression of the p2600Int/Lac Z transgene in adult mice. Four to six week old mice were perfusion fixed and tissues were, excised, and stained over night for Lac Z expression. Expression was seen in nearly all SMC-containing tissues examined. FIG. 4A, Portion of the intestines showing uniform Lac Z staining. FIG. 4B, Anterior view of the heart showing Lac Z expression in most, if not all, of the coronary vasculature and out flow tracts. FIG. 4C, View of the stomach which has been opened sagitally to show staining of the stomach wall and the gastric artery. Lac Z expression in the esophagus was limited to longitudinal SMC. FIG. 4D, Mesenteric vasculature removed en bloc showing SMC-specific staining of both the mesenteric arteries and veins. FIG. 4E, Bladder showing very intense and uniform Lac Z expression. FIG. 4F, Splayed view of the kidney after it was cut sagitally to reveal Lac Z staining of the renal vasculature and ureter. RCA indicates right coronary artery; LCA indicates left coronary artery; Ao indicates aorta; PA indicates pulmonary artery.

Figure 5A:
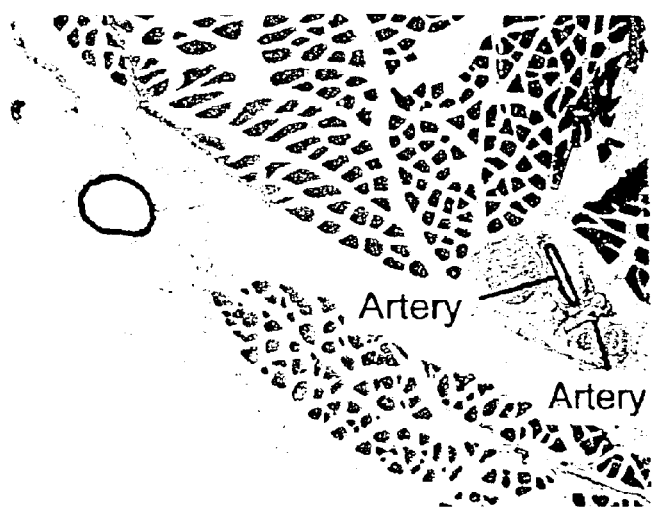
Figure 5B:
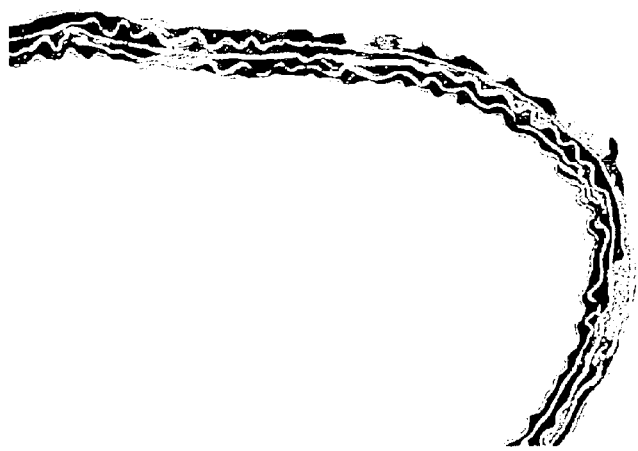
Figure 5C:
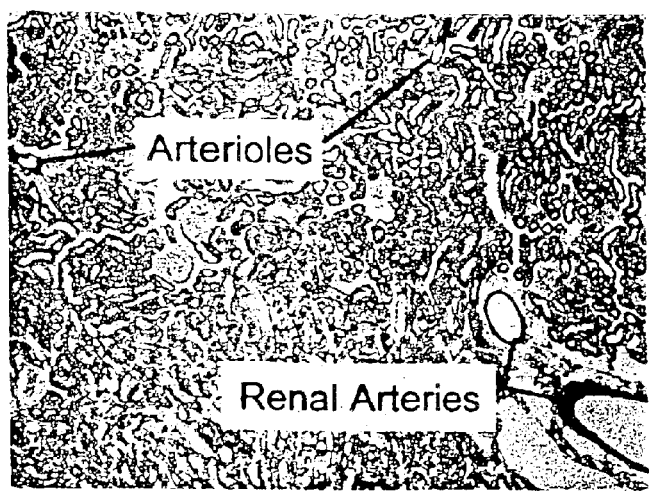

FIGS. 5(A–C). Histological examination of p2600Int/Lac Z expression in various adult SM-containing tissues. Four to six week old mice were perfusion fixed and tissues were, excised, and stained over night for Lac Z expression. After Lac Z staining, tissues were further fixed over night, embedded in paraffin, sectioned at 6–10 μm, and counterstained with eosin. FIG. 5A, Section of thigh muscle skeletal muscle showing Lac Z expression in a femoral artery and vein. Note that in adult animals, the p2600Int/Lac Z transgene was not expressed in skeletal muscle. FIG. 5B, Cross section of the aorta showing nearly uniform Lac Z expression in multiple SMC layers. FIG. 5C, Transverse section of the kidney showing SMC-specific staining in the large renal arteries as well as smaller renal arterioles.

Figure 6:
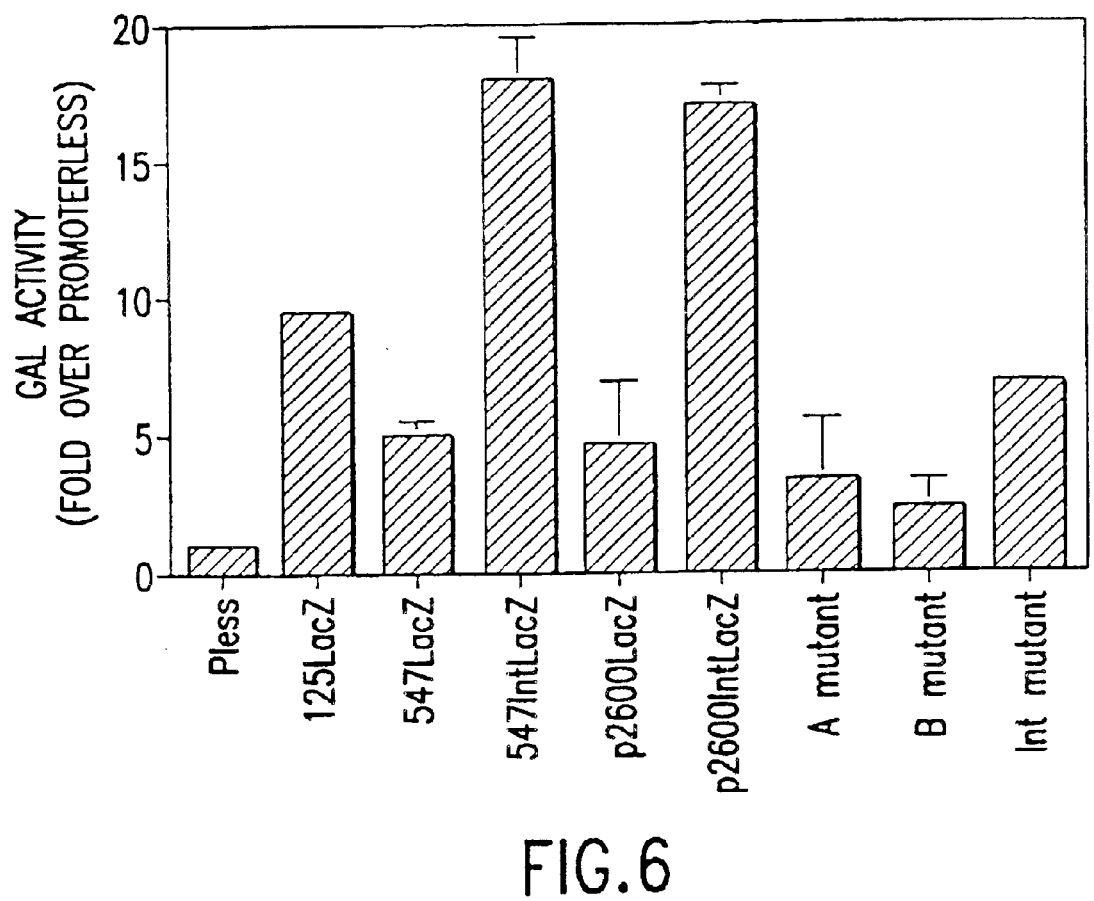

FIG. 6. The effects of CArG mutations on p2600Int/Lac Z activity in cultured SMC. Cultured rat SMC were transfected with equimolar amounts of the indicated deletion or site-directed mutant constructs. After 48 hr cells were lysed and galactosidase activity was measured spectrophotometrically. Gal activity (±S.D.) is expressed relative to the baseline Gal activity of a promoterless Gal construct set to 1. The first intron had significant transcriptional activity in the −547 and −2,600 context, and mutation of either CArG A, B, or the intronic CArG greatly decreased p2600Int/LacZ activity. Mutated CArG sequences were as follows: CArG A, 5'-AATTGTTTAA (SEQ ID NO:11); CArG B, 5'-CCCTATATCA (SEQ ID NO:12); and intronic CArG, 5'-AATAATTAAA (SEQ ID NO:13).

FIGS. 7(A–C). The effects of mutations to CArGs B and the intronic CArG on the expression of the p2600lnt/LacZ transgene at E13.5. Site-directed CArG mutations that have previously been shown to abolish SRF binding in vitro were made to CArG B and the intronic CArG in the p2600Int/Lac Z transgene construct. Transgenic mice were generated as described previously and stained for Lac Z expression at E13.5. LacZ expression in wild-type (Wt) embryos was indicative of endogenous SM α-A expression (FIG. 7A). Mutation of CArG B (B mut) completely abolished LacZ expression in all muscle cell types (FIG. 7B). Mutation of the intronic CArG (Int mut) had no effect on skeletal muscle expression but did eliminate expression in all SM (FIG. 7C). UA indicates umbilical artery. The mutated CArG sequences were as described above in FIG. 6.

Figure 8A:
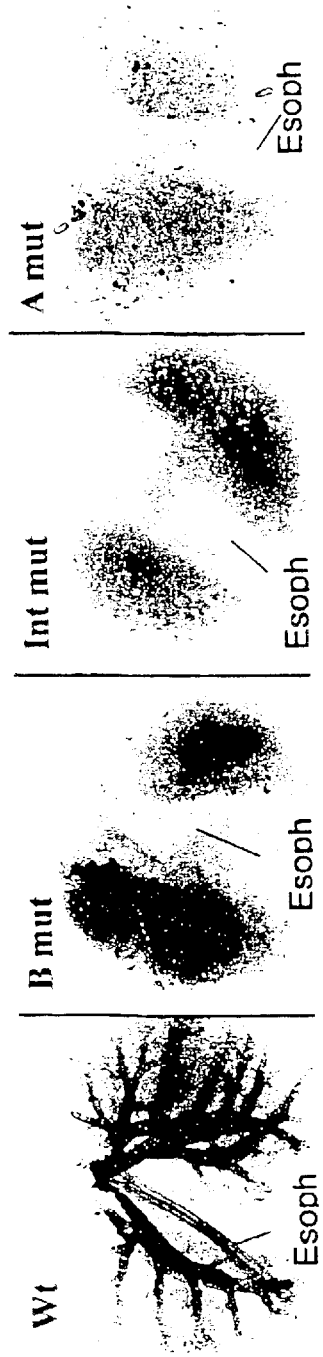
Figure 8B:
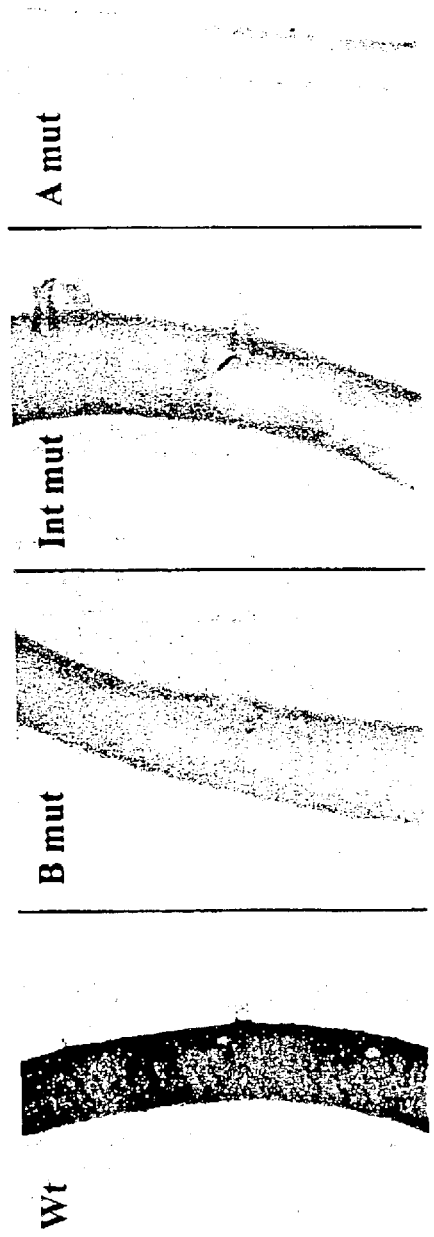
Figure 8C:
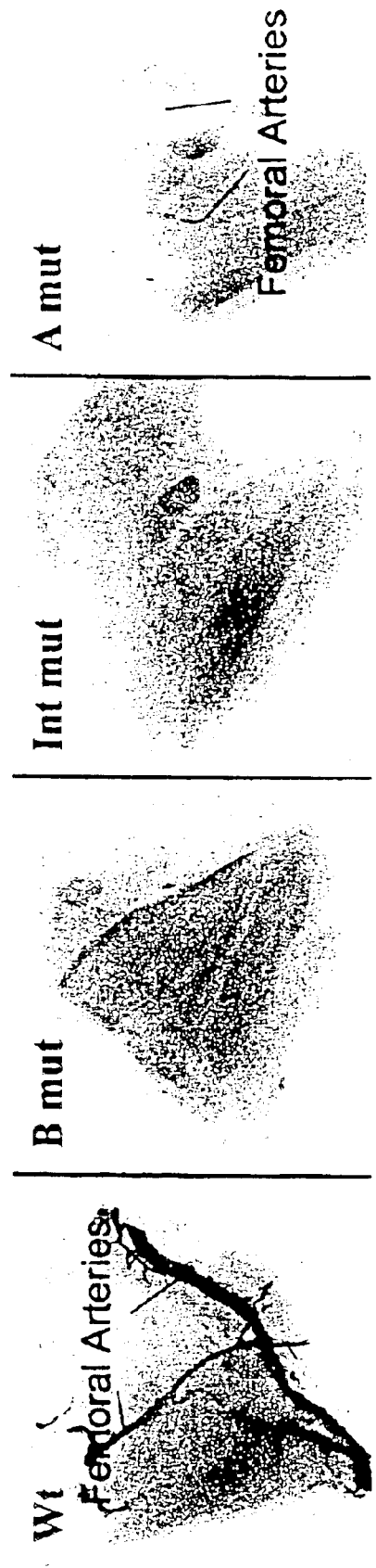

FIGS. 8(A–C). Effects of mutations to CArGs A, B, and the intronic CArG on the expression of the p2600Int/LacZ transgene in adult mice. Adult lung (FIG. 8A), aorta (FIG. 8B), and skeletal muscle (FIG. 8C), from wild-type (Wt) and CArG mutant mice were processed as previously described and results of staining for LacZ expression are shown. The CArG B mutation (B mut) and the intronic CArG mutation (Int mut) abolished expression in SMC from all tissues and vascular beds. In contrast, mutation of CArG A (A mut) eliminated expression in SM organs and large vessels such as the aorta, but only partially inhibited expression in smaller blood vessels.

Figure 9:
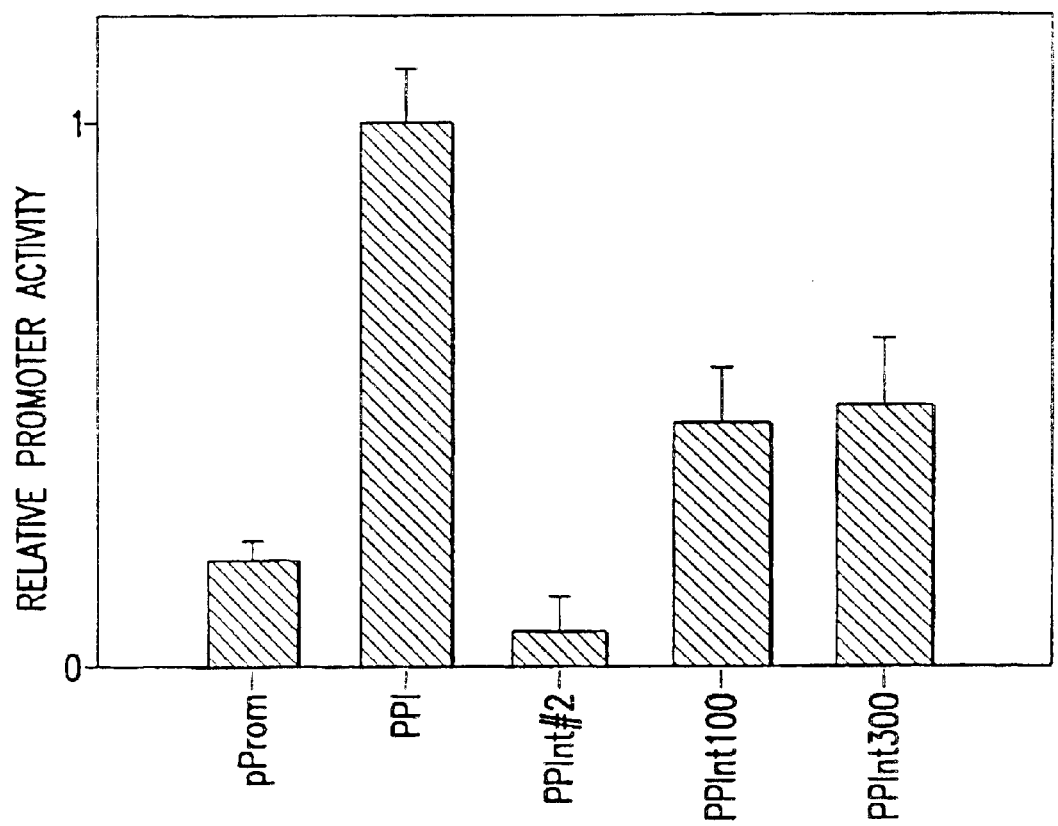

FIG. 9, The conserved 330 base pair intronic region contains both positive and negative regulatory elements. The ~100 bp region from +937 to +1,041 that contains the intronic CArG had significant positive activity when spliced onto the 5' promoter (compare PPInt100 with pProm) while an adjacent fragment from +863 to +990 (PPInt#2) significantly inhibited pProm activity. In addition, the full length, 330 base pair conserved intron region also resulted in significant positive activity when spliced onto the 5' promoter (compare PPInt300 with pProm). PPI (short for pProm and Intron) represents the activity of the large fragment from −2,558 bp through +2,784 bp.

FIGS. 10(A–B). Conserved cis Regulatory Elements in the SM α-actin 5' (FIG. 10A) and First Intron (FIG. 10B) Promoter Regions. Several important protein binding regions that have significant homology to known cis regulatory elements that bind AP1 and the GATA family of transcription factors were identified by DNase footprinting. This Figure also shows the mutated sequences for AP1-like (SEQ ID NO:28), GATA and CArGs A (SEQ ID NO:25), B (SEQ ID NO:22) and the intronic CArG (SEQ ID NO:30) which were prepared. The Figure further shows the homology that exists for the above sequences in humans (CArG B=SEQ ID NO:15; CArG A=SEQ ID NO:14; AP1-like= SEQ ID NO:19; Int CARG=SEQ ID NO:16; GATA=SEQ ID NO:20), rats (CArG B=SEQ ID NO:15; CArG A=SEQ ID NO:14; AP1-like=SEQ ID NO:26; Int CArG=SEQ ID NO:16; GATA=SEQ ID NO:31), mice (CArG B=SEQ ID NO:15; CArG A=SEQ ID NO:23; AP1-like=SEQ ID NO:26; Int CArG=SEQ ID NO:16; GATA=SEQ ID NO:31) and chickens (CArG B=SEQ ID NO:21; CArG A=SEQ ID NO:24; AP1-like=SEQ ID NO:27; Int CArG=SEQ ID NO:29; GATA=SEQ ID NO:32).

Figure 11:
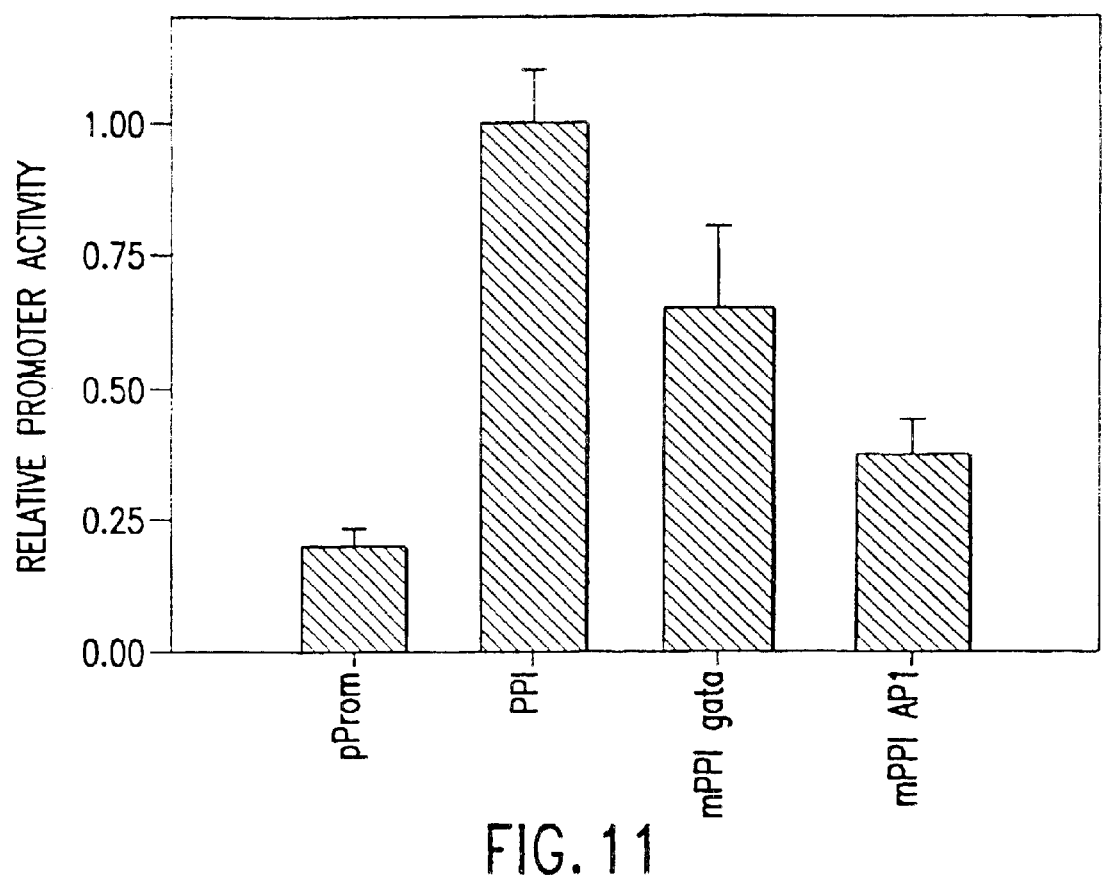

FIG. 11. The GATA and AP1-like Elements within the Conserved Intronic Region are Positive Regulators of Promoter Activity. Mutation of the highly conserved AP1-like or GATA elements (see FIG. 10) in the context of the PPInt transgene caused a 35% and 65% reduction in promoter activity, respectively. pProm represents about −2,600 through about +20 of the promoter; PPI represents the large fragment from −2,558 bp through +2,784 bp; mPPI gata represents PPI with the potential GATA site near +1,152 mutated (see FIG. 10B for the sequence); mPPI AP1 represents PPI with the potential AP1 site near +823 mutated (see FIG. 10B for the sequence).

FIGS. 12(A–D). Alignment of Human (SEQ ID NO:3), Rat (SEQ ID NO:4), Mouse (SEQ ID NO:5) and Chicken (SEQ ID NO:6) 5' Promoter Region from about −1,100 base pairs to the Start of Transcription. CArGs A and B are marked and boxed.

FIGS. 13(A–J). Alignment of Human (SEQ ID NO:7), Rat (SEQ ID NO:8), (SEQ ID NO:9) and Chicken (SEQ ID NO:10) First Intron Sequence from about +47 through about +2775. The intronic CArG is marked and boxed.

5. DETAILED DESCRIPTION OF THE INVENTION

The present invention provides promoters, enhancers and other regulatory elements that direct expression within SMC, comprising nucleotide sequences from the 5' regulatory region and the first intron, and transcriptionally active fragments thereof, that control expression of an SM α-A. Specifically provided are expression vectors, host cells and transgenic animals wherein an SM α-A regulatory region is capable of controlling expression of a heterologous gene, over-expressing an endogenous SMC gene or an inhibitor of a pathological process or knocking out expression of a specific gene believed to be important for a SM-related disease in SMC. Examples of such SMC include, but are not limited to, cells which form the contractile portion of the stomach, intestine and uterus, the walls of arteries, the ducts of secretory glands and many other regions in which slow and sustained contractions are needed. The invention also provides methods for using said vectors, cells and animals for screening candidate molecules for agonists and antagonists of disorders involving SMC. In an alternated embodiment, the invention provides compositions and methods for modulating expression of compounds within SMC, and to screening compounds that modulate expression within SMC. Methods for using the molecules and compounds identified by the screening assays for therapeutic treatments also are provided.

Described in detail below, in Sections 5.1 and 5.2, are nucleotide sequences of the SM α-A regulatory region, and expression vectors, host cells and transgenic animals wherein the expression of a heterologous gene is controlled by the SM α-A regulatory region. In Section 5.3, methods for using such polynucleotides (i.e., regulatory regions of the SM α-A gene) and fusion protein products, for screening compounds that interact with the regulatory region of the SM α-A gene are described. This Section describes both in vivo and in vitro assays to screen small molecules, compounds, recombinant proteins, peptides, nucleic acids, antibodies, etc. which bind to or modulate the activity of the SM α-A regulatory region. Section 5.4 describes methods for the use of identified agonists and antagonists for drug delivery or gene therapy. Finally, in Section 5.5, pharmaceutical compositions are described for using such agonists and antagonists to modulate SMC related disorders. Methods and compositions are provided for treating various SMC-related disorders, including, but not limited to, coronary artery disease, hypertension, stroke, asthma and multiple gastrointestinal, urogenital and reproductive disorders.

5.1 Polynucleotides and Nucleic Acids of the Invention

The present invention encompasses polynucleotide sequences comprising the 5' regulatory region and the first intron, and transcriptionally active fragments thereof, of the SM α-A gene. In particular, the present invention provides a polynucleotide comprising a 5342 bp sequence (SEQ ID NO:1) that is located within a SM α-A gene. Specifically, the polynucleotide comprises −2558 bp through +2784 bp of a SM α-A 5' promoter and first intron sequence. A 325 bp fragment (SEQ ID NO:2) of this promoter, from +773 bp to +1098 bp relative to the start of transcription is highly conserved and contains cis elements required to direct SMC-specific transcription in vivo.

In specific embodiments, SM α-A regulatory nucleic acids comprise the genomic DNA sequences of SEQ ID NO:1, or transcriptionally active fragments thereof. The regulatory sequences of the SM α-A gene comprise the polynucleotide sequences located between the nucleotide in position 1 and the nucleotide in position 5342 of the nucleotide sequence of SEQ ID NO:1, more preferably between positions 1 bp to 2605 bp, 2011 bp to 2605 bp and 2011 bp to 5342 bp of SEQ ID NO:1. Additional regulatory regions of the SM α-A gene comprise the polynucleotide sequences located between the nucleotide in position 3495 bp to 3599 bp, 3421 bp to 3548 bp of SEQ ID NO:1, most preferably between 3331 to 3656 of SEQ ID NO:1. Thus, in various embodiments of the invention, the regulatory region is a 325 bp intronic fragment from 3331 to 3656 of SEQ ID NO:1 (SEQ ID NO:2), a 104 bp fragment from 3495 bp to 3599 bp of SEQ ID NO:1 or a 127 bp fragment from 3421 bp to 3548 bp of SEQ D) NO:1 spliced downstream of the 5' promoter sequence of SEQ ID NO:1 (from 1–2558 of SEQ ID NO:1). In various embodiments, the polynucleotide maybe 5000, 4000, 3000, 2000, 1000, preferably approximately 500 and more preferably approximately 325 bp in length.

The invention further provides probes, primers and fragments of the SM α-A regulatory region. In one embodiment, purified nucleic acids consisting of at least 8 nucleotides (i.e., a hybridizable portion) of an SM α-A gene sequence are provided; in other embodiments, the nucleic acids consist of at least 20 (contiguous) nucleotides, 25 nucleotides, 50 nucleotides, 100 nucleotides, 200 nucleotides, 500, 1000, 2000, 3000, 4000 or 5000 nucleotides of an SM α-A sequence. For example, the nucleic acids consist of any 20 contiguous nucleotides of the nucleic acid set forth in SEQ ID NO:1 (e.g., 1–20, 5–24, 21–40, etc.). Methods which are well known to those skilled in the art can be used to construct these sequences, either in isolated form or contained in expression vectors. These methods include, for example, in vitro recombinant DNA techniques, synthetic techniques and in vivo genetic recombination. See, e.g., the techniques described in Sambrook et al., 1989, supra, and Ausabel et al., 1989, supra; also see the techniques described in "Oligonucleotide Synthesis", 1984, Gait M. J. ed., IRL Press, Oxford, which is incorporated herein by reference in its entirety.

In another embodiment, the nucleic acids are smaller than 20, 25, 35, 200 or 500 nucleotides in length. Nucleic acids can be single or double stranded. The invention also encompasses nucleic acids hybridizable to or complementary to the foregoing sequences. In specific aspects, nucleic acids are provided which comprise a sequence complementary to at least 10, 20, 25, 50, 100, 200, 500 nucleotides or the entire regulatory region of an SM α-A gene.

The probes, primers and fragments of the SM α-A regulatory region provided by the present invention can be used by the research community for various purposes. They can be used as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; and as a probe to "subtract-out" known sequences in the process of discovering other novel polynucleotides. Methods for performing the uses listed above are well known to those skilled in the art. References disclosing such methods include, without limitation, "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The nucleotide sequences of the invention also include nucleotide sequences that have at least 65%, 70%, 75%, 80%, 85%, 90%, 95%, 98% or more nucleotide sequence identity to the nucleotide sequence depicted in SEQ ID NO:1, and/or transcriptionally active fragments thereof.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical overlapping positions/total # of positions×100). In one embodiment, the two sequences are the same length.

The determination of percent identity between two sequences also can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264–2268, modified as in Karlin and Altschul (1993) *Proc. Natl. Acad. Sci. USA* 90:5873–5877. Such an algorithm is incorporated into the NBLAST and XBLAST programs of Altschul, et al. (1990) *J. Mol. Biol.* 215:403–410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.*25:3389–3402. Alternatively, PSI-Blast can be used to perform an iterated search which detects distant relationships between molecules (Id.). When utilizing BLAST, Gapped BLAST and PSI-Blast programs, the default parameters of the respective programs (e.g., XBLAST and NBLAST) can be used (see http://www.ncbi.nlm.nih.gov). Another preferred, non-limiting example of a mathematical algorithm utilized for the comparison of sequences is the algorithm of Myers and Miller, (1988) *CABIOS* 4:11–17. Such an algorithm is incorporated into the ALIGN program (version 2.0) which is part of the GCG sequence alignment software package. When utilizing the ALIGN program for comparing amino acid sequences, a PAM 120 weight residue table, a gap length penalty of 12 and a gap penalty of 4 can be used. In an alternate embodiment, alignments can be obtained using the NA_MULTIPLE_ALIGNMENT 1.0 program, using a GapWeight of 5 and a GapLengthWeight of 1.

The percent identity between two sequences can be determined using techniques similar to those described above, with or without allowing gaps. In calculating percent identity, typically only exact matches are counted.

The invention also encompasses:

(a) DNA vectors that contain any of the foregoing SM α-A regulatory sequences and/or their complements (i.e., antisense);

(b) DNA expression vectors that contain any of the foregoing SM α-A regulatory element sequences operatively associated with a heterologous gene, such as a reporter gene; and (c) genetically engineered host cells that contain any of the foregoing SM α-A regulatory element sequences operatively associated with a heterologous gene such that the SM α-A regulatory element directs the expression of the heterologous gene in the host cell.

Also encompassed within the scope of the invention are various transcriptionally active fragments of this regulatory region. A "transcriptionally active" or "transcriptionally functional" fragment of SEQ ID NO:1 according to the present invention refers to a polynucleotide comprising a fragment of said polynucleotide which is functional as a regulatory region for expressing a recombinant polypeptide or a recombinant polynucleotide in a recombinant cell host. For the purpose of the invention, a nucleic acid or polynucleotide is "transcriptionally active" as a regulatory region for expressing a recombinant polypeptide or a recombinant polynucleotide if said regulatory polynucleotide contains nucleotide sequences which contain transcriptional information, and such sequences are operably associated to nucleotide sequences which encode the desired polypeptide or the desired polynucleotide.

In particular, the transcriptionally active fragments of the SM α-A regulatory region of the present invention encompass those fragments that are of sufficient length to promote transcription of a heterologous gene, such as a reporter gene, when operatively linked to the SM α-A regulatory sequence and transfected into an SM cell line. Typically, the regulatory region is placed immediately 5' to, and is operatively associated with the coding sequence. As used herein, the term "operatively associated" refers to the placement of the regulatory sequence immediately 5' (upstream) of the reporter gene, such that transacting factors required for initiation of transcription, such as transcription factors, polymerase subunits and accessory proteins, can assemble at this region to allow RNA polymerase dependent transcription initiation of the reporter gene.

In one embodiment, the polynucleotide sequence chosen may further comprise other nucleotide sequences, either from the SM α-A gene, or from a heterologous gene. In another embodiment, multiple copies of a promoter sequence, or a fragment thereof, may be linked to each other. For example, the promoter sequence, or a fragment thereof, may be linked to another copy of the promoter sequence, or another fragment thereof, in a head to tail, head to head, or tail to tail orientation. In another embodiment, an SMC-specific enhancer may be operatively linked to the SM α-A regulatory sequence, or fragment thereof, and used to enhance transcription from the construct containing the SM α-A regulatory sequence.

Also encompassed within the scope of the invention are modifications of this nucleotide sequence without substantially affecting its transcriptional activities. Such modifications include additions, deletions and substitutions. In addition, any nucleotide sequence that selectively hybridizes to the complement of the sequence of SEQ ID NO:1 under stringent conditions, and is capable of activating the expression of a coding sequence is encompassed by the invention. Exemplary moderately stringent hybridization conditions are as follows: prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 hours at 65° C. in prehybridization mixture containing 100 µg/ml denatured salmon sperm DNA and 5–20×10$^6$ cpm of $^{32}$P-labeled probe. Washing of filters is done at 37° C. for 1 hour in a solution containing 2×SSC, 0.01% PVP, 0.01% Ficoll, and 0.01% BSA. This is followed by a wash in 0.1×SSC at 50° C. for 45 min before autoradiography. Alternatively, exemplary conditions of high stringency are as follows: e.g., hybridization to filter-bound DNA in 0.5 M NaHPO$_4$, 7% sodium dodecyl sulfate (SDS), 1 mM EDTA at 65° C., and washing in 0.×SSC/0.1% SDS at 68° C. (Ausubel F. M. et al., eds., 1989, Current Protocols in Molecular Biology, Vol. I Green Publishing Associates, Inc., and John Wiley & sons, Inc., New York, at p. 2.10.3). Other conditions of high stringency which may be used are well known in the art. In general, for probes between 14 and 70 nucleotides in length the melting temperature (TM) is calculated using the formula: Tm(° C.)=81.5+16.6(log [monovalent cations (molar)])+0.41(% G+C)−(500/N) where N is the length of the probe. If the hybridization is carried out in a solution containing formamide, the melting temperature is calculated using the equation Tm(° C.)=81.5+16.6(log[monovalent cations (molar)])+0.41(% G+C)−(0.61% formamide)−(500/N) where N is the length of the probe. In general, hybridization is carried out at about 20–25 degrees below Tm (for DNA-DNA hybrids) or 10–15 degrees below Tm (for RNA-DNA hybrids).

The SM α-A regulatory region, or transcriptionally functional fragments thereof, is preferably derived from a mammalian organism. Screening procedures which rely on nucleic acid hybridization make it possible to isolate gene sequences from various organisms. The isolated polynucleotide sequence disclosed herein, or fragments thereof, may be labeled and used to screen a cDNA library constructed from mRNA obtained from appropriate cells or tissues (e.g., muscle tissue) derived from the organism of interest. The hybridization conditions used should be of a lower stringency when the cDNA library is derived from an organism different from the type of organism from which the labeled sequence was derived. Low stringency conditions are well know to those of skill in the art, and will vary depending on the specific organisms from which the library and the labeled sequence are derived. For guidance regarding such conditions see, for example, Sambrook et al., 1989, Molecular Cloning, A Laboratory Manual, Second Edition, Cold Spring Harbor Press, N.Y., and Ausabel et al., 1989, Current Protocols in Molecular Biology, Green Publishing Associates and Wiley Interscience, N.Y., each of which is incorporated herein by reference in its entirety. Further, mammalian SM α-A regulatory region homologues may be isolated from, for example, bovine or other non-human nucleic acid, by performing polymerase chain reaction (PCR) amplification using two primer pools designed on the basis of the nucleotide sequence of the SM α-A regulatory region disclosed herein. The template for the reaction may be cDNA obtained by reverse transcription of the mRNA prepared from, for example, bovine or other non-human cell lines, or tissue known to express the SM α-A gene. For guidance regarding such conditions, see, e.g., Innis et al. (Eds.) 1995, *PCR Strategies,* Academic Press Inc., San Diego; and Erlich (ed) 1992, *PCR Technology,* Oxford University Press, New York, each of which is incorporated herein by reference in its entirety.

Regions of the human, rat, mouse and chicken SM α-A gene sequences were compared and aligned in FIGS. 12 and 13. Specifically, FIG. 12 shows an alignment for the human (SEQ ID NO:3), rat (SEQ ID NO:4), mouse (SEQ ID NO:5) and chicken (SEQ ID NO:6) sequences from about −1,100 base pairs up to the start of transcription. FIG. 13 shows an alignment for the human (SEQ ID NO:7), rat (SEQ ID NO:8), mouse (SEQ ID NO:9) and chicken (SEQ ID NO:10) sequences from about +47 through about +2775 relative to the start of transcription. Both of the figures were created using the NA_MULTIPLE_ALIGNMENT 1.0 program, using a GapWeight of 5 and a GapLengthWeight of 1. As noted in the figures, each of the CArG elements (A, B and the intronic CArG) are absolutely conserved.

Promoter sequences within the 5' non-coding regions of the SM α-A gene may be further defined by constructing nested 5' and/or 3' deletions using conventional techniques such as exonuclease III or appropriate restriction endonuclease digestion. The resulting deletion fragments can be inserted into the promoter reporter vector to determine whether the deletion has reduced or obliterated promoter activity, such as described, for example, by Coles et al. (Hum. Mol. Genet., 7:791–800, 1998). In this way, the boundaries of the promoters may be defined. If desired, potential individual regulatory sites within the promoter may be identified using site directed mutagenesis or linker scanning to obliterate potential transcription factor binding sites within the promoter individually or in combination. The effects of these mutations on transcription levels may be determined by inserting the mutations into cloning sites in promoter reporter vectors. These types of assays are well known to those skilled in the art (WO 97/17359, U.S. Pat. No. 5,374,544, EP 582 796, U.S. Pat. Nos. 5,698,389, 5,643,746, 5,502,176, and 5,266,488).

The SM α-A regulatory regions and transcriptionally functional fragments thereof, and the fragments and probes described herein which serve to identify SM α-A regulatory regions and fragments thereof, may be produced by recombinant DNA technology using techniques well known in the art. Methods which are well known to those skilled in the art can be used to construct these sequences, either in isolated form or contained in expression vectors. These methods include, for example, in vitro recombinant DNA techniques, synthetic techniques and in vivo genetic recombination. See, e.g., the techniques described in Sambrook et al., 1989, supra, and Ausabel et al., 1989, supra; also see the techniques described in "Oligonucleotide Synthesis", 1984, Gait M. J. ed., IRL Press, Oxford, which is incorporated herein by reference in its entirety.

Alterations in the regulatory sequences can be generated using a variety of chemical and enzymatic methods which are well known to those skilled in the art. For example, regions of the sequences defined by restriction sites can be deleted. Oligonucleotide-directed mutagenesis can be employed to alter the sequence in a defined way and/or to introduce restriction sites in specific regions within the sequence. Additionally, deletion mutants can be generated using DNA nucleases such as Bal31, ExoIII, or S1 nuclease. Progressively larger deletions in the regulatory sequences are generated by incubating the DNA with nucleases for increased periods of time (see, e.g., Ausubel et al., 1989, supra).

The altered sequences are evaluated for their ability to direct expression of heterologous coding sequences in appropriate host cells. It is within the scope of the present invention that any altered regulatory sequences which retain their ability to direct expression of a coding sequence be incorporated into recombinant expression vectors for further use.

5.2 Analysis of SMC-Specific Promoter Activity

The rat SM α-A gene regulatory region shows selective tissue and cell-type specificity; i.e., it induces gene expression in SMC. Thus, the regulatory region, and transcriptionally active fragments thereof, of the present invention may be used to induce expression of a heterologous coding sequence in SMC. The present invention provides for the use of the SM α-A gene regulatory region to achieve tissue specific expression of a target gene. The activity and the specificity of the SM α-A regulatory region can further be assessed by monitoring the expression level of a detectable polynucleotide operably associated with the SM α-A promoter in different types of cells and tissues. As discussed hereinbelow, the detectable polynucleotide may be either a polynucleotide that specifically hybridizes with a predefined oligonucleotide probe, or a polynucleotide encoding a detectable protein.

5.2.1 SM α-A Promoter Driven Reporter Constructs

The regulatory polynucleotides according to the invention may be advantageously part of a recombinant expression vector that may be used to express a coding sequence, or reporter gene, in a desired host cell or host organism. The SM α-A regulatory region of the present invention, and transcriptionally active fragments thereof, may be used to direct the expression of a heterologous coding sequence. In particular, the present invention encompasses mammalian, such as murine, SM α-A regulatory regions. In accordance with the present invention, transcriptionally active fragments of the SM α-A regulatory region encompass those fragments of the region which are of sufficient length to promote transcription of a reporter coding sequence to which the fragment is operatively linked.

A variety of reporter gene sequences well known to those of skill in the art can be utilized, including, but not limited to, genes encoding fluorescent proteins such as green fluorescent protein (GFP), enzymes (e.g. CAT, beta-galactosidase, luciferase) or antigenic markers. For convenience, enzymatic reporters and light-emitting reporters analyzed by colorometric or fluorometric assays are preferred for the screening assays of the invention.

In one embodiment, for example, a bioluminescent, chemiluminescent or fluorescent protein can be used as a light-emitting reporter in the invention. Types of light-emitting reporters, which do not require substrates or cofactors, include, but are not limited to the wild-type green fluorescent protein (GFP) of *Victoria aequoria* (Chalfie et al., 1994, Science 263:802–805), and modified GFPs (Heim et al., 1995, Nature 373:663–4; PCT publication WO 96/23810). Transcription and translation of this type of reporter gene leads to the accumulation of the fluorescent protein in test cells, which can be measured by a fluorimeter, or a flow cytometer, for example, by methods that are well known in the art (see, e.g., Lackowicz, 1983, Principles of Fluorescence Spectroscopy, Plenum Press, New York).

Another type of reporter gene that may be used are enzymes that require cofactor(s) to emit light, including but not limited to, Renilla luciferase. Other sources of luciferase also are well known in the art, including, but not limited to, the bacterial luciferase (luxAB gene product) of *Vibrio harveyi* (Karp, 1989, Biochim. Biophys. Acta 1007:84–90; Stewart et al. 1992, J. Gen. Microbiol, 138:1289–1300), and the luciferase from firefly, *Photinus pyralis* (De Wet et al. 1987, Mol. Cell. Biol. 7:725–737), which can be assayed by light production (Miyamoto et al., 1987, J. Bacteriol. 169:247–253; Loessner et al. 1996, Environ. Microbiol. 62:1133–1140; and Schultz & Yarus, 1990, J. Bacteriol. 172:595–602).

Reporter genes that can be analyzed using colorimetric analysis include, but are not limited to, β-galactosidase (Nolan et al. 1988, Proc. Natl. Acad. Sci. USA 85:2603–07), β-glucuronidase (Roberts et al. 1989, Curr. Genet. 15:177–180), luciferase (Miyamoto et al., 1987, J. Bacteriol. 169:247–253), or β-lactamase. In one embodiment, the reporter gene sequence comprises a nucleotide sequence which encodes a LacZ gene product, β-galactosidase. The enzyme is very stable and has a broad specificity so as to allow the use of different histochemical, chromogenic or fluorogenic substrates, such as, but not limited to, 5-bromo-4-chloro-3-indoyl-β-D-galactoside (X-gal), lactose 2,3,5-triphenyl-2H-tetrazolium (lactose-tetrazolium) and fluorescein galactopyranoside (see Nolan et al., 1988, supra).

In another embodiment, the product of the *E. coli* β-glucuronidase gene (GUS) can be used as a reporter gene (Roberts et al. 1989, Curr. Genet. 15:177–180). GUS activity can be detected by various histochemical and fluorogenic substrates, such as X-glucuronide (Xgluc) and 4-methylumbelliferyl glucuronide.

In addition to reporter gene sequences such as those described above, which provide convenient colorimetric responses, other reporter gene sequences, such as, for example, selectable reporter gene sequences, can routinely be employed. For example, the coding sequence for chloramphenicol acetyl transferase (CAT) can be utilized, leading to SM α-A regulatory region-dependent expression of chloramphenicol resistant cell growth.

The use of CAT and the advantages of a selectable reporter gene are well known to those skilled in the art (Eikmanns et al. 1991, Gene 102:93–98). Other selectable reporter gene sequences also can be utilized and include, but are not limited to, gene sequences encoding polypeptides which confer zeocin (Hegedus et al. 1998, Gene 207:241–249) or kanamycin resistance (Friedrich & Soriano, 1991, Genes. Dev. 5:1513–1523).

Other reporter genes, such as toxic gene products, potentially toxic gene products, and antiproliferation or cytostatic gene products, also can be used. In another embodiment, the detectable reporter polynucleotide may be either a polynucleotide that specifically hybridizes with a predefined oligonucleotide probe, or a polynucleotide encoding a detectable protein, including an SM α-A polypeptide or a fragment or a variant thereof. This type of assay is well known to those skilled in the art (U.S. Pat. Nos. 5,502,176 and 5,266,488).

SM α-A driven reporter constructs can be constructed according to standard recombinant DNA techniques (see, e.g., Methods in Enzymology, 1987, volume 154, Academic Press; Sambrook et al. 1989, Molecular Cloning—A Laboratory Manual, 2nd Edition, Cold Spring Harbor Press, New York; and Ausubel et al. Current Protocols in Molecular Biology, Greene Publishing Associates and Wiley Interscience, New York, each of which is incorporated herein by reference in its entirety).

Methods for assaying promoter activity are well-known to those skilled in the art (see, e.g., Sambrook et al., Molecular Cloning A Laboratory Manual, Cold Spring Harbor Laboratory, Cold Spring Harbor, N.Y., 1989). An example of a typical method that can be used involves a recombinant vector carrying a reporter gene and genomic sequences from the SM α-A genomic sequence of SEQ ID NO:1. Briefly, the expression of the reporter gene (for example, green fluorescent protein, luciferase, β-galactosidase or chloramphenicol acetyl transferase) is detected when placed under the control of a biologically active polynucleotide fragment. Genomic sequences located upstream of the first exon of the gene may be cloned into any suitable promoter reporter vector. For example, a number of commercially available vectors can be engineered to insert the SM α-A regulatory region of the invention for expression in mammalian host cells. Non-limiting examples of such vectors are pSEAPBasic, pSEAP-Enhancer, pβgal-Basic, pβgal-Enhancer, or pEGFP-1 Promoter Reporter vectors (Clontech, Palo Alto, Calif.) or pGL2-basic or pGL3-basic promoterless luciferase reporter gene vector (Promega, Madison, Wis.). Each of these promoter reporter vectors include multiple cloning sites positioned upstream of a reporter gene encoding a readily assayable protein such as secreted alkaline phosphatase, green fluorescent protein, luciferase or β-galactosidase. The regulatory sequences of the SM α-A gene are inserted into the cloning sites upstream of the reporter gene in both orientations and introduced into an appropriate host cell. The level of reporter protein is assayed and compared to the level obtained with a vector lacking an insert in the cloning site. The presence of an elevated expression level in the vector containing the insert with respect the control vector indicates the presence of a promoter in the insert.

Expression vectors that comprise an SM α-A gene regulatory region may further contain a gene encoding a selectable marker. A number of selection systems may be used, including but not limited to, the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026) and adenine phosphoribosyltransferase (Lowy et al., 1980, Cell 22:817) genes, which can be employed in tk$^-$, hgprt$^-$ or aprt$^-$ cells, respectively. Also, antimetabolite resistance can be used as the basis of selection for dhfr, which confers resistance to methotrexate (Wigler et al., 1980, Proc. Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147) genes. Additional selectable genes include trpB, which allows cells to utilize indole in place of tryptophan; hisD, which allows cells to utilize histinol in place of histidine (Hartman & Mulligan, 1988, Proc. Natl. Acad. Sci. USA 85:8047); ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.) and glutamine synthetase (Bebbington et al., 1992, Biotech 10:169).

5.2.2 Characterization of Transcriptionally Active Regulatory Fragments

A fusion construct comprising an SM α-A regulatory region, or a fragment thereof, can be assayed for transcriptional activity. As a first step in promoter analysis, the transcriptional start point (+1 site) of the SMC-specific gene under study has to be determined using primer extension assay and/or RNAase protection assay, following standard methods (Sambrook et al.,1989, Molecular Cloning: A Laboratory Manual, Cold Spring Harbor, Cold Spring Harbor Press). The DNA sequence upstream of the +1 site is generally considered as the promoter region responsible for gene regulation. However, downstream sequences, including sequences within introns, also may be involved in gene regulation. To begin testing for promoter activity, a −3 kb to +3 kb region (where +1 is the transcriptional start point) may be cloned upstream of the reporter gene coding region. Two or more additional reporter gene constructs also may be made which contain 5' and/or 3' truncated versions of the regulatory region to aid in identification of the region responsible for SMC-specific expression. The choice of the type of reporter gene is made based on the application.

In a preferred embodiment, a GFP reporter gene construct is used. The application of green fluorescent protein (GFP) as a reporter is particularly useful in the study of SMC-specific gene promoters. A major advantage of using GFP as a reporter lies in the fact that GFP can be detected in freshly isolated SMC without the need for substrates.

In another embodiment of the invention, a Lac Z reporter construct is used. The Lac Z gene product, β-galactosidase, is extremely stable and has a broad specificity so as to allow the use of different histochemical, chromogenic or fluorogenic substrates, such as, but not limited to, 5-bromo-4-chloro-3-indoyl-β-D-galactoside (X-gal), lactose 2,3,5-triphenyl-2H-tetrazolium (lactose-tetrazolium) and fluorescein galactopyranoside (see Nolan et al., 1988, supra).

For promoter analysis in transgenic mice, GFP that has been optimized for expression in mammalian cells is preferred. The promoterless cloning vector pEGFP1 (Clontech, Palo Alto, Calif.) encodes a red shifted variant of the wild-type GFP which has been optimized for brighter fluorescence and higher expression in mammalian cells (Cormack et al., 1996, Gene 173:33; Haas et al., 1996,Curr. Biol. 6:315). Moreover, since the maximal excitation peak of this enhanced GFP (EGFP) is at 488 nm, commonly used filter sets such as fluorescein isothiocyanate (FITC) optics which illuminate at 450–500 nm can be used to visualize GFP fluorescence. pEGFP1 proved to be useful as a reporter vector for promoter analysis in transgenic mice (Okabe et al, 1997, FEBS Lett. 407:313). In an alternate embodiment, transgenic mice containing transgenes with a SM α-A regulatory region upstream of the Lac Z reporter gene are utilized.

Putative promoter fragments can be prepared (usually from a parent phage clone containing 8–10 kb genomic DNA including the promoter region) for cloning using methods known in the art. In one embodiment, for example, promoter fragments are cloned into the multiple cloning site of a Lac Z reporter vector. In one embodiment, restriction endonucleases are used to excise the regulatory region fragments to be inserted into the reporter vector. For example, if NotI and EcoRI sites were present at −2.5 kb and +2.7 kb positions of the regulatory fragment, then the −2,5 kb to +27 kb fragment can be generated by digestion with NotI and Eco RI. However, the feasibility of this method depends on the availability of proper restriction endonuclease sites in the regulatory fragment. In a preferred embodiment, the required promoter fragment is amplified by polymerase chain reaction (PCR; Saiki et al., 1988, Science 239:487) using oligonucleotide primers bearing the appropriate sites for restriction endonuclease cleavage. The sequence necessary for restriction cleavage is included at the 5' end of the forward and reverse primers which flank the regulatory fragment to be amplified. After PCR amplification, the appropriate ends are generated by restriction digestion of the PCR product. The promoter fragments, generated by either method, are then ligated into the multiple cloning site of the reporter vector following standard cloning procedures (Sambrook et al.,1989, supra). It is recommended that the DNA sequence of the PCR generated promoter fragments in the constructs be verified prior to generation of transgenic animals. The resulting reporter gene construct will contain the putative promoter fragment located upstream of the reporter gene open reading frame, e.g., GFP or Lac Z cDNA.

In the preferred embodiment, the following protocol is used. Fifty to 100 pg of the reporter gene construct is digested using appropriate restriction endonucleases to release the transgene fragment. The restriction endonuclease cleaved products are resolved in a 1% (w/v) agarose gel containing 0.5 ug/ml ethidium bromide and TAE buffer (1×:0.04 M Tri-acetate, 0.001 M EDTA, pH 8.0) at 5–6 V/cm. The transgene band is located by size using a UV transilluminator, preferably using long-wavelength UV lamp to reduce nicking of DNA, and the gel piece containing the required band carefully excised. The gel slice and 1 ml of 0.5×TAE buffer is added to a dialysis bag, which has been boiled in 1 mM EDTA, pH 8.0 for 10 minutes (Sambrook et al.,1989, supra) and the ends are fastened. The dialysis bag containing the gel piece is submerged in a horizontal gel electrophoresis chamber containing 0.5×TAE buffer, and electrophoresed at 5–6 V/cm for 45 minutes. The current flow in the electrophoresis chamber is reversed for one minute before stopping the run to release the DNA which may be attached to the wall of the dialysis tube. The TAE buffer containing the electroeluted DNA from the dialysis bag is collected in a fresh eppendorf tube. The gel piece may be observed on the UV transilluminator to ascertain that the electroelution of the DNA is complete.

The electroeluted DNA sample is further purified by passing through Elutip D columns. The matrix of the column is prewashed with 1–2 ml of High salt buffer (1.0 M NaCl, 20 mM Tris. Cl, 1.0 mM EDTA, pH 7.5), followed by a wash with 5 ml of Low salt buffer (0.2 M NaCl, 20 mM Tris. Cl, 1.0 mM EDTA, pH 7.5). A 5 ml syringe is used to apply solutions to the Elutip D column, avoiding reverse flow. The solution containing the electroeluted DNA is loaded slowly. The column is washed with 2–3 ml of Low salt buffer and the DNA is eluted in 0.4 ml of High salt buffer. Two volumes of cold 95% ethanol is added to precipitate DNA. The DNA is collected by centrifugation in a microcentrifuge at 14,000 g for 10 minutes, carefully removing the alcohol without disrupting the DNA pellet. The pellet is washed at least twice with 70% (v/v) ethanol, and dried. The washing and drying steps are important, as residual salt and ethanol are lethal to the developing embryos. The DNA is resuspend in the injection buffer (10 mM TM, 0.1 mM EDTA, pH 7.5 prepared with Milli-Q quality water). The concentration of the purified transgene DNA fragment is determined by measuring the optical density at $A_{260}$ ($A_{260}$=1 for 50 µg/ml DNA) using a spectrophotometer. DNA prepared in this manner is suitable for microinjection into fertilized mouse eggs.

5.2.3 SMC-Specific Promoter Analysis Using Transgenic Mice

The mammalian SM α-A regulatory region can be used to direct expression of, inter alia, a reporter coding sequence, a homologous gene or a heterologous gene in transgenic animals. Animals of any species, including, but not limited to, mice, rats, rabbits, guinea pigs, pigs, micro-pigs, goats, sheep, and non-human primates, e.g., baboons, monkeys and chimpanzees may be used to generate transgenic animals. The term "transgenic," as used herein, refers to non-human animals expressing SM α-A gene sequences from a different species (e.g., mice expressing SM α-A sequences), as well as animals that have been genetically engineered to overexpress endogenous (i.e., same species) SM α-A sequences or animals that have been genetically engineered to knockout specific sequences.

In one embodiment, the present invention provides for transgenic animals that carry a transgene such as a reporter gene under the control of the SM α-A regulatory region or transcriptionally active fragments thereof in all their cells, as well as animals that carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (1992, Proc. Natl. Acad. Sci. USA 89:6232–6236). When it is desired that the transgene be integrated into the chromosomal site of the endogenous corresponding gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene.

Any technique known in the art may be used to introduce a transgene under the control of the SM α-A regulatory region into animals to produce the founder lines of transgenic animals. Such techniques include, but are not limited to, pronuclear microinjection (Hoppe & Wagner, 1989, U.S. Pat. No. 4,873,191); nuclear transfer into enucleated oocytes of nuclei from cultured embryonic, fetal or adult cells induced to quiescence (Campbell et al., 1996, Nature 380:64–66; Wilmut et al., Nature 385:810–813); retrovirus gene transfer into germ lines (Van der Putten et al., 1985, Proc. Natl. Acad. Sci., USA 82:6148–6152); gene targeting in embryonic stem cells (Thompson et al., 1989, Cell 65:313–321); electroporation of embryos (Lo, 1983, Mol. Cell. Biol. 31:1803–1814); and sperm-mediated gene transfer (Lavitrano et al., 1989, Cell 57:717–723; see, Gordon, 1989, Transgenic Animals, Intl. Rev. Cytol. 115:171–229).

For example, for microinjection of fertilized eggs, a linear DNA fragment (the transgene) containing the regulatory region, the reporter gene and the polyadenylation signals, is excised from the reporter gene construct. The transgene may be gel purified by methods known in the art, for example, by the electroelution method. Following electroelution of gel fragments, any traces of impurities are further removed by passing through Elutip D column (Schleicher & Schuell, Dassel, Germany).

In a preferred embodiment, the purified transgene fragment is microinjected into the male pronuclei of fertilized eggs obtained from B6 CBA females by standard methods (Hogan, 1986, Manipulating the Mouse Embryo, A Laboratory Manual. Cold Spring Harbor Laboratory Press, Cold Spring Harbor, N.Y.). Mice are analyzed transiently at several embryonic stages or by establishing founder lines that allow more detailed analysis of transgene expression throughout development and in adult animals. Transgene presence is analyzed by PCR using genomic DNA purified from placentas (transients) or tail clips (founders) according to the method of Vernet et al., Methods Enzymol. 1993;225:434–451 using the following primers:

5' primer: 5'-GCATCGAGCTGGGTAATAAGC
    GTTGGCAAT-3'    (SEQ ID NO:17)

3' primer: 5'-GACACCAGACCAACTGGTAA
    TGGTAGCGAC-3'    (SEQ ID NO:18)

which are complementary to the Lac Z gene from E. coli (Acc. No. V00296) and produce an 800 bp fragment. Preferably, the PCR reaction is carried out in a volume of 100 μl containing 1 μg of genomic DNA, in 1×reaction buffer supplemented with 0.2 mM dNTPs, 2 mM $MgCl_2$, 600 μM each of primer, and 2.5 units of Taq polymerase (Promega, Madison, Wis.). Each of the 30 PCR cycles consists of denaturation at 94° C. for 1 min, annealing at 54° C. for 1 min, and extension at 72° C. for 1 min. The founder mice may be identified by the presence of the 800 bp PCR product. The founder mice are then mated with C57B1 partners to generate transgenic $F_1$ lines of mice.

5.3 Screening Assays

Compounds that interfere with the abnormal function and/or growth of SMC can provide therapies targeting defects in SMC-related disorders including, but not limited to, atherosclerosis, coronary artery disease, hypertension, stroke, asthma and multiple gastrointestinal, urogenital and reproductive disorders. Such compounds may be used to interfere with the onset or the progression of SMC-related disorders. Compounds that stimulate or inhibit promoter activity may be used to ameliorate symptoms of SMC-related disorders.

Transgenic animals or SMC containing an SM α-A regulatory region, or fragment thereof, operably linked to a reporter gene, can be used as systems for the screening of agents that modulate SM α-A transcriptional activity. In addition, SM α-A containing transgenic mice provide an experimental model both in vivo and in vitrio to develop new methods of treating SMC-related disorders by targeting drugs to cause arrest in the progression of such disorders.

The present invention encompasses screening assays designed to identify compounds that modulate activity of the SM α-A regulatory region. The present invention encompasses in vitro and cell-based assays, as well as in vivo assays in transgenic animals. As described hereinbelow, compounds to be tested may include, but are not limited to, oligonucleotides, peptides, proteins, small organic or inorganic compounds, antibodies, etc.

Examples of compounds may include, but are not limited to, peptides, such as, for example, soluble peptides, including, but not limited to, Ig-tailed fusion peptides, and members of random peptide libraries; (see, e.g., Lam, et al., 1991, Nature 354:82–84; Houghten, et al., 1991, Nature 354:84–86), and combinatorial chemistry-derived molecular library made of D- and/or L- configuration amino acids, phosphopeptides (including, but not limited to members of random or partially degenerate, directed phosphopeptide libraries; see, e.g., Songyang, et al., 1993, Cell 72:767–778), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

Such compounds may further comprise compounds, in particular drugs or members of classes or families of drugs, known to ameliorate the symptoms of an SMC-related disorder.

Such compounds include, but are not limited to, families of antidepressants such as lithium salts, carbamazepine, valproic acid, lysergic acid diethylamide (LSD), p-chlorophenylalanine, p-propyldopacetamide dithiocarbamate derivatives e.g., FLA 63; anti-anxiety drugs, e.g., diazepam; monoamine oxidase (MAO) inhibitors, e.g., iproniazid, clorgyline, phenelzine and isocarboxazid; biogenic amine uptake blockers, e.g., tricyclic antidepressants such as desipramine, imipramine and amitriptyline; serotonin reuptake inhibitors e.g., fluoxetine; antipsychotic drugs such as phenothiazine derivatives (e.g., chlorpromazine (thorazine) and trifluopromazine)), butyrophenones (e.g., haloperidol (Haldol)), thioxanthene derivatives (e.g., chlorprothixene), and dibenzodiazepines (e.g., clozapine); benzodiazepines; dopaminergic agonists and antagonists e.g., L-DOPA, cocaine, amphetamine, α-methyl-tyrosine, reserpine, tetrabenazine, benzotropine, pargyline; noradrenergic agonists and antagonists e.g., clonidine, phenoxybenzamine, phentolamine, tropolone; nitrovasodilators (e.g., nitroglycerine, nitroprusside as well as NO synthase enzymes); and growth factors (e.g., VEGF, FGF, angiopoetins and endostatin).

In one preferred embodiment, primary cultures of germ cells containing a mammalian SM α-A regulatory region operatively linked to a heterologous gene are used to develop assay systems to screen for compounds which can inhibit sequence-specific DNA-protein interactions. Such methods comprise contacting a compound to a cell that expresses a gene under the control of an SM α-A regulatory region, or a transcriptionally active fragment thereof, measuring the level of the gene expression or gene product activity and comparing this level to the level of gene expression or gene product activity produced by the cell in the absence of the compound, such that if the level obtained in the presence of the compound differs from that obtained in its absence, a compound capable of modulating the expression of the mammalian SM α-A regulatory region has been identified. Alterations in gene expression levels may be by any number of methods known to those of skill in the art e.g., by assaying for reporter gene activity, assaying cell lysates for mRNA transcripts, e.g. by Northern analysis or using other methods known in the art for assaying for gene products expressed by the cell.

In another embodiment, microdissection and transillumination can be used. These techniques offer a rapid assay for monitoring effects of putative drugs on SMC in transgenic animals containing an SM α-A regulatory region-driven reporter gene. In this embodiment, a test agent is delivered to the transgenic animal by any of a variety of methods. Methods of introducing a test agent may include oral, intradermal, intramuscular, intraperitoneal, intravenous, subcutaneous, intranasal and via scarification (scratching through the top layers of skin, e.g., using a bifurcated needle) or any other standard routes of drug delivery. The effect of such test compounds on the SMC can be analyzed by the microdissection and transillumination of the SMC. If the level of reporter gene expression observed or measured in the presence of the compound differs from that obtained in its absence, a compound capable of modulating the expression of the mammalian SM α-A regulatory region has been identified.

In various embodiments of the invention, compounds that may be used in screens for modulators of SMC-related disorders include peptides, small molecules, both naturally occurring and/or synthetic (e.g., libraries of small molecules or peptides), cell-bound or soluble molecules, organic, non-protein molecules and recombinant molecules that may have SM α-A regulatory region binding capacity and, therefore, may be candidates for pharmaceutical agents.

Alternatively, the proteins and compounds include endogenous cellular components which interact with SM α-A regulatory region sequences in vivo. Cell lysates or tissue homogenates may be screened for proteins or other compounds which bind to the SM α-A regulatory region, or fragment thereof. Such endogenous components may provide new targets for pharmaceutical and therapeutic interventions.

In one embodiment, libraries can be screened. Many libraries are known in the art that can be used, e.g., peptide libraries, chemically synthesized libraries, recombinant (e.g., phage display libraries), and in vitro translation-based libraries. In one embodiment of the present invention, peptide libraries may be used to screen for agonists or antagonists of SM α-A-linked reporter expression. Diversity libraries, such as random or combinatorial peptide or non-peptide libraries can be screened for molecules that specifically modulate SM α-A regulatory region activity. Random peptide libraries consisting of all possible combinations of amino acids attached to a solid phase support may be used to identify peptides that are able to activate or inhibit SM α-A regulatory region activities (Lam, K. S. et al., 1991, Nature 354:82–84). The screening of peptide libraries may have therapeutic value in the discovery of pharmaceutical agents that stimulate or inhibit the expression of SM α-A by interaction with the promoter region.

Examples of chemically synthesized libraries are described in Fodor et al., 1991, Science 251:767–773; Houghten et al., 1991, Nature 354:84–86; Lam et al., 1991, Nature 354:82–84; Medynski, 1994, BioTechnology 12:709–710; Gallop et al., 1994, J. Medicinal Chemistry 37(9):1233–1251; Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; Salmon et al., 1993, Proc. Natl. Acad. Sci. USA 90:11708–11712; PCT Publication No. WO 93/20242; and Brenner and Lerner, 1992, Proc. Natl. Acad. Sci. USA 89:5381–5383.

Examples of phage display libraries are described in Scott and Smith, 1990, Science 249:386–390; Devlin et al., 1990, Science, 249:404–406; Christian, et al., 1992, J. Mol. Biol. 227:711–718; Lenstra, 1992, J. Immunol. Meth. 152:149–157; Kay et al., 1993, Gene 128:59–65; and PCT Publication No. WO 94/18318 dated Aug. 18, 1994.

By way of example of non-peptide libraries, a benzodiazepine library (see e.g., Bunin et al., 1994, Proc. Natl. Acad. Sci. USA 91:4708–4712) can be adapted for use. Peptoid libraries (Simon et al., 1992, Proc. Natl. Acad. Sci. USA 89:9367–9371) also can be used. Another example of a library that can be used, in which the amide functionalities in peptides have been permethylated to generate a chemically transformed combinatorial library, is described by Ostresh et al. (1994, Proc. Natl. Acad. Sci. USA 91:11138–11142).

A specific embodiment of such an in vitro screening assay is described below. The SM α-A regulatory region-reporter vector is used to generate transgenic mice from which primary cultures of SM α-A regulatory region-reporter vector germ cells are established. About 10,000 cells per well are plated in 96-well plates in total volume of 100 μl, using medium appropriate for the cell line. Candidate inhibitors of SM α-A gene expression are added to the cells. The effect of the inhibitors of SM α-A gene activation can be determined by measuring the response of the reporter gene driven by the SM α-A regulatory region. This assay could easily be set up in a high-throughput screening mode for evaluation of compound libraries in a 96-well format that reduce (or increase) reporter gene activity, but which are not cytotoxic. After 6 hours of incubation, 100 μl DMEM medium +2.5% fetal bovine serum (FBS) to 1.25% final serum concentration is added to the cells, which are incubated for a total of 24 hours (18 hours more). At 24 hours, the plates are washed with PBS, blot dried, and frozen at −80° C. The plates are thawed the next day and analyzed for the presence of reporter activity.

In a preferred example of an in vivo screening assay, SMC derived from transgenic mice can be transplanted into mice with a normal or other desired phenotype (Brinster et al., 1994, Proc. Natl. Acad. Sci. USA 91:11298–302; Ogawa et al., 1997, Int. J. Dev. Biol. 41:111–12). Such mice can then be used to test the effect of compounds and other various factors on SMC-related disorders. In addition to the compounds and agents listed above, such mice can be used to assay factors or conditions that can be difficult to test using other methods, such as dietary effects, internal pH, temperature, etc.

Once a compound has been identified that inhibits or enhances SM α-A regulatory region activity, it may then be tested in an animal-based assay to determine if the compound exhibits the ability to act as a drug to ameliorate and/or prevent symptoms of a SMC-related disorder, including, but not limited to, atherosclerosis, coronary artery disease, hypertension, stroke, asthma and multiple gastrointestinal, urogenital and reproductive disorders.

The assays of the present invention may be first optimized on a small scale (ie., in test tubes), and then scaled up for high-throughput assays. The screening assays of the present invention may be performed in vitro, i.e., in test tubes, using purified components or cell lysates. The screening assays of the present invention may also be carried out in intact cells in culture and in animal models. In accordance with the present invention, test compounds which are shown to modulate the activity of the SM at-A regulatory region in vitro, as described herein, will further be assayed in vivo in cultured cells and animal models to determine if the test compound has the similar effects in vivo and to determine the effects of the test compound on SMC-related disorders.

5.4 Compositions and Methods for Therapeutic Use of SM α-A Nucleotides

SM α-A polynucleotides, or transcriptionally active fragments thereof, can be used to treat and/or prevent diseases, conditions or disorders that can be ameliorated by modifying the level or the expression of SM α-A, or a heterologous gene linked to an SM α-A regulatory region, in an SMC-specific manner. Described herein are methods for such therapeutic treatments.

The SM α-A regulatory region may be used to achieve tissue specific expression in gene therapy protocols. In cases where such cells are tumor cells, the induction of a cytotoxic product by the SM α-A regulatory region may be used in the form of cancer gene therapy specifically targeted to SMC tumor cells which contain trans-acting factors required for SM α-A expression. In this way, the SM α-A regulatory region may serve as a delivery route for a gene therapy approach to cancers involving SMC. Additionally, antisense, antigene or aptameric oligonucleotides may be delivered to cells using the presently described expression constructs. Ribozymes or single-stranded RNA also can be expressed in a cell to inhibit the expression of a target gene of interest. The target genes for these antisense or ribozyme molecules should be those encoding gene products that are essential for cell maintenance.

The SM α-A regulatory region, and transcriptionally active fragments thereof, of the present invention may be used for a wide variety of purposes, e.g., to down regulate SM α-A gene expression, or, alternatively, to achieve SMC-specific stage-specific expression of heterologous genes.

In one embodiment, for example, the endogenous SM α-A regulatory region may be targeted to specifically down-regulate expression of the SM α-A gene. For example, oligonucleotides complementary to the regulatory region may be designed and delivered to the cells. Such oligonucleotides may anneal to the regulatory sequence and prevent transcription activation. Alternatively, the regulatory sequence, or portions thereof, may be delivered to cells in saturating concentrations to compete for transcription factor binding. For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11:155–215. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In another embodiment, a gene therapy method for ameliorating SMC-related disorders is provided. SM α-A regulatory region sequences are introduced in the SMC and used to drive SMC-specific expression of drugs or toxins. The method comprises introducing an SM α-A regulatory region sequence operatively associated with a drug or toxin gene into the SMC.

In yet another embodiment, the invention provides a gene therapy method for treatment of cancer or other proliferative disorders. The SM α-A regulatory region is used to direct the expression of one or more proteins specifically in SM tumor cells of a patient. Such proteins may be, for example, tumor suppressor genes, thymidine kinase (used in combination with acyclovir), toxins or proteins involved in cell killing, such as proteins involved in the apoptosis pathway.

In still another embodiment, the invention provides a preventative gene therapy method for preventing and/or delaying the onset of SMC-related disorders. The SM α-A regulatory region is introduced in the SMC and used to drive SMC-specific expression of therapeutic compounds. The method comprises introducing an SM α-A regulatory region sequence operatively associated with a nucleic acid encoding a therapeutic compound into the SMC to prevent and/or delay the onset of SMC-related disorders. For example, the SM α-A regulatory region sequence operatively associated with a nucleic acid encoding a therapeutic compound (e.g., NO synthase or lipid trafficking agents) can be used to overexpress the therapeutic compound specifically within SMC to inhibit atherosclerotic lesion formation in coronary arteries, and/or promote stabilization of atherosclerotic plaques. Since new NMR and ultrasound methods are capable of being able to non-invasively detect plaques that are at risk, the present invention can be used to overexpress factors that could stabilize a plaque and, thus, prevent heart attacks.

Methods for introducing genes for expression in mammalian cells are well known in the field. Generally, for such gene therapy methods, the nucleic acid is directly administered in vivo into a target cell or a transgenic mouse that expresses a SM α-A regulatory region operably linked to a reporter gene. This can be accomplished by any method known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), by direct injection of naked DNA, by use of microparticle bombardment (e.g., a gene gun; Biolistic, Dupont), by coating with lipids or cell-surface receptors or transfecting agents, by encapsulation in liposomes, microparticles, or microcapsules, by administering it in linkage to a peptide which is known to enter the nucleus or by administering it in linkage to a ligand subject to receptor-mediated endocytosis (see e.g., Wu and Wu, 1987, J. Biol. Chem. 262:4429–4432), which can be used to target cell types specifically expressing the receptors. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992;

WO 92/22635 dated Dec. 23, 1992; WO92/20316 dated Nov. 26, 1992; WO93/14188 dated Jul. 22, 1993; WO 93/20221 dated Oct. 14, 1993). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342:435–438).

The oligonucleotide may comprise at least one modified base moiety which is selected from the group including, but not limited to: 5-fluorouracil, 5-bromouracil, 5-chlorouracil, 5-iodouracil, hypoxanthine, xanthine, 4-acetylcytosine, 5-(carboxyhydroxylmethyl) uraci, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

Endogenous target gene expression also can be reduced by inactivating or "knocking out" the SM α-A regulatory region using targeted homologous recombination (e.g., see Smithies et al., 1985, Nature 317:230–234; Thomas and Capecchi, 1987, Cell 51:503–512; Thompson et al., 1989, Cell 5:313–321; each of which is incorporated by reference herein in its entirety). For example, a mutant, non-functional target gene (or a completely unrelated DNA sequence) flanked by DNA homologous to the regulatory region of the SM α-A gene can be used, with or without a selectable marker and/or a negative selectable marker, to transfect cells that express the target gene in vivo. Insertion of the DNA construct, via targeted homologous recombination, results in inactivation of the SM α-A regulatory region. This approach can be adapted for use in humans provided the recombinant DNA constructs are directly administered or targeted to the required site in vivo using appropriate vectors.

In an alternative embodiment, endogenous target gene expression can be reduced by targeting deoxyribonucleotide sequences complementary to the SM α-A regulatory region to form triple helical structures that prevent transcription of the target gene in target cells in the body. (See generally, Helene, 1991, Anticancer Drug Des., 6(6):569–584; Helene et al., 1992, Ann. N.Y. Acad. Sci., 660:27–36; and Maher, 1992, Bioassays 14(12):807–815).

Nucleic acid molecules to be used in triple helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

In a specific embodiment, single-stranded deoxynucleotides are designed to target the 10 bp intronic CArG element located at +1001 bp relative to the start of transcription of the SM α-A regulatory region of SEQ ID NO:1. Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The anti-sense RNA and DNA molecules and triple helix molecules of the invention may be prepared by any method known in the art for the synthesis of nucleic acid molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the RNA molecule. Such DNA sequences may be incorporated into a wide variety of vectors which contain suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include, but are not limited to, the addition of flanking sequences of ribo- or deoxy-nucleotides to the 5' and/or 3' ends of the molecule or the use of phosphorothioate or 2' O-methyl rather than phospho-diesterase linkages within the oligodeoxyribonucleotide backbone.

The SM α-A regulatory region, and transcriptionally active fragments thereof, of the present invention can be used to express the SM α-A gene in an altered manner as compared to expression in a normal cell. The SM α-A regulatory region, and transcriptionally active fragments thereof, of the present invention also can be used to achieve tissue specific expression of a target gene. Thus, it is possible to design appropriate therapeutic and diagnostic techniques directed to this regulatory sequence in order to modulate the expression of a target gene. In accordance with the present invention, the term "modulate" encompasses the suppression or augmentation of expression of a target gene and also encompasses the tissue specific suppression or expression of a target gene. When a cell proliferative disorder is associated with underexpression or overexpression of an SM α-A gene product, oligonucleotide based compounds such as those described herein, including antisense oligonucleotides, may be used to modulate expression of the SM α-A gene. For example, where the associated disorder is cancer, the induction of a cytotoxic gene product utilizing the SM α-A regulatory region may be used as a cancer therapy. One of skill in the art can determine if a particular therapeutic course of treatment is successful by several methods known to those of skill in the art, including muscle fiber analysis or biopsy.

5.4.1 Inhibitory, Antisense, Ribozyme and Triple Helix Approaches

In another embodiment, symptoms of disorders involving SMC may be ameliorated by decreasing the level of SM α-A regulatory region activity by using well-known antisense, gene "knock-out," ribozyme and/or triple helix methods to decrease the level of SM α-A regulatory region expression. Among the compounds that exhibit the ability to modulate the activity, expression or synthesis of the SM α-A regulatory region, including the ability to ameliorate the symptoms of a SMC-related disorder are antisense, ribozyme and triple helix molecules. Such molecules may be designed to reduce or inhibit either unimpaired, or if appropriate, mutant SM α-A regulatory region activity. Techniques for the production and use of such molecules are well known to those of skill in the art.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarity, although preferred, is not required.

A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In one embodiment, oligonucleotides complementary to non-coding regions of the gene of interest could be used in an antisense approach to inhibit translation of endogenous mRNA. Antisense nucleic acids should be at least six nucleotides in length, and are preferably oligonucleotides ranging from 6 to about 50 nucleotides in length. In specific aspects, the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit target gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, erg., Letsinger, et al., 1989, Proc. Natl. Acad. Sci. U.S.A. 86:6553–6556; Lemaitre, et al., 1987, Proc. Natl. Acad. Sci. U.S.A. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., 1988, BioTechniques 6:958–976) or intercalating agents (see, e.g., Zon, 1988, Pharm. Res. 5:539–549). To this end, the oligonucleotide may be conjugated to another molecule, e.g. a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An α-anomeric oligonucleotide forms specific double-stranded hybrids with complementary RNA in which, contrary to the usual β-units, the strands run parallel to each other (Gautier, et al., 1987, Nucl. Acids Res. 15:6625–6641). The oligonucleotide is a 2'-0-methylribonucleotide (Inoue, et al., 1987, Nucl. Acids Res. 15:6131–6148), or a chimeric RNA-DNA analogue (Inoue, et al., 1987, FEBS Lett. 215:327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein, et al. (1988, Nucl. Acids Res. 16:3209), methylphosphonate oligonucleotides can be prepared by use of controlled pore glass polymer supports (Sarin, et al., 1988, Proc. Natl. Acad. Sci. U.S.A. 85:7448–7451), etc.

While antisense nucleotides complementary to the target gene coding region sequence could be used, those complementary to the transcribed, untranslated region are most preferred.

Antisense molecules should be delivered to cells that express the target gene in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

A preferred approach to achieve intracellular concentrations of the antisense sufficient to suppress translation of endogenous mRNAs utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, *Nature* 290:304–310), the promoter contained in the 3' long terminal repeat of Rous sarcoma virus (Yamamoto, et al., 1980, *Cell* 22:787–797), the herpes thymidine kinase promoter (Wagner, et al., 1981, *Proc. Natl. Acad. Sci. U.S.A.* 78:1441–1445), the regulatory sequences of the metallothionein gene (Brinster, et al., 1982, *Nature* 296:39–42), etc. Any type of plasmid, cosmid, YAC or viral vector can be used to prepare the recombinant DNA construct which can be introduced directly into the tissue site. Alternatively, viral vectors can be used that selectively infect the desired tissue, in which case administration may be accomplished by another route (e.g., systemically).

Ribozyme molecules designed to catalytically cleave target gene mRNA transcripts can also be used to prevent translation of target gene mRNA and, therefore, expression of target gene product. (See, e.g., PCT International Publication WO90/11364, published Oct. 4, 1990; Sarver, et al., 1990, *Science* 247, 1222–1225).

Ribozymes are enzymatic RNA molecules capable of catalyzing the specific cleavage of RNA. (For a review, see Rossi, 1994, *Current Biology* 4:469–471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers, 1995, *Molecular Biology and Biotechnology: A Comprehensive Desk Reference*, VCH Publishers, New York, (see especially FIG. 4, page 833) and in Haseloff and Gerlach, 1988, *Nature,* 334:585–591, which is incorporated herein by reference in its entirety.

Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in *Tetrahymena thermophila* (known as the IVS, or L-19 IVS RNA) and that has been extensively described by Thomas Cech and collaborators (Zaug, et al., 1984, *Science,* 224:574–578; Zaug and Cech, 1986, *Science,* 231:470–475; Zaug, et al., 1986, *Nature,* 324:429–433; published International patent application No. WO 88/04300 by University Patents Inc.; Been and Cech, 1986, *Cell,* 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes unlike antisense molecules, are catalytic, a lower intracellular concentration is required for efficiency.

Endogenous target gene expression can also be reduced by inactivating or "knocking out" the target gene or its promoter using targeted homologous recombination (e.g., see Smithies, et al., 1985, *Nature* 317:230–234; Thomas and Capecchi, 1987, *Cell* 51:503–512; Thompson, et al., 1989, *Cell* 5:313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas and Capecchi, 1987 and Thompson, 1989, supra). However this approach can be adapted for use in humans provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body. (See generally, Helene, 1991, *Anticancer Drug Des.*, 6(6):569–584; Helene, et al., 1992, *Ann. N.Y. Acad. Sci.*, 660:27–36; and Maher, 1992, *Bioassays* 14(12):807–815).

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may, be introduced into cells via gene therapy methods such as those described, below, in Section 5.4.2 that do not contain sequences susceptible to whatever antisense, ribozyme, or triple helix treatments are being utilized. Alternatively, in instances whereby the target gene encodes an extracellular protein, it may be preferable to co-administer normal target gene protein in order to maintain the requisite level of target gene activity.

Anti-sense RNA and DNA, ribozyme and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

5.4.2 Gene Replacement Therapy

The nucleic acid sequences of the invention, described above in Section 5.1, can be utilized for transferring recombinant nucleic acid sequences to cells and expressing said sequences in recipient cells. Such techniques can be used, for example, in marking cells or for the treatment of a disorder involving SMC. Such treatment can be in the form of gene replacement therapy. Specifically, one or more copies of a normal gene or a portion of the gene that directs the production of a gene product exhibiting normal gene function, may be inserted into the appropriate cells within a patient, using vectors that include, but are not limited to adenovirus, adeno-associated virus and retrovirus vectors, in addition to other particles that introduce DNA into cells, such as liposomes.

In one embodiment, techniques for delivery involve direct administration, e.g., by stereotactic delivery of such gene sequences to the site of the cells in which the gene sequences are to be expressed.

Additional methods that may be utilized to increase the overall level of gene expression and/or gene product activity include using targeted homologous recombination methods, as discussed above, to modify the expression characteristics of an endogenous gene in a cell or microorganism by inserting a heterologous DNA regulatory element such that the inserted regulatory element is operatively linked with the endogenous gene in question. Targeted homologous recombination can thus be used to activate transcription of an endogenous gene that is "transcriptionally silent", i.e., is not normally expressed or is normally expressed at very low levels, or to enhance the expression of an endogenous gene that is normally expressed.

Further, the overall level of target gene expression and/or gene product activity may be increased by the introduction of appropriate target gene-expressing cells, preferably autologous cells, into a patient at positions and in numbers that are sufficient to ameliorate the symptoms of a SMC-related disorder. Such cells may be either recombinant or non-recombinant.

When the cells to be administered are non-autologous cells, they can be administered using well known techniques that prevent a host immune response against the introduced cells from developing. For example, the cells may be introduced in an encapsulated form which, while allowing for an exchange of components with the immediate extracellular environment, does not allow the introduced cells to be recognized by the host immune system.

Additionally, compounds, such as those identified via techniques such as those described above that are capable of modulating activity of a SM α-A regulatory region can be administered using standard techniques that are well known to those of skill in the art.

5.5 Pharmaceutical Preparations and Methods of Administration

The compounds that are determined to modify SM α-A regulatory region activity or gene product activity can be administered to a patient at therapeutically effective doses to treat or ameliorate a SMC-related disorder. A therapeutically effective dose refers to that amount of the compound sufficient to result in amelioration of symptoms of such a disorder.

5.5.1 Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

5.5.2 Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In certain embodiments, it may be desirable to administer the pharmaceutical compositions of the invention locally to the area in need of treatment. This may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

For topical application, the compounds may be combined with a carrier so that an effective dosage is delivered, based on the desired activity.

In addition to the formulations described previously, the compounds also may be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

6. EXAMPLE

Delineation of a Regulatory Region within the 5' and First Intron of SM α-Actin Sufficient for SM-specific Expression In Vivo

6.1 Materials and Methods

6.1.1 Construction of Rat SM α-Actin Lac Z Reporters

The pUC19-Lac Z plasmid used to generate reporter gene constructs was a generous gift of Dr. Eric Olsen (See also, Acc. No. V00296). Several deletion constructs were generated for analysis in transgenic mice. The p125/Lac Z, p547/Lac Z, and p2800/Lac Z reporters were made by subcloning the corresponding promoter regions from previously described CAT reporter constructs (Shimizu R T, et al., *J. Biol. Chem.* 1995;270:7631–7643) into the Lac Z vector after HindIII/Xba I restriction digestion. Constructs containing the first intron, p547Int/Lac Z and p2600Int/Lac Z, were subcloned from a larger genomic fragment isolated and described previously using PmII/Xho I and Sca I/Xho I digestion, respectively.

CArG mutations in the p2600Int/Lac Z construct were made using the PCR based Excite method (Promega) as per protocol. To avoid potential PCR-induced mutations in the Lac Z reporter, the promoter was subcloned into pBluescript, and after the mutagenesis protocol, returned to the Lac Z vector. The oligonucleotides used to make these mutations contained the following sequences, all of which have been shown to abolish SRF binding in gel shift analyses (mutated sequences are in italics); A mut, 5'-aattgtttaa-3' (SEQ ID NO:11); B mut, 5'-ccctatatca-3' (SEQ ID NO:12); Int mut, 5'-aataattaaa-3 ' (SEQ ID NO:13).

Site directed mutants mPPI gata and mPPI AP1 were generated by the excite method (Promega) as per protocol using the PPI construct as a template (see FIG. 10B for the mutant sequences). The intron fragments #2, 100 and 300 were PCR generated and then ligated (Kpn I) to the pProm construct to create PPInt#2, PPInt100 and PPInt300.

Final subcloning steps and all mutations were verified by direct DNA sequencing. Before transgenic injections, all constructs were tested for Lac Z expression by transient transfection into cultured rat aortic SMC cultures to ensure functional activity of all constructs. All clones, including those containing CArG mutations, showed at least some activity in these assays.

6.1.2 Generation and Analysis of Transgenic Mice

All constructs were prepared for transgenic injection by removal of pUC19 backbone sequences by NotI/EcoRI digestion and subsequent agarose gel purification of the linearized promoter/Lac Z fragment. Transgenic mice were generated using standard methods (Li L, et al., *J Cell Biol.* 1996;132:849–859; Gordon J W, et al.,*Science,* 1981;214:1244–1246) either commercially (DNX, Princeton, N.J.), or within the transgenic core facility at The University of Virginia, Charlottesville. Mice were analyzed transiently at several embryonic stages or by establishing founder lines that allowed more detailed analysis of transgene expression throughout development and in adult animals. Transgene presence was analyzed by PCR using genomic DNA purified from placentas (transients) or tail clips (founders) according to the method of Vemet (Vemet M, et al., *Methods Enzymol.* 1993;225:434–451). Mice were euthanized by IP injection of pentobarbital (100 mg/kg), and transgene expression and histological analysis were performed as previously described (Li L, et al., *J. Cell Biol.* 1996;132:849–859; Cheng T C, et al.; *Science,* 1993;261:215–218).

6.1.3 Cell Culture, Transient Transfections and Reporter Gene Assays

SMCs from rat thoracic aorta were isolated and cultured as previously described (Blank R S, et al., *J. Biol Chem.* 1992;267:984–989). SMCs were seeded into 6-well plates and transfected 24 h after plating at 70–80% confluency. Transfections were performed using 4 µg of plasmid DNA and the transfection reagent, DOTAP (Boehringer Mannheim). Growth conditions and preparation of cell lysates for measurement of Lac Z activity were performed as previously described (Shimizu R T, et al., *J. Biol Chem.* 1995;270:7631–7643). The enzyme activity of each sample was normalized to the protein concentration of each cell lysate as measured by the DC protein assay (BioRad). In each experiment, the promoterless Lac Z construct was also transfected to serve as the base-line indicator of Lac Z activity, and the activity of each promoter construct is expressed relative to promoterless activity. All activities represent at least 3 independent experiments, with each construct tested in triplicate per experiment. Relative Lac Z activities are expressed as the mean ±S.D. computed from the results obtained from each set of transfection experiments. Cotransfection of a viral promoter/reporter construct as a control for transfection efficiency was not performed since it has previously been shown that such constructs exhibit unknown and variable squelching effects on the SM α-actin promoter presumably due to competition for common transcription factors (Shimizu R T, et al., *J. Biol Chem.* 1995;270:7631–7643). Moreover, it has previously been shown that inclusion of such controls are unnecessary in that variations in transfection efficiency between independent experimental samples is routinely very small (<10%) (Shimizu R T, et al., *J. Biol Chem.* 1995;270:7631–7643).

6.1.4 Preparation of Nuclear Extracts, In Vitro Synthesis of SRF, and Electromobility Shift Assays Nuclear extracts were prepared from confluent rat aortic SMCs using the methods of Dignam (Dignam J D, et al., *Nucleic Acids Res.* 1983;11:1475–1489). Culture conditions matched those used for transient transfection assays. Oligonucleotides used in EMSAs were purchased commercially (Operon Technologies) and include the following: CArG A, 5'-ttgctccttgtttgggaagc-3' (SEQ ID NO:14); CArG B, 5'-gaggtccctatatggttgtg-3' (SEQ ID NO:15); Intronic CArG, 5'-ttttacctaattaggaaatg-3' (SEQ ID NO:16). Probes were $^{32}$P end labeled and annealed. All probes were purified on a 6% acrylamide gel, eluted in TE, and precipitated twice in ethanol.

EMSAs were performed with 20 µl of binding reaction that included=30 pg of labeled probe, 5 µg of SMC nuclear extract 0.2 to 0.6 µg of poly (dI-dC) in 1×binding buffer (10 mM TrisHCl (pH 7.5), 100 mM KCI, 50 mM NaCl, 1 mM dithiothreitol, 1 mM EDTA, and 5% glycerol). Following a 30 min incubation at room temperature, the samples were subjected to electrophoresis on a 5% polyacrylamide gel, which had been pre-run at 170V for 1 hr. Electrophoresis was performed at 170V in 0.5×TBE (45 mM Tris Borate, 1 mM EDTA). Gels were dried and exposed to film for 24–72 h at −70 ° C. For supershift studies, 1 µl of SRF antibody was added after the 30 min incubation period and the reaction was incubated for an additional 15 min and then loaded onto the gel for electrophoresis.

6.1.5 Immunohistochemical Staining of SM α-actin Expression

Embryos were fixed overnight in formalin. Tissues were dehydrated, incubated in 100% xylene, and embedded in paraffin. Thin sections (6 µm) were placed on uncoated slides and dried on a slide warmer. Sections were cleared in 100% xylene and rehydrated through a graded ethanol series to a final incubation in PBS. Endogenous peroxidase activity was quenched by incubating slides in methanol containing 0.3% hydrogen peroxide for 30 min. Slides were subsequently rehydrated in PBS and blocked in a 1:50 solution of normal goat serum made up in PBS. Sections were then incubated with SM α-actin primary antibody for 1 hour and washed with three changes of PBS. Detection of primary antibody was performed using a Vectastain ABC kit (Vector Laboratories) according to the manufacturers instructions with 3,3'-diaminobenzidine (DAB) as the chromagen.

6.2 Results 6.2.1 The SM α-Actin Promoter Region from −2, 600 through the First Intron Conferred In Vivo Expression of a LacZ Reporter in a Manner Similar to that of the Endogenous Gene Previous results from transient transfections into rat aortic SMC cultures demonstrated that reporter constructs containing the first 547 bps of the SM α-actin 5' promoter were expressed at high levels only in SMC or other muscle cells that are known to express their endogenous SM α-actin gene (Shimizu R T, et al., *J. Biol Chem.*, 1995;270:7631–7643). Therefore, the present transgenic mouse studies were initiated using a construct that contained this promoter region (FIG. 1; construct A). FIG. 2A shows a p547/Lac Z positive embryo at E 13.5, a time point when SM α-actin is expressed in skeletal, cardiac, and smooth muscle. Results show that this promoter region was sufficient to drive transgene expression in skeletal and cardiac muscle, but not in the vasculature or in any other SMC tissue. In subsequent studies, similar results were obtained with a construct containing 2,800 bps of the 5' promoter region.

The preceding observations indicated that additional regions of the SM α-actin gene were necessary for expression of SM α-actin in SMC in vivo, Nakano (Nakano Y, et al., *Gene.* 1991 ;99:285–289) previously reported that the first intron of the human gene had significant enhancer activity in cultured SMC, an observation consistent with present observations for the rat first intron (see FIG. 4). Constructs were generated from a genomic clone that included the first intron and 547 or 2,600 bps of the 5' promoter (FIG. 1; constructs B and C). Results shown in FIG. 2B demonstrate that p547Int/Lac Z, like the p547 construct, was expressed highly in embryonic cardiac and skeletal muscle. However, in addition, all independent transgenic founder embryos (E 13.5) generated with this construct (n=8) expressed high levels of Lac Z in the umbilical arteries and half showed expression in the lower portion of the abdominal aorta. These data demonstrate that the addition of the first intron to 547 bps of the 5' promoter promoted transgene expression in only a small subset of SMC.

A transgenic construct containing sequences from −2,600 through the first intron (p2600Int/Lac Z) was next tested. Results shown in FIG. 2C demonstrated that this construct was expressed at E 13.5 in a pattern that closely followed expression of the endogenous SM α-actin gene with staining in heart and skeletal muscle as well as in multiple SM tissues including the aorta, carotids, multiple small and large arteries, esophagus, stomach, intestines, bladder, ureter, and airway smooth muscle. Examination of histological sections from p2600Int/Lac Z animals at E 10.5–16.5 showed that Lac Z staining was highly restricted to the vasculature or the SMC layers of smooth muscle containing organs as well as to cardiac and skeletal muscle. FIG. 3 shows representative sections at E 16.5 with panel 5D showing immunohistochemical detection of SM α-actin expression for comparison. FIG. 4 shows p2600Int/Lac Z expression in various organs taken from adult mice 4–6 weeks of age. Lac Z staining was seen in nearly all adult SM tissues examined including; the esophagus, stomach, intestines, bladder, trachea, bronchi, and most blood vessels including the coronary, mesenteric, and renal vascular beds. Histological sections taken from adult tissues are shown in FIG. 5. Note that expression was completely restricted to SMC, and that the p2600Int/LacZ transgene which was highly expressed in skeletal and cardiac muscle during embryonic development, was no longer expressed in the adult skeletal or cardiac muscle cells. The latter observation is consistent with the absence of expression in these tissues in the adult animals and indicates that the −2,600 to +2784 promoter region tested is sufficient to confer appropriate developmental regulation of this gene in multiple cell types. Expression in most structures was found to be very homogeneous with most, if not all, SMC being stained. This is in contrast to previous observations with certain SM MHC and SM 22 promoter constructs suggesting that the p2600lnt/Lac Z transgene also contains sufficient information to drive expression in SMC subtypes that have been shown to differentially express SM-22 or SM MHC transgenic constructs within a given SMC tissue.

A total of ten independent founder lines were established with the p26001Int/Lac Z construct. Of these, six showed expression patterns during embryonic development and as adults that virtually mimicked expression of the endogenous SM α-actin gene with two exceptions. Only one founder exhibited expression in uterine SMC, and most founders showed relatively low expression in small cranial arteries during development. In adult animals, however, expression was consistently detected in the basilar artery and other cerebral vessels in each of these six independent founders suggesting developmental signals may be important for expression of the p2600Int/Lac Z transgene in some SMC subtypes. Of the 4 remaining founders; two showed high expression in all vascular SMC but only limited expression in SM-containing organs, one was expressed only in cardiac and skeletal muscle during development, and one was expressed only in a small subset of skeletal muscle in the head and neck. These results indicate that the insertion site had only minor effects on expression of the p2600Int/Lac Z construct in most SMC. This provides strong evidence that the observed expression pattern was the result of sequences contained within the p2600Int/LacZ construct and not insertional locus.

6.2.2 CArG Mutations Attenuated the Activity of p2600Int/Lac Z Activity in Cultured SMCs Previous studies have shown that CArGs A and B when contained within a construct containing either 125 or 547 bps of the 5' promoter region are absolutely required for expression in SMC cultures (Shimizu R T, et al., *J. Biol Chem.* 1995;270:7631–7643). However, the transgenic results shown above demonstrate that additional sequences, including the CArG containing first intron, are required for expression in vivo. Therefore, to measure the transcriptional activity of the first intron, and to test the effects of mutations to CArGs A, B, and the intronic CArG in the context of the promoter region shown to be sufficient for in vivo expression, cultured rat SMC were transfected with equimolar amounts of the deletion or site-directed mutant constructs shown in FIG. 6. Results demonstrated that the first intron had significant transcriptional activity in the −547 and −2600 context, and that mutation of either CArG A, B, or the intronic CArG greatly decreased p2600lnt/LacZ activity in cultured SMC.

6.2.3 Serum Response Factor Bound the Intronic CarG

EMSA supershift analysis was performed to test whether the intronic CArG, like CArGs A and B, binds SRF. Results demonstrated that SRF bound to the intronic CArG. In fact, the intronic CArG binds SRF more avidly than CArGs A and B, a result consistent with the fact that these CArGs contain a conserved G or C substitution in their internal A/T rich nucleotide region (Shimizu R T, et al., *J. Biol Chem.* 1995;270:7631–7643) and that such substitutions lower SRF binding affinity(Santoro I M, et al., *Mol. Cell Biol.* 1991;11:6296–6305).

6.2.4 CArG B was Required for Expression of the p2600Int/LacZ Transgene in Skeletal, Cardiac, and Smooth Muscle at Embryonic Day 13.5 while the Intronic CArG was required only in SMC Results from the transgenic analyses of the SM α-actin promoter demonstrated that the first intron was required for transgene expression in SMC. Taken together with the cell culture studies described above, these results suggest that the intronic CArG, and perhaps CArGs A and B, are required for SMC expression of SM α-actin in vivo. CArG mutations were therefore tested to see if they affected expression of the p2600Int/LacZ transgene in developing embryos and in adult mice. At least 5 independent founder lines were generated for each CArG mutant construct. Results shown in FIG. 7 compare the effects of CArG mutations on LacZ expression in mouse embryos at E 13.5 when the endogenous SM α-actin gene and the p2600Int/LacZ transgene (Wt) is expressed in all three muscle cell types. Mutation of CArG B (B mut) completely abolished LacZ expression in all three muscle cell types indicating that it is absolutely required for SM α-actin expression. Of major significance, mutation of the intronic CArG (Int mut) had no effect on cardiac or skeletal muscle expression, but completely abolished expression in all SM tissues indicating that it is required for expression in SMC but not in cardiac and skeletal muscle. Mutation of CArG A had no visible effect on staining in skeletal or heart muscle, but reduced or eliminated staining in some SM tissues. However, these effects varied somewhat between founders suggesting that the activity of this construct was somewhat sensitive to the site of transgene insertion.

6.2.5 Mutations to CArG B and the Intronic CArG Abolished Expression of the p2600Int/LacZ Transgene in SMC in Adult Mice To determine whether CArG elements are also required for expression in adult mice, expression of the wild-type p2600lnt/Lac Z transgene construct and respective CArG mutants in 4–6 week old mice (FIG. 8) were compared. Results demonstrated that mutation of CArG B or the intronic CArG abolished expression in SMC from all tissues including, trachea, lung, bladder, stomach and intestines and from all blood vessels including the aorta, carotids, and coronary mesenteric, renal, and skeletal muscle arteries. Interestingly, mutation of CArG A eliminated expression in smooth muscle organs and large vessels such as the aorta and carotids, but only partially inhibited expression in smaller arterioles.

6.2.6 The conserved Intronic Region Contains Positive and Negative Regulatory Activities A series of studies on the 330 bp conserved region within the first intron (from about +770 to about +1100) were performed to identify potentially important regulatory elements. Results shown in FIGS. 9 and 11 demonstrate that this intronic fragment contains both positive and negative regulatory regions. Specifically, the ~100 bp region from +937 to +1,041 that contains the intronic CArG had significant positive activity when spliced downstream of the 5' promoter (compare PPInt100 with pProm) while an adjacent fragment from +863 to +990 (PPInt#2) significantly inhibited pProm activity (FIG. 9). Other important protein binding regions have been identified by DNase footprinting that have significant homology to known cis regulatory elements that bind AP1and the GATA family of transcription factors. Mutation of the highly conserved AP1-like or GATA elements (see FIG. 10) in the context of the PPInt transgene caused a 35% and 65% reduction in promoter activity, respectively (FIG. 11). Still other regulatory elements, including, but not limited to, MCAT elements and transforming growth factor-β control elements, have been found within the SM α-actin regulatoy region (Swartz E A, et al., 1998, *Am. J. Physiol.,* 275 (2 Pt 1):C608–18).

6.3 Discussion

Results of the present examples demonstrate that the SM α-actin first intron is required for expression of a Lac Z transgene in SMC and that the promoter regions from −2,600 through the first intron were sufficient to drive transgene expression in a pattern virtually identical to that of the endogenous gene. The present invention also provides clear evidence that SM α-actin expression is CArG dependent, and that SMC-specific regulation requires unique cooperative interactions between the intronic CArG and CArGs A and B.

Results of the present transgenic analyses illustrated a number of interesting features of SM α-actin gene regulation that both confirm and extend previous observations in cultured SMC, but also point out some key differences. Previous studies demonstrated that 2,800 bps of the SM α-actin 5' promoter were sufficient to drive high level expression of SM α-actin only in cultured SMC or other cell types such as L6 myotubes that are known to express their endogenous gene (Blank R S, et al.; *J Biol Chem.* 1992;267:984–989; Shimizu R T, et al.; *J Biol Chem.* 1995;270:7631–7643). In contrast, this same construct was completely inactive in a variety of cell types such as endothelial cells and AKR2B fibroblasts that do not express SM α-actin(Shimizu R T, et al.; *J Biol Chem.* 1995;270:7631–7643). The results presented in the present example demonstrated that neither the p2800/Lac Z nor the p547/Lac Z transgenes were expressed in SMC in vivo. These same constructs, however, were expressed highly in embryonic skeletal and heart muscle which are known to express SM α-actin during embryonic development. These results highlight the fact that regulation of expression of the SM α-actin gene is cell-type-specific, and also emphasize the critical importance of studying SMC gene regulation in transgenic animals in order to reproduce complex local environmental cues (i.e. matrix interactions, neuronal and hormonal input, mechanical stresses, etc.) that are necessary for SMC differentiation but which cannot be accurately simulated in SMC cultures.

More extensive promoter analyses revealed that both the first intron and sequences from −547 to −2,600 contain promoter elements that are required for transgenic expression in SMC. The fact that the p547/Lac Z and p2800/Lac Z constructs were expressed in embryonic skeletal and cardiac muscle but not in SMC indicates that SM α-actin expression in these tissues is differentially regulated depending upon muscle cell type. It is possible that cardiac and skeletal muscle contain additional trans acting factors that regulate expression in these cell types, or that the sequences that are required for expression in SMC (i.e. the first intron and from −547 to −2,600) mediate the positive activity of SMC-specific trans acting factors.

Because of the qualitative nature of Lac Z analysis in transgenic animals, the possibility of insertional variegation, and known SMC heterogeneity, considerable caution must be employed when analyzing expression patterns between different transgenic promoters and even between independent founder lines containing the same transgene. Nevertheless, it is interesting that expression of the p2600lnt/Lac Z transgene was readily detected in nearly all SM tissues in 6 out of 10 independent founder lines, and expression in those lines was remarkably homogeneous both between and within SMC populations. Recently published transgenic studies using other SMC marker gene promoters resulted in considerably different patterns of SMC expression and provided evidence for significant SMC heterogeneity. For example, a transgene driven by 441 or 1110 bps of the SM-22 5' promoter. although expressed in arterial SMC, was not expressed in any other SM tissues (Kim S, et al., *Mol Cell Biol.* 1997;17:2266–2278; Li L, et al., *Dev Biol.* 1997;187:311–321). In addition, a Lac Z transgene construct under the control of the SM MHC promoter region from −4,299 through +11,600 was expressed in most SMC tissues but showed significant heterogeneity between SMC within the same tissue (Madsen C S, et al., *Circ Res.* 1998;82:908–917). Although the present data may reflect the relative strength of the SM α-actin promoter, it also indicates that SMC from nearly all lineages share at least some common transcriptional regulatory programs. Such SMC-specific high-level expression should make the SM α-actin promoter an attractive vector for use in cardiovascular gene therapy.

The present report is the first to report the activity of the SM α-actin CArG elements in vivo and provide several interesting findings concerning CArG-dependent regulation of SM α-actin expression. First, CArG B was absolutely required for in vivo expression in all three muscle cell types and may provide transcriptional activity in skeletal and cardiac muscle during embryonic development. Second, CArG A which is a much weaker CArG in that it binds SRF poorly, was required for expression in nearly all SMC tissues except for the smaller resistance vessels (see FIG. 8). This may represent previously undescribed lineage differences between large and small vessels but may also be the result of known differences in hemodynamic and/or other environmental stresses that could possibly regulate SM α-actin expression independent of CArG A. The effects of the CArG A and B mutations on in vivo expression of the SM α-actin transgene are somewhat analogous to the effects of mutations to the "near" (−141) and "far" (−264) CArGs described in the SM-22 promoter(Kim S, et al.,*Mol Cell Biol.* 1997;17:2266–2278; Li L, et al., *Dev Biol.* 1997;187:311–321). In those studies, mutation of the "strong" near CArG abolished expression in all cell types while mutation of the much "weaker" far CArG had only limited effects on expression. Finally, the intronic CArG functions as a SMC-specific enhancer-like element affecting expression in SMC but not in embryonic skeletal and cardiac muscle. SRF was shown to bind intronic CArG more avidly than both CArGs A and B (see FIG. 6), and it may be that in SMC, SRF binding to the SM α-actin promoter may be rate limiting making the presence of the strong intronic CArG required for in vivo expression. It is also possible that the intronic CArG, or other elements within the first intron that interact with the intronic CArG, recruit SMC-specific factors that are required for SM α-actin expression in vivo. Although such a factor was not detected in the gel shift analyses, this was not surprising since only a 20 bp intronic CArG oligo was used as shift probes.

The requirement for multiple CArGs for p2600IntLac Z expression in SMC and the fact that the CArGs have differential effects in SMC versus non-SMC indicates that these elements act interdependently in vivo to regulate SM α-actin expression. Recent evidence demonstrated that CArG phasing and spacing is an important determinant in the activity of a reporter construct containing the first 125 bp of the 5' promoter suggesting that CArGs A and B coordinate the formation of a transcription activation complex sufficient to drive expression at least in SMC cultures. The in vivo requirement for the intronic CArG suggests that this model is probably more complex. Indeed, it has been shown that the highly conserved intronic region functions only in one orientation which argues that it also has specific structural requirements important for transcription complex assembly or activation. Moreover, the results of the present examples demonstrate that numerous regulatory elements exist within the conserved 325 bp intronic region.

Taken together, the present specification is the first report to provide evidence that CArG, AP-1-like and GATA-like elements play a critical role in transcriptional regulation of the SM α-actin gene in vivo, and that they exhibit differential activity in SMC versus non-SMC.

The invention described and claimed herein is not to be limited in scope by the specific embodiments herein disclosed since these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

All publications, patents and patent applications mentioned in this specification are herein incorporated by reference to the same extent as if each individual publication, patent or patent application was specifically and individually indicated to be incorporated by reference.

What is claimed is:

1. An isolated polynucleotide comprising nucleotides 3331–3656, 3495–3599 or 3421–3548 of SEQ ID NO: 1 spliced downstream of nucleotides 1–2558 of SEQ ID NO: 1.

2. An isolated polynucleotide comprising a smooth muscle (SM) α-A promoter/enhancer in operable association with a heterologous polynucleotide, wherein the promoter/enhancer comprises sufficient sequence from the first intron of the SM α-A gene to confer smooth muscle cell-specific expression in vivo and wherein the promoter/enhancer comprises a nucleic acid that hybridizes to the complement of SEQ ID NO:1 when DNA comprising the complement of SEQ ID NO:1 is hybridized in 0.5 M NaHPO4, 7% sodium dodecyl sulfate (SDS), 1 mM EDTA at 65° C., and washed in 0.1×SSC/0.1% SDS at 68° C.

3. The isolated polynucleotide of claim 2, wherein the sequence from the first intron comprises the rat AP1-like, Int CArG and GATA elements, wherein the AP1-like element comprises SEQ ID NO:26;

the Int CArG element comprises SEQ ID NO:16; and the GATA element comprises SEQ ID NO:31.

4. The isolated polynucleotide of claim 2, wherein the sequence from the first intron comprises SEQ ID NO:8.

5. The isolated polynucleotide of claim 2, wherein the promoter/enhancer comprises the CArG B and CArG A elements depicted in SEQ ID NO:15 and SEQ ID NO:14, respectively.

6. The isolated polynucleotide of claim 2, wherein the promoter/enhancer comprises the sequence depicted in SEQ ID NO:4.

7. A vector comprising the polynucleotide of claim 2.

8. An isolated genetically-engineered host cell comprising a polynucleotide comprising a SM α-A promoter/enhancer in operable association with a heterologous polynucleotide, wherein the promoter/enhancer comprises sufficient sequence from the first intron of the SM α-A gene to confer smooth muscle cell-specific expression in vivo and wherein the promoter/enhancer comprises a nucleic acid that hybridizes to the complement of SEQ ID NO:1 when DNA comprising the complement of SEQ m NO:1 is hybridized in 0.5 M NaHPO4, 7% sodium dodecyl sulfate (SDS), 1 mM EDTA at 65° C., and washed in 0.1×SSC/0.1% SDS at 68° C.

9. The host cell of claim 8, wherein the sequence from the first intron comprises the rat AP1-like, Int CArG and GATA elements wherein the AP1-like element comprises SEQ ID NO:26;

the Int CArG element comprises SEQ ID NO:16; and the GATA element comprises SEQ ID NO:31.

10. The host cell of claim 8, wherein the promoter/enhancer comprises the nucleotide sequence of SEQ ID NO:1.

11. The host cell of claim 8, wherein the sequence from the first intron comprises SEQ ID NO:8.

12. The host cell of claim 8, wherein the promoter/enhancer comprises the CArG B and CArG A elements depicted in SEQ ID NO:15 and SEQ ID NO:14, respectively.

13. The host cell of claim 8, wherein the promoter/enhancer comprises the sequence depicted in SEQ ID NO:4.

14. The isolated polynucleotide of claim 2, wherein the promoter/enhancer comprises nucleotides 1–2605, 2011–2605, 2011–5342, 3331–3656, 3421–3548 or 3495–3599 of SEQ ID NO:1.

15. The isolated polynucleotide of claim 2, wherein the promoter/enhancer comprises the nucleotide sequence of SEQ ID NO:1.

* * * * *

SEQUENCE LISTING

```
<160> NUMBER OF SEQ ID NOS: 32

<210> SEQ ID NO 1
<211> LENGTH: 5342
<212> TYPE: DNA
<213> ORGANISM: Rattus sp.
<220> FEATURE:
<223> OTHER INFORMATION: smooth muscle alpha-actin (SM alpha-A) gene
```

-continued regulatory region 5' promoter and intron
genomic sequence

<400> SEQUENCE: 1

| | | | | | |
|---|---|---|---|---|---|
| agtactgggt | tcaagggaaa | gatcctgtct | aaaagatcct | atggagacaa | tcgagggaca | 60 |
| taaacactat | cacccctgg | ctttcgcaga | cctatatatg | cacaagcatg | tgcccttgta | 120 |
| catgtaaatg | tgcacacaca | gaggcatgca | cacctgacat | cataccaaag | caaagatgaa | 180 |
| atgaagtaga | aatgtcaact | ctacatattt | tggtggttaa | tagttgcatg | tgtccagtgg | 240 |
| ctactgcatc | aggagttgct | gattctgggc | attcctgtca | ctaccagagc | taactcacca | 300 |
| ataccatgct | aagtcatctc | tggaccagag | cccagtgagg | actaaaatgg | tctccagttc | 360 |
| tcaagggctg | aactataaac | catcactaaa | tcacattgcg | gagacattct | gtgatgtctg | 420 |
| tggagcaata | cagctggaga | tgactcttca | gtgtgtgctt | atagcttgga | tttattttct | 480 |
| agtttccctg | aactgcaacc | aagtgaccag | atgtacgctc | cccaatcagt | ccatagctcc | 540 |
| ttgcatccat | ggctgccaac | cctggcagtt | atctaagcgc | tcagtggagc | tctgtaaact | 600 |
| tgtacgcact | catccagtgg | gcctttctct | cccagaagag | actggagctg | gatataaaat | 660 |
| ctcaaactct | ggctggagag | atggctcagt | gtttaagagc | actgactgct | cttccagagt | 720 |
| tcaaatccca | gcaaccacat | ggtggcttac | agccatctgt | aatgatattt | gatccctct | 780 |
| tctggtgtat | ctgaagacag | ttacactgtg | ctcataataa | ataaataaat | ataagtaaat | 840 |
| aaataaataa | atatttttaa | aaaccctcaa | actcacacat | tgtgaccatt | aattacttgc | 900 |
| tcaaaaattg | agcaaatcct | ccttggttac | ttcagattgc | ttttgaaat | tcttaaaata | 960 |
| aataaaacaa | ctgaaactta | ctttcttctt | cttgtcataa | tattctgatt | attgacaaat | 1020 |
| acaaccagta | taaacaaaaa | agttataaga | ttatcaaagc | tcttttcttg | gttttaaag | 1080 |
| gaattagcat | cttgaaatga | ccaagacaac | actccaacac | tcatgaaaca | aaacatcagc | 1140 |
| acagatatcc | atgccaggtt | ctaaagtaaa | aaataaaaca | agaaacaaaa | acaaaacaaa | 1200 |
| aaaaaacaaa | aaaacaaaga | aaaacatgga | actttacttt | atatgatgcc | tatgataaaa | 1260 |
| ccggttgcat | taatcataaa | tgtcccatcc | tgcctcacaa | aatgcagtct | ctgtatttga | 1320 |
| gtgatcagac | aatgtatttc | tagttggtga | aaccagatac | agagtagaaa | actcttaagc | 1380 |
| aacacaaaga | agccccatta | ttatttagca | accattacac | tcttctaaga | gtcaacggtg | 1440 |
| taattctcaa | agacagctat | gcgtgcctgg | gtgcaggtgg | acaccattaa | tcaagagcat | 1500 |
| gagacatggt | agcgtgagta | gacagctgct | ggcattcacc | ctgggctttc | cctgacatgc | 1560 |
| caacagttca | gagccactta | tggatccgtc | taaaatatct | ccatcatgaa | ttgaatcaga | 1620 |
| accttggctt | gcaggaggga | agtagagaaa | ggtaaagtcg | ttgactgtcc | attgaagcca | 1680 |
| aagagctgat | gatgtctttg | aagaatggca | gggtcacttg | atcgctcttt | ctgtccagtg | 1740 |
| ggctcataaa | cacggaggag | gatgagcagg | cttcatttca | acatttcaaa | cttcttttac | 1800 |
| aattttttt | atgacggggc | aatgggtcct | ctctgtggcc | aaaagacggt | ccttaagcat | 1860 |
| gatatcaggg | gtcagcgata | aaccaacaac | atgcacgtgg | actgtaccta | ggggttaacg | 1920 |
| cagttacagt | gattctgact | tctaagttcc | tcttagggta | acataggctg | gtgaatcctg | 1980 |
| attacatact | tccatatgta | atacatacag | acttcattga | tactacacac | agactccaga | 2040 |
| ctacatacaa | tgtggcttcc | ataaaatgat | cactcctctg | cagattcgca | ggtgacccaa | 2100 |
| gcatcttttg | ttataggcta | cctttttgcaa | cagtgttgcc | ttaaagtccc | agctagtcag | 2160 |
| agacaggccc | ttcctcatct | caagcccctta | gctaatggac | ccaaaggcta | gcctgacagg | 2220 |

```
aagagctggc atcttctgag gaatgtgcaa accatgcctg cgtctgcttc atgacactag    2280
cccagtgtct gggcatttga gcagttgttc tgagggctca ggatgtttat ccccataagc    2340
agctgaactg cctcctgttt cgagagcaga gcagaggaat gcagtggaag agacccaggc    2400
ctctggccac ccagattaga gagttttgtg ctgaggtccc tatatggttg tgttagagtg    2460
aacggccagc ttcagcctgt ctttgctcct tgtttgggaa gcgagtggga ggggatcaga    2520
ccagggggct atataaccct tcagcattca gcctccccag acaccaccca cccagagtcg    2580
agaagcccag ccagtcgcca tcagggtaag gatgtgactt agagttttcc caggcttttt    2640
aatcatccag tggaaccaga cgttgtctgt agtaatctga atgactcaca tgtttggaat    2700
ttgggaataa agatttatgc tgttaaaatg attgtagctc cttagcttgc atgatttcgt    2760
atctaaacgg gactaaaaat gaatcgtggt ttactggcaa aggagatgga gaggaaatta    2820
aagtttgttc atgcgtggca tctgtgaaat ctgtttacac taaaccaact gctcggatcc    2880
cgcagcctac tataggggag aagtccagcc atctatggta aattatacat ttgtttctac    2940
ttaggtgttg gacacttgtg gatttgtcta tggttcagac ttagtgtgag gactttccat    3000
ctgaccgact acagccgggt taactggaac tggatgtcag gagtgaactg gcgcggttgc    3060
ctgcgctctg gttttggctg agtggactgc gttgcctctg ggtttccggg gctctaacag    3120
tagacatgta tatcttgtgc ccttacgatt caaacctatg tcattggtca tttgcagcaa    3180
agcatagctc ctctactctc tgcaaagaaa tgaggaagtg tctcattcgg gaaggatctg    3240
attgcgtttc tctgcctcaa gtgtccctct ggcccttag gcagaatctc tgtgggagcc    3300
accccactca ggacttggta acttctgcag ggaaacggag ttttctcgat aagattttcc    3360
tccccttttg tgattcatga ctaaatatgg tttgcgtttt gagactcaca aactggggaa    3420
ggttactgtc ctttcctcct ccctcccctc ccctcttaca attcatttt ggcacaagat    3480 gagctccact gtgctgcacc aaactccccg gcctcgggtg cagttccaaa agcggacgct    3540
ggagcccagt gtgttttacc taattaggaa atgctccctg cttcaaactg aagctgctcc    3600
ttcaggttag ataagagttg caaaccacag cggcagtttc ctctggaaac acaccgacgt    3660
cttctctagt gacgacgctc ctttcaaagc ttattaagac atatttctg gatattttgg    3720 atgaagtaga aatacgtctt tactgaatta gtgattttta cttgcatttt aaaaaaaaac    3780
taggaagctt atttctctga atatactaag gcacaacctt aagtcatcct gcccaacagt    3840
ttatgtgggt tatccttccc cgttttcaaa gggcatccta attccgagtg gtttatctca    3900
tttgcagccc ggatgctatg ttttggacag caggcttcct gtagactctc tgctggtcct    3960
ttgctgctgg ctgcctctgc caatcacctg gctgctgtgc ctctctgtgc tttgagactg    4020
tcttctgagt ctttatcgtc cactggaaag gaagctaaat ataaattcag tgtctgaaag    4080
aagaggcaga gtagagagag gaaagagcaa accaaccaag atcccatttt tccgttcttg    4140 tgagggaac ccaggcattg aagatttcac tctgattttg gaggcagggt ttgaaaggaa    4200
accaaaatca caaacagaat ctctgggtaa agacaatagt cacatggtga gatcgacaag    4260
caatgcttgt acaatgccct tgatgtcccc cgaagctgtc gaaaacacaa gcttaaatgt    4320
caattactta aaatgctatt ttaagcccaa aagagtatgt gctcagttag tcaaggttag    4380
aagaaatacc agaactcagg ggaggaaaaa atatttataa aacctgatac ttgccacttc    4440
caaagaaccc cagtaaatat tttggagaga ataagtaagc tttggggggtg agggagtggg    4500 gggcaattca cttttattta cggtcatatt aagtttcttt ctgtaactta tcagtcttaa    4560
gtaagaatag ctattatcat cctgttgggt tttcagctta gcagtgattt tgattaatga    4620
```

```
ggaaatgttg taaatcctaa aattgcaaac tcccccatca aaattttca atccaatatt      4680 ttttactaga gtaggacttg gtagcctttc aacttgtgat cctcctgcct cagcttccca      4740
agtggtagga tcacaggtct acatcaccac gcccagtctt gattcatgtc taatgccaca      4800
ccagcaccca agtcttcaga gacaaaagat ttttcttta  aacatttaat atgagcaaac      4860
attttaacat tctcatatgc tgcccattat tccaaaatct accttttttgg gggaaaatat     4920 attttaccaa aaaaaaagt gactttggtt tgatatagat aacaaacctt ggtttgatat       4980
agataacaaa cctttctaga tagttcttta acatgtggta tcactattcc ctatagacct      5040
gtgttctcca ctcaggacct ctcatctgtg ctctgtggcc tgttcacaca ctaatgctct      5100
gccctgcttg agagtggtaa aagagcctgt gagctcctgc tctttgtgct gagggcttgt      5160
ggtgctaacc tggaagtcag ggtttcagct catcaaaggc cttacagtct ggtgaaagca      5220
tttcaagata aagagtgtta gttgagatct ggggagagcg tccagctaaa ataacacaac      5280
agggccaaga accctggttg tggttgggag tgaccgtagg ctccggccaa acgcaacctc      5340
ga                                                                     5342
```

<210> SEQ ID NO 2
<211> LENGTH: 326
<212> TYPE: DNA
<213> ORGANISM: Rattus sp.
<220> FEATURE:
<223> OTHER INFORMATION: smooth muscle alpha-actin (SM alpha-A) gene
      regulatory region intronic promoter fragment

<400> SEQUENCE: 2

```
ggaaacggag ttttctcgat aagatttttcc tccccttttg tgattcatga ctaaatatgg       60
tttgcgtttt gagactcaca aactggggaa ggttactgtc ctttcctcct ccctcccctc       120
ccctcttaca attcattttt ggcacaagat gagctccact gtgctgcacc aaactccccg       180
gcctcgggtg cagttccaaa agcggacgct ggagcccagt gtgttttacc taattaggaa       240
atgctccctg cttcaaactg aagctgctcc ttcaggttag ataagagttg caaaccacag       300
cggcagtttc ctctggaaac acaccg                                            326
```

<210> SEQ ID NO 3
<211> LENGTH: 1047
<212> TYPE: DNA
<213> ORGANISM: Homo sapiens
<220> FEATURE:
<223> OTHER INFORMATION: smooth muscle alpha-actin (SM alpha-A) gene
      5' promoter region

<400> SEQUENCE: 3

```
agagagcaag caagagcagg gaaaactgcc ttataaaacc atcagatatc gtgagaactc       60
actcactttc atgagaacag catggtataa aacgccccca tcgatccagt cacctcccac      120
catgcctttc tctggacatg ggattatgga gattagaatt cgagacgaga tttgggtggg      180
gacgtagaac caaaccatat cacctggtct ctctacttcc tgtcaaggag gttagtgggc      240
agagaggagg gctacagagg cttcctttga acaatctcct ttcttttcca aactacttct      300
ttgacaggct gctgggtaga ctctctggtc aaaggatggt ccctactat  gctgctaaat      360 tgctcggtga caaattagta gacaaagcta atgcaccaaa aaaatgaatg tagttatagt      420
aatgctaaca tccaaattcc tcttttgtaag acataggcct gtcaaccttg tctccatact      480
tcaattccta tttccactca cctccctcaa gaacttgatt tataaacagt gtgcctacca      540
```

-continued

```
taaaatcatc actccctcta tgtatttata gacgactgaa ggaatatctt tcttctttgc      600
atgctaccgt ggtagaagga ttttaaaagt ccatgctagg cagaggcagc cctttctgcc      660
cctttctgtt ctcagtttat taggaaatag cctgaaattc cagcatgata gcaactggca      720
tccgtctgtg aatgtgcaaa ccatgcctgc atctgcccat tacccgtagc tcagtgtctc      780
tgggcatttc tgcagttgtt ctgaaggctt ggcgtgttta tctcccacag gcggctgaac      840
cgctcccgtt tcatgagcag accagtggaa tgcagtggaa gagacccagg cctccggcac      900
cagattagag agttttgtgc tgaggtccct atatggttgt gttagactga acgacaggct      960
caagtctgtc tttgctcctt gtttgggaag caagtgggag gagagcaggc caagggctat     1020
ataacccttc agctttcagc ttccctg                                         1047
```

<210> SEQ ID NO 4
<211> LENGTH: 1056
<212> TYPE: DNA
<213> ORGANISM: Rattus sp.
<220> FEATURE:
<223> OTHER INFORMATION: smooth muscle alpha-actin (SM alpha-A) gene
      5' promoter region

<400> SEQUENCE: 4

```
gacatggtag cgtgagtaga cagctgctgg cattcaccct gggctttccc tgacatgcca       60
acagttcaga gccacttatg gatccgtcta aaatatctcc atcatgaatt gaatcagaac      120
cttggcttgc aggagggaag tagagaaagg taaagtcgtt gactgtccat gaagccaaa      180 gagctgatga tgtctttgaa gaatggcagg gtcacttgat cgctctttct gtccagtggg      240
ctcataaaca cggaggagga tgagcaggct tcatttcaac atttcaaact tcttttacaa      300
ttttttttat gacggggcaa tgggtcctct ctgtggccaa aagacggtcc ttaagcatga      360
tatcaggggt cagcgataaa ccaacaacat gcacgtggac tgtacctagg ggttaacgca      420
gttacagtga ttctgacttc taagttcctc ttagggtaac ataggctggt gaatcctgat      480
tacatacttc catatgtaat acatacagac ttcattgata ctacacacag actccagact      540
acatacaatg tggcttccat aaaatgatca ctcctctgca gattcgcagg tgacccaagc      600
atcttttgtt ataggctacc ttttgcaaca gtgttgcctt aaagtcccag ctagtcagag      660
acaggcccct cctcatctca agcccttagc taatggaccc aaaggctagc ctgacaggaa      720
gagctggcat cttctgagga atgtgcaaac catgcctgcg tctgcttcat gacactagcc      780
cagtgtctgg gcatttgagc agttgttctg agggctcagg atgtttatcc cataagcag      840 ctgaactgcc tcctgtttcg agagcagagc agaggaatgc agtggaagag acccaggcct      900
ctggccaccc agattagaga gttttgtgct gaggtcccta tatggttgtg ttagagtgaa      960
cggccagctt cagcctgtct ttgctccttg tttgggaagc gagtgggagg ggatcagacc     1020
agggggctat ataacccttc agcattcagc ctcccc                                1056
```

<210> SEQ ID NO 5
<211> LENGTH: 1074
<212> TYPE: DNA
<213> ORGANISM: Mus sp.
<220> FEATURE:
<223> OTHER INFORMATION: smooth muscle alpha-actin (SM alpha-A) gene
      5' promoter region

<400> SEQUENCE: 5

```
acaccataaa acaagtgcat gagccgtggg agcgtgagtc gacagctgct gccattcacc       60 ctgggggttttc cctaacatgt gcacagttca gaagcactcc cagaatccat ccaaaatatc     120
```

-continued

```
tctatcatga atggaatcag aaccttggct tgcaggagga aagtacagaa atgtaaagtc      180
actgactgtc catcaaagcc aacgatctga tgcctttgaa gaatgatagg gtcacttgag      240
gtcacttgat ctctgtttct gtccagtggg ctcatagtca tggaggagag tgagcaggct      300
tcatttcaac atttcaaatt tcttttacaa agttttttt tttttttatg acagggtgac      360
tggtgatctc tgtgggcaaa ggatggtcct taatcatgct gttaagggtc agtaaaaagc      420
cagcaacatg cggaatgtta agggttaaag cagttacagt gattctgact tctaagttac      480
tctttgggca acacaggctg gttaatcctc actacatact tcagttcctg gtttcattac      540
tacaacacaa agacacaatg tataagtaca atgtagcttc cataaaaaca tgactcctct      600
gcatatttat gggtgactcg aagcatcttt tgatctaggc tacctttgc aacagtgttg      660 cttaaaaatc gcagctagtc agagacaggc ccttccttat ccaagtcctc agctaatggc      720
ccaaaagact agcctgacag gggctggcat cttctgagga atgtgcaaac cgtgcctgcg      780
tctgtcccat gacactagcc cagtgtctgg gcatttaagc agttgttctg agggcttagg      840
atgtttatcc ccataacgag ctgagctgcc tcctgtttcg ggagcagaac agaggaatgc      900
agtggaagag acccagcctc tggccaccca gattagagag ttttgtgctg aggtccctat      960
atggttgtgt tagagtgaac ggccagcttc agcccgtctt tgctccttgt ttgggaggcg     1020
agtgggaggg gatcagagca agggctata taacccttca gccttcagcc tccc           1074
```

<210> SEQ ID NO 6
<211> LENGTH: 1013
<212> TYPE: DNA
<213> ORGANISM: Gallus sp.
<220> FEATURE:
<223> OTHER INFORMATION: smooth muscle alpha-actin (SM alpha-A) gene 5' promoter region

<400> SEQUENCE: 6

```
gaattcatgg gcttttgaa tttgtagtgg tttgagatgg agtttggaga tgctaatttc       60
tgatctctag tagtagttca agggcaatgt attgttactg tgaaagggct gctcatgaga      120
cacagtctgc ctagagaaca gctggctgca gccaaataaa tccagtcctc tgaaaatagc      180
tcatacattg agaacctttg ctttagttgc taaaaatatg ctcagggcaa agctagctag      240
aggttatgaa attcagcaac tttattatga atgttttgag ataggagttt acaacttgtg      300
tccatcagtg gaattgacac taggatgaag cttgtccaca gttcctagtg ctttggaaat      360
aaactgatgg agacaggata ttgattgtca cccattacag gctaggggca cataacaac       420 ctgttagcag aacgtttaca cagccttcaa agaccctacc atgaaccta tgcaacagca       480 ggtacttctt ttagtatccc caagtgcaga cctttaagt gaatttgtgg caaaattcag       540
tagctgttta gcttgccgaa agtattctca ttgctttggt ccaaatcttt aacaaatgca      600
aagtgtctcc ttaaaaacac tttccctatt acaaatgact gctctttcag ttttcactct      660
gcctcttgga tgttcctgtg aaggccaggg cctctctctc ttgtttgaac gtgtgctctt      720
cctgacagag ggtgtctgtc ccaggcacgc ttttcttgct gcattttagc aagttctgca      780
gtgtttatct tacacagctg aaagtctcct cctgtttcat gagctctgcg ttggaatgca      840
gtggaaggga ctgagggcct gtcgacccag attagaggtt tttgtaataa ggtccctata      900
tggttttgtt agagacttcg gctctgtctc tctcatctct gctccttgtt tgggaggctg      960
gtgggaggag aagagctgaa ggggctatat aaccctggtg cttttggata cac            1013
```

<210> SEQ ID NO 7
<211> LENGTH: 2771
<212> TYPE: DNA
<213> ORGANISM: Homo sapiens
<220> FEATURE:
<223> OTHER INFORMATION: smooth muscle alpha-actin (SM alpha-A) gene first intron sequence

<400> SEQUENCE: 7

```
gtaagtgcgc caggccaagg atgtgactta tagattccag tggctctttt aattacccgg      60
tataataaga caccatctgc agggatttgg ctgggttcat gcactgatat ttctgaatga     120
agattgtact actaaaatga ttgtagcttt tggctttaat gatctaacgt taaagacagg     180
gctaatatgt agtttggtat gatggaaggg gtagagaaga atatgaaaat tttattaatg     240
catgtcttct gtaaaatgtt catcctaaac aaacagccca gatcttgcag cacaatacag     300
gtatgcaggt tagctgtgtg cagtaagtta tacatttatt tgtatttagg cactggaaac     360
tcagatttct ttctggttct gatttgttgt aggggttttc tttcactggg ctgtattttt     420
ggtgcagctt aggtgtctgg aagtcggatt ttggaagtga acagaagaat agttgcctag     480
tctttgattg tgcctgaatt tgtgtattcc cttctggttt ccctgctcta actggtagtg     540
tcttttgttg gaaatgtata tctctttttt gttggaaatg tgtatgtgtg accttacaag     600
tttggatcta catcattggt catttgcagc agagcgcagc aggtgacctg ctgaattttt     660
ctctggaaag aaagatttag ggagcagagc ctgcatctga cagctgtgtg tcctcccggc     720
cggatatctg gttgcatctc cctcagctta aagctccctt cagcctggtg aggcaagtgt     780
gactgtgcag ccagccctgc aacccaggc tgagtttcac tgcaaatcaa ggtttggcag      840
cttcagccca gactggagtt tcatgctga gattttccta gcattttgtg tttcatggac       900
taaatatggt ttgtgtttca agaccaatga gctgggaact gtactgttct ttcccctccc      960
atcaactcat ttttggcaca agacgcactc tagtcagttg gagcaaaccc ctgacccggg    1020
tgcagttcca aaagcagaca ctcgagcgtg ttttacctaa ttaggaaatg ctttgctcca    1080
aaccgaactg ctcattcagg ttagagagga gctgtaaacc actgagctcg actctttccg    1140
gggacacagt gacttcttca atgacagtgc tccttttgga cattataaca ttcttcctag    1200
atttctcttt tcttttttctt tttttttttgg ccaagtaaaa acatttttc tgcattcttg     1260
ctgatgctga gggccagtct ccttttttctg agtatagtca acccctcctc ccaagccatc    1320
actgcccaac aaaacagtta ttaaaaatat cccacattca tggtaaccat accttcccat    1380
tttcagagac catcctaatt tgaaatgttt tatcctcttt tcagcccctta cttttggttt    1440
ggaaaatgca cttagcacat ccatagagtg cctgcttatc ccctggggct ggctgcttct    1500
gacagatacc ccaggctctt aggcttcttc ccttttttct cctttatagt tctcgcctct    1560
tttctaaagc ttcttaatct gctctgaggg aagccaaatc acaggaatgc caaataatt     1620
cagcatctgg aaagggaaaa gaagggtggg aaggaaagg gcaagccatt catgagtccc     1680
atgtccattc ttgcaagtgg aatccacacg ttgattattt ttattctaag cctggagcag    1740
tgtgaaagaa aagcaaaggt tagaaacaaa gagttctgga tactgaaaat aatcacacag    1800
tgatagtaat aataatgatg atgaaattag tatttattga gaacttagag tatctctgcc    1860
actataaatt attttaaaca ctttaaaaaa cccaatctct ataagaactc catgaggtat    1920
gtcctgatat cattactgtt ttatagtaag gaaattgtgg tttagagatg ttaaataact    1980
gaaatcacac agcttttaac tgttggagcc tggactcaaa tccaggcttt ctgacttcag    2040
agtctaagct cataatcatg tgatctgaaa tcttcgttgt cctaaatgta tcagttcaag    2100
```

-continued

```
gctcttggac aagtcacttc aactccttaa gccttggttt ccttgtcagc tgaagataat    2160
attacatgcc ttgactttaa aatatgtcat ctcaattgca gttttatgtt ctttgcaaag    2220 agttattta catgaagcac tgctaaggaa gttttaggcc tttggcaaga tgcaggtttg     2280
attttgtggg aatgttttgg cagaactcca actctgtaat agctatttta tttccctact    2340
tctcagatgt ttccttaaaa gaactgcctt ttttatatgg atttggaggt gcaatcagtt    2400
aacccattta gaagaagaaa ttttctcaat ttgaaatcct aattgagatc tcaatgccag    2460
gcagataact ctgggtgtcc ttctcttaac ggaacatttc gacctaattg tgattagaaa    2520
agtggaagag gtcttgaact ggaagccaag gggtggctaa agagtacctg atgtctggct    2580
ggagctctcc tctaatgccc tgtgtgccct tgagcaatca cttcctgatt tcttatttg     2640 tgaaaatgag agcattggat gaaaatgtcc tctaatatgc cttcaatttc tcaaatttgt    2700
aagttgatag gctgctccag cctttctaat tttatgaaag gatccaagta taagatccaa    2760
gtataaaatg g                                                         2771
```

<210> SEQ ID NO 8
<211> LENGTH: 2678
<212> TYPE: DNA
<213> ORGANISM: Rattus sp.
<220> FEATURE:
<223> OTHER INFORMATION: smooth muscle alpha-actin (SM alpha-A) gene
      first intron sequence

<400> SEQUENCE: 8

```
gtaaggatgt gacttagagt tttcccaggc ttttaatca tccagtggaa ccagacgttg     60
tctgtagtaa tctgaatgac tcacatgttt ggaatttggg aataaagatt tatgctgtta    120
aaatgattgt agctccttag cttgcatgat ttcgtatcta aacgggacta aaaatgaatc    180
gtggtttact ggcaaaggag atggagagga aattaaagtt tgttcatgcg tggcatctgt    240
gaaatctgtt tacactaaac caactgctcg gatcccgcag cctactatag gggagaagtc    300
cagccatcta tggtaaatta tacatttgtt tctacttagg tgttggacac ttgtggattt    360 tctatggtt cagacttagt gtgaggactt tccatctgac cgactacagc cgggttaact     420
ggaactggat gtcaggagtg aactggcgcg gttgcctgcg ctctggtttt ggctgagtgg    480
actgcgttgc ctctgggttt ccggggctct aacagtagac atgtatatct tgtgcccta    540 cgattcaaac ctatgtcatt ggtcatttgc agcaaagcat agctcctcta ctctctgcaa    600
agaaatgagg aagtgtctca ttcgggaagg atctgattgc gtttctctgc ctcaagtgtc    660
cctctggccc cttaggcaga atctctgtgg gagccacccc actcaggact tggtaacttc    720
tgcagggaaa cggagttttc tcgataagat tttcctcccc ttttgtgatt catgactaaa    780
tatggtttgc gttttgagac tcacaaactg gggaaggtta ctgtccttc ctcctccctc     840 ccctccccctc ttacaattca tttttggcac aagatgagct ccactgtgct gcaccaaact    900
ccccggcctc gggtgcagtt ccaaaagcgg acgctggagc ccagtgtgtt ttacctaatt    960
aggaaatgct ccctgcttca aactgaagct gctccttcag gttagataag agttgcaaac    1020
cacagcggca gtttcctctg gaaacacacc gacgtcttct ctagtgacga cgctcctttc    1080
aaagcttatt aagacatatt ttctggatat tttggatgaa gtagaaatac gtctttactg    1140
aattagtgat ttttacttgc attttaaaaa aaaactagga agcttatttc tctgaatata    1200
ctaaggcaca accttaagtc atcctgccca acagtttatg tgggttatcc ttccccgttt    1260
tcaaagggca tcctaattcc gagtggttta tctcatttgc agcccggatg ctatgttttg    1320
```

```
gacagcaggc ttcctgtaga ctctctgctg gtcctttgct gctggctgcc tctgccaatc   1380
acctggctgc tgtgcctctc tgtgctttga gactgtcttc tgagtcttta tcgtccactg   1440
gaaaggaagc taaatataaa ttcagtgtct gaaagaagag gcagagtaga gagaggaaag   1500
agcaaaccaa ccaagatccc attttttccgt tcttgtgagg ggaacccagg cattgaagat   1560
ttcactctga ttttggaggc agggtttgaa aggaaaccaa aatcacaaac agaatctctg   1620
ggtaaagaca atagtcacat ggtgagatcg acaagcaatg cttgtacaat gcccttgatg   1680
tcccccgaag ctgtcgaaaa cacaagctta aatgtcaatt acttaaaatg ctattttaag   1740
cccaaaagag tatgtgctca gttagtcaag gttagaagaa ataccagaac tcaggggagg   1800
aaaaaatatt ttaaaacctg atacttgcca cttccaaaga accccagtaa atattttgga   1860
gagaataagt aagctttggg ggtgagggag tggggggcaa ttcactttttt attacggtca   1920 tattaagttt cttctgtaa cttatcagtc ttaagtaaga atagctatta tcatcctgtt   1980
gggttttcac aaactccccc atcaaaaatt ttcaatccaa tattttttac tagagtagga   2040
cttggtagcc tttcaacttg tgatcctcct gcctcagctt cccaagtggt aggatcacag   2100
gtctacatca ccacgcccag tcttgattca tgtctaatgc cacaccagca cccaagtctt   2160
cagagacaaa agatttttct tttaaacatt taatatgagc aaacatttta acattctcat   2220
atgctgccca ttattccaaa atctacctt ttgggggaaa atatatttta ccaaaaaaaa   2280
aagtgacttt ggttttgatat agataacaaa ccttggtttg atatagataa caaacctttc   2340
tagatagttc tttaacatgt ggtatcacta ttccctatag acctgtgttc tccactcagg   2400
acctctcatc tgtgctctgt ggcctgttca cacactaatg ctctgccctg cttgagagtg   2460
gtaaaagagc ctgtgagctc ctgctctttg tgctgagggc ttgtggtgct aacctggaag   2520
tcagggtttc agctcatcaa aggccttaca gtctggtgaa agcatttcaa gataaagagt   2580
gttagttgag atctggggag agcgtccagc taaaataaca caacagggcc aagaaccctg   2640
gttgtggttg ggagtgaccg taggctccgg ccaaacgc                          2678
```

<210> SEQ ID NO 9
<211> LENGTH: 2719
<212> TYPE: DNA
<213> ORGANISM: Mus sp.
<220> FEATURE:
<223> OTHER INFORMATION: smooth muscle alpha-actin (SM alpha-A) gene
      first intron sequence

<400> SEQUENCE: 9

```
gtaagtagcc ccagcccagg gatatgactt cgagttttcc caggctcttt tatcatccaa     60
tgtagccaga cattgtctgt gggaatctga atgactcacg tgttttgaat ttttgaataa    120
agatttatac tgttaaaatg attgtagctt tttagcttgc atgatttac atccgaatag     180 ggctgattta ctggaaacaa cgcttgattt actggaaaag gaaatggata gaaaattaaa    240
gtttgttcat gtgtgtcatc tgcaaaacct gtttacacta aaccaactgc tctgatcccg    300
cagcgtactg taggggtgga gtctagctgt atgtggtaaa ttatacgttt gtttctatta    360
ggcaaaagtt ggaaactttt ggatgtatca tgatgtagca tgaggtattt agtgcagctg    420
aggtaactgg aagtgaatat caggaatgaa ctgaggtagt tgcctgctct ctgatgttgg    480
ctgagtggac gcattgcttc tgggtttccg gggctctaag agctggtgtc ctatgctgga    540
aatgtgtatc ttgtgactgt gttggtgccc ttacaagtca gacctatgcc attggtcatt    600
tgcagcatag catagctttt ctactttctg caaagaaagg aggaagtgtc tcatccaggg    660
```

-continued

```
gagatctgat ttgcatttct ctgcctcacg tgtccctcag ccgcttaagt atctgtggaa    720
ccagccttgc caccccacat tgtaactcag ggctcggtag cttcatcagg gaatggagtt    780
ttctcgataa gattttcctc ctgttttgtg attcatgact aaatatggtt tgcatttgag    840
actcataagc tgggaagggt actgtccttt cctcccttcc ccctccccc caacaattca     900 tttttggcac cagatgagct ccactgggct gcaccaaact cccgccccg gtgcagttcc     960 aaaagcagag gctggagccc agtgtgtttt acctaattag gaaatgctcc ccgcttcaaa    1020
ccgagctgct cattcaggtt agataagagt tgcaaaccac agcggctgcg tcctctggaa    1080
acacacagac ttcttctcca gtgacaagcc tcctttcaga gcttaataag acaatttttt    1140
cctggatatt tttgatgaaa tagaaataca tctttacgga atttgacagt attttttcct    1200
gcattttttt aaaaccagg gtagcttatt tttctgaata tactaaggca caaccttaag     1260
ccatcttgcc caacaaaag tttatgtggg ttatccttcc ccattttcag agggtatcct     1320
aattccaagt ggcttatccc atttgcagcc ctggtgctaa gtatgaaaaa caggcttagt    1380
ggacacacag actctctgct ggtcctttgg tggtttctgc ctctgccagt cacctggctt    1440
ctgtgcctcc ttgtggtttg aaactttctt ctgagtcctt atcatccact ggaaaggaag    1500
ctaagtataa ttcagaggca tagtggaaag aggaaagagc aaactgctga agaaagggat    1560
tttcccattc ttgcaagggg aacacattga agatttcact ctgatcttgg ggacagggtt    1620
gaaagaaaac caagatcgca aacagaatct ttgggtaggg ataatagtta cttgatgata    1680
tccacgcgca atgcttgtcc aacactctgg atgtcctttg aagctctcaa aaatccaagc    1740
ttaaatgtca attccttaaa ttgttgttaa aaacaaccct aagggtata tactcagtta     1800 atcaagctta gaagaagata ccagagctca gggaagaaaa aaagtctaca aaagctgatg    1860
cttgccactt caaaagaatc tagtaacatt tggacagaat aagtaagctt tgggtagagg    1920
aacaactcac attttattaa ggtcatatct gtctctttct gtaacttatc agtcttaaac    1980
aagaatagct ctcagcaacc tgttgggttt tcagcttaac agtgacttta ataaatgaag    2040
aaatgttata actcgtaaaa tttcaaacac catatttgga aatttctatc caagtttcca    2100
tattagacca gctccttaac ttgtgatcct cctgcctcag cctccaagtg ctaggatata    2160
ggtgtacatc atcacaccca gccttgattc atatttaata cctcaccggc tcacaagtct    2220
ttagagccaa aagttttctc ttttaaacat ttaatatgag taaacatttt aacattttca    2280
aattctcaca tgctgcccat tccttgaaaa tctacctttg gtgggggggg ggggggggact   2340 atatatatat atgtccctat agaactctgc tctctacact gcatctctca tctgtgctct    2400
atgatctatt cacacactaa tgctctgacc agcttgagag tgtttataaga gcctgtgaca   2460 ctcccgctct ttgtgctgag gacttgtggt gttaacctgg aagtcagggt ttcggatcat    2520
caaaggcttt acagcctagt gaaagcattt caagataaag ggtgttagtt gagaactgtg    2580
gagagcctcc agctaaaata acacaacagg accaagaacc ctgtctgtgg gtgggagtga    2640
ctaggctcta gccaaatgct ctgcgctaca gtagcttctc gctcgctgtc tctgcagaac    2700
cctgagacgc tgctccagc                                                 2719
```

<210> SEQ ID NO 10
<211> LENGTH: 2255
<212> TYPE: DNA
<213> ORGANISM: Gallus sp.
<220> FEATURE:
<223> OTHER INFORMATION: smooth muscle alpha-actin (SM alpha-A) gene first intron sequence

<400> SEQUENCE: 10

```
gtaagtggca ctgaaccaat agtgggattt atagttttct ggatgacttt aattaagtaa      60
tgtcacatgg aagctattca ggaggatgta ctgctatgct gcagtttgct taggcattac     120
ttactagaac tgaattggta aaatactttc aatgtctaca ctgagttgta tttgttttaa     180
agcacttttg aatgggaaat acgtctgatg attttgccga ttccaccaac actccaacgg     240
taatataaag acacagactg tttaatggca cagctggaat ttaagagaac ctgtgtgccc     300
ctgtggagtt agctttggac agaacagagt tcctgaatgg gtgaatttgc acactgtgta     360
gtggtttctc agcagctttg cttcagtgct ctcaaaatca gcttaaattg acgtaagtgt     420
tttggagtgt gactgcaaga agagctggaa gatgcaaaat agcagtatct aatcagatgc     480
aatgaggatg catgtgtatt cattgctgtc tcgatagata tgaaagctgt ggtctgcaaa     540
acgcccaata ttttattaaa gatcacatta tacacagagt tccttgtgag gctggagttg     600
ttctcctgat agcatgctgt agaggctggg gaagtgattg gttgtctttc agtgtaaagc     660
aggtagaagt aagaggctaa atactgtatt aattgctggg gtgaatatgt cctttattct     720
gcagtgtgag tgacttttgc tgctggagga tgttactact gcatgccatg gcagtccttg     780
agctgtaact cactccttgg aagagagtgt cctgcctgaa tgatttagct ttgattttta     840
gcttttgtg ctctattact aaatatggtt ttcattagag tcctccaagc tagaaatgca     900
gccttttcca gctccctcct ctcccctccc caagtgatt tttggcattg cattctctgc     960
attggtttga gcaaaccccc tgacctcgaa ctctgttcca aaaacagacg gttggaaagc    1020
atatttccta attaggaaat ggtttctcta aaccactctg ttcattcatg ttagataaca    1080
attgtactcc atagactaaa tgcttaaata taaagagcct gttttcccaa agtttaaga    1140
aagtgcgaaa aattgcaacc tactttcctt ttctggtaat aatgacttaa tatctggagt    1200
acatcaacgt gggatttccc tctccatgcc ttctcctggc agctactgta tccatcgaga    1260
actgcagcct gagaagcagt ccacagctgc gtgctcgtgg ctgtgaaggg tctgcagtga    1320
gaggcgtttg ggggaggctg tccctcctag gtccatctat ggtggaggct gaagcgttgc    1380
ctcatgctcc catgctcaat cagccatggc tctcactgac gcgcactgcc gcttcgacgt    1440
gcacgccagc aggcccatgg cagcaggttt tgatcgttcg cgaggagcca gctgggctgc    1500
tggatgacag cctgtctcgc tttggctgtt aacacattgc aatttgttga cctctgcatg    1560
gaagtccagg ctcccagcta gtcgagtgat tccctaacac actataaatt gtgggcaaat    1620
agttctcctc gagtgctggt attcggggct tgtttccgta attgactta atacaaaccc    1680
tttaaagcat ttttattacc cttgttatct tcctgttgcc tgaggagaaa acaatttct    1740
gttttagtga agcagggagc cagcataaat tactttgtca ttctacaaat gcagcttatt    1800
agctggtttg aaatgatgat ggagcacaca ctatggacag tttcaaaaca catgctgtcc    1860
ttgattgcat tttaaagtca ggatatcatc tttctacgtg caccagtctt gtcaggatga    1920
tagaggcagg ggacatcata ctgaatctga tgcaaagaga cctttgtttt tgcagctgtc    1980
agtccagcag tcttctttat ctcccaccta cgcctcagtg gtggatttcc gtggccgaat    2040
ttagataaac attcgctgtc tcaaagctgt aatgatctgt cttccatgc agcaggactg    2100
gaatagttcc atggagtact tgaattatg tctggtgcat acagccttcc tgcctatcag    2160
ttccttttat accgcattct ctgtcttaca gggtggttct ggtacctcac tttgttgttt    2220
tttttttcaat tattctttc ttgctgtttc catag                              2255
```

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence:site-
      directed A mutant sequence, mutated CARG sequence CARG A, gel
      shift analysis oligonucleotide A mut

<400> SEQUENCE: 11
aattgtttaa                                                              10

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence:site-
      directed B mutant sequence, mutated CARG sequence CARG B, gel
      shift analysis oligonucleotide B mut

<400> SEQUENCE: 12
ccctatatca                                                              10

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence:site-
      directed Int mutant sequence, mutated CARG sequence intronicCARG,
      gel shift analysis oligonucleotide Int mut

<400> SEQUENCE: 13
aataattaaa                                                              10

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:CArG A
      oligonucleotide probe used in electromobility shift assay (EMSA),
      human and rat conserved cis regulatory element CArG A in smooth
      muscle alpha-actin (SM alpha-A) 5' promoter region

<400> SEQUENCE: 14
ttgctccttg tttgggaagc                                                   20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:CArG B
      oligonucleotide probe used in electromobility shift assay (EMSA),
      human, rat and mouse conserved cis regulatory element CArG B in
      smooth muscle alpha-actin (SM alpha-A) 5' promoter region

<400> SEQUENCE: 15
gaggtcccta tatggttgtg                                                   20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:Intronic CArG oligonucleotide probe used in electromobility shift assay
(EMSA), human, rat and mouse conserved cis regulatory element
Int CArG in smooth muscle alpha-actin (SM alpha-A) first intron
promoter region

<400> SEQUENCE: 16
ttttacctaa ttaggaaatg                                              20

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence:PCR 5'
      primer complementary to E. coli Lac Z gene

<400> SEQUENCE: 17
gcatcgagct gggtaataag cgttggcaat                                    30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence:PCR 3'
      primer complementary to E. coli Lac Z gene

<400> SEQUENCE: 18
gacaccagac caactggtaa tggtagcgac                                    30

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Conserved
      region of Human AP1-like sequence
<220> FEATURE:
<223> OTHER INFORMATION: Description of Artificial Sequence: human
      conserved cis regulatory element AP1-like in smooth muscle
      alpha-actin (SM alpha-A) first intron promoter region

<400> SEQUENCE: 19
tcatggacta aatatggttt gt                                            22

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: human
      conserved cis regulatory element GATA in smooth muscle alpha-
      actin (SM alpha-A) first intron promoter region

<400> SEQUENCE: 20
ttcaggttag agaggagctg                                               20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: chicken
      conserved cis regulatory element CArG B in smooth muscle
      alpha-actin (SM alpha-A) 5' promoter region

<400> SEQUENCE: 21
aaggtcccta tatggttttg                                               20

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence: mutated
      sequence for CArG B

<400> SEQUENCE: 22
ccctatatca                                                              10

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: mouse
      conserved cis regulatory element CArG A in smooth muscle
      alpha-actin (SM alpha-A) 5' promoter region

<400> SEQUENCE: 23
ttgctccttg tttgggaggc                                                   20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:chicken
      conserved cis regulatory element CArG A in smooth muscle
      alpha-actin (SM alpha-A) 5' promoter region

<400> SEQUENCE: 24
ctgctccttg tttgggaggc                                                   20

<210> SEQ ID NO 25
<211> LENGTH: 10
<212> TYPE: DNA
<213> ORGANISM: Artificial Sequence
<220> FEATURE:
<223> OTHER INFORMATION: Description of Artificial Sequence: mutated
      sequence for CArG A

<400> SEQUENCE: 25
aattgtttaa                                                              10

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: rat
      conserved cis regulatory element AP1-like in smooth muscle
      alpha-actin (SM alpha-A) first intron promoter region

<400> SEQUENCE: 26
tcatgactaa atatggtttg c                                                 21

<210> SEQ ID NO 27
<211> LENGTH: 22
<212> TYPE: DNA
<213> ORGANISM: Artificial Sequence
<220> FEATURE:

```
<223> OTHER INFORMATION: Description of Artificial Sequence: chicken
      conserved cis regulatory element AP1-like in smooth muscle
      alpha-actin (SM alpha-A) first intron promoter region

<400> SEQUENCE: 27
tctattacta aatatggttt tc                                              22

<210> SEQ ID NO 28
<211> LENGTH: 10
<212> TYPE: DNA
<213> ORGANISM: Artificial Sequence
<220> FEATURE:
<220> FEATURE:
<223> OTHER INFORMATION: Description of Artificial Sequence:mutated
      sequence for AP1-like

<400> SEQUENCE: 28
gaggaagtat                                                            10

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:chicken
      conserved cis regulatory element intronic CArG in smooth muscle
      alpha-actin (SM alpha-A) first intron promoter region

<400> SEQUENCE: 29
tatttcctaa ttaggaaatg                                                 20

<210> SEQ ID NO 30
<211> LENGTH: 10
<212> TYPE: DNA
<213> ORGANISM: Artificial Sequence
<220> FEATURE:
<223> OTHER INFORMATION: Description of Artificial Sequence:mutated
      sequence for intronic CArG

<400> SEQUENCE: 30
aataattaaa                                                            10

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:rat and
      mouse conserved cis regulatory element GATA in smooth muscle
      alpha-actin (SM alpha-A) first intron promoter region

<400> SEQUENCE: 31
ttcaggttag ataagagttg                                                 20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence:chicken
      conserved cis regulatory element GATA in smooth muscle
      alpha-actin (SM alpha-A) first intron promoter region

<400> SEQUENCE: 32
ttcaggttag ataacaattg                                                 20
```